(12) United States Patent
Bischof et al.

(10) Patent No.: US 10,493,422 B2
(45) Date of Patent: *Dec. 3, 2019

(54) FOULING PROTECTION FOR AN OLIGOMERIZATION REACTOR INLET

(71) Applicant: Chevron Phillips Chemical Company LP, The Woodlands, TX (US)

(72) Inventors: Steven M. Bischof, Humble, TX (US); Orson L. Sydora, Houston, TX (US); Jared T. Fern, Kingwood, TX (US); Uriah J. Kilgore, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/262,164

(22) Filed: Jan. 30, 2019

(65) Prior Publication Data

US 2019/0160448 A1   May 30, 2019

Related U.S. Application Data

(63) Continuation of application No. 15/615,113, filed on Jun. 6, 2017, now Pat. No. 10,232,339.

(51) Int. Cl.
*B01J 19/26* (2006.01)
*C07C 2/08* (2006.01)
(Continued)

(52) U.S. Cl.
CPC ........... *B01J 19/1843* (2013.01); *B01J 4/001* (2013.01); *B01J 4/002* (2013.01); *B01J 8/003* (2013.01); *B01J 19/1806* (2013.01); *B01J 19/26* (2013.01); *C07C 2/08* (2013.01); *C07C 2/32* (2013.01); *B01J 23/26* (2013.01); *B01J 2208/00902* (2013.01); *B01J 2219/00247* (2013.01);
(Continued)

(58) Field of Classification Search
CPC .... B01J 19/1843; B01J 19/1806; B01J 19/26; B01J 19/18; B01J 8/003; B01J 23/26; C07C 2/08
USPC ........................................................ 422/214
See application file for complete search history.

(56) References Cited

U.S. PATENT DOCUMENTS

| 3,361,525 A | 1/1968 | Rycke et al. |
| 4,538,018 A | 8/1985 | Carter |

(Continued)

FOREIGN PATENT DOCUMENTS

| CN | 1490291 A | 4/2004 |
| DE | 1146892 B | 4/1963 |

(Continued)

OTHER PUBLICATIONS

Office Action dated Jun. 28, 2018 (24 pages), U.S. Appl. No. 15/166,991, filed May 27, 2016.

(Continued)

*Primary Examiner* — Huy Tram Nguyen
(74) *Attorney, Agent, or Firm* — Conley Rose, P.C.

(57) ABSTRACT

Disclosed herein are systems and processes which prevent fouling of a reactor inlet of an oligomerization reactor. The systems and processes involve placement of an inlet sleeve around at least a portion of a reactor inlet such that a curtain of inert material flows through an annular space coaxially with respect to an outer surface of the end of the reactor inlet and into the reactor.

22 Claims, 7 Drawing Sheets

(51) Int. Cl.
*B01J 23/26* (2006.01)
*B01J 19/18* (2006.01)
*C07C 2/32* (2006.01)
*B01J 4/00* (2006.01)
*B01J 8/00* (2006.01)

(52) U.S. Cl.
CPC ............... *B01J 2219/00252* (2013.01); *B01J 2219/00254* (2013.01)

(56) References Cited

U.S. PATENT DOCUMENTS

| | | | |
|---|---|---|---|
| 5,217,703 A * | 6/1993 | Goodson | B01J 12/02 252/62.56 |
| 7,276,566 B2 | 10/2007 | Muruganandam et al. | |
| 7,300,904 B2 | 11/2007 | Dixon et al. | |
| 7,361,623 B2 | 4/2008 | Dixon et al. | |
| 7,554,001 B2 | 6/2009 | Dixon et al. | |
| 7,989,562 B2 * | 8/2011 | Terry | B01J 4/002 526/59 |
| 7,994,363 B2 | 8/2011 | Gao et al. | |
| 8,252,956 B2 | 8/2012 | Gao et al. | |
| 8,367,786 B2 | 2/2013 | Dixon et al. | |
| 8,680,003 B2 | 3/2014 | Sydora et al. | |
| 8,865,610 B2 | 10/2014 | Sydora et al. | |
| 9,283,555 B2 | 3/2016 | Sydora et al. | |
| 9,707,549 B1 | 7/2017 | Kilgore et al. | |
| 9,732,106 B2 | 8/2017 | Sydora et al. | |
| 10,183,960 B1 | 1/2019 | Bischof et al. | |
| 10,232,339 B2 | 3/2019 | Bischof et al. | |
| 2002/0182124 A1 | 12/2002 | Woodard et al. | |
| 2003/0195307 A1 | 10/2003 | Kaji et al. | |
| 2004/0008572 A1 | 1/2004 | Stuart | |
| 2004/0152935 A1 | 8/2004 | Jones et al. | |
| 2005/0002841 A1 | 1/2005 | Moberg | |
| 2006/0223960 A1 | 10/2006 | Jaber et al. | |
| 2006/0247399 A1 | 11/2006 | McConville et al. | |
| 2007/0185360 A1 | 8/2007 | Buchanan et al. | |
| 2008/0207973 A1 * | 8/2008 | Palmas | B01J 8/0055 585/640 |
| 2010/0041841 A1 | 2/2010 | Terry et al. | |
| 2010/0222622 A1 * | 9/2010 | Overett | C07C 2/32 585/523 |
| 2010/0240847 A1 | 9/2010 | Dixon et al. | |
| 2010/0274065 A1 | 10/2010 | Sydora | |
| 2012/0142989 A1 * | 6/2012 | Jaber | C07C 2/36 585/532 |
| 2012/0309965 A1 | 12/2012 | Sydora et al. | |
| 2013/0090508 A1 | 4/2013 | Wang et al. | |
| 2013/0331629 A1 | 12/2013 | Sydora et al. | |
| 2015/0152200 A1 | 6/2015 | Hanton et al. | |
| 2016/0375431 A1 | 12/2016 | Carney et al. | |
| 2017/0349505 A1 | 12/2017 | Kilgore et al. | |
| 2019/0091675 A1 | 3/2019 | Bischof et al. | |
| 2019/0092708 A1 | 3/2019 | Bischof et al. | |
| 2019/0092709 A1 | 3/2019 | Bischof et al. | |

FOREIGN PATENT DOCUMENTS

| | | |
|---|---|---|
| EP | 0780353 A1 | 6/1997 |
| EP | 2684857 A1 | 1/2014 |
| WO | 0204119 A1 | 1/2002 |
| WO | 2004056477 A1 | 7/2004 |
| WO | 2004056478 A1 | 7/2004 |
| WO | 2004056479 A1 | 7/2004 |
| WO | 2004056480 A1 | 7/2004 |
| WO | 2005039758 A1 | 5/2005 |
| WO | 2005123633 A1 | 12/2005 |
| WO | 2005123884 A2 | 12/2005 |
| WO | 2007007272 A2 | 1/2007 |
| WO | 2007088329 A1 | 8/2007 |
| WO | 2008014139 A2 | 1/2008 |
| WO | 2008119153 A1 | 10/2008 |
| WO | 2010034101 A1 | 4/2010 |
| WO | 2010034102 A1 | 4/2010 |
| WO | 2010051415 A1 | 5/2010 |
| WO | 2011130822 A1 | 10/2011 |
| WO | 2011137027 A1 | 11/2011 |
| WO | 2011140629 A1 | 11/2011 |
| WO | 2012051698 A1 | 4/2012 |
| WO | 2012071644 A1 | 6/2012 |
| WO | 2012092415 A1 | 7/2012 |
| WO | 2012142693 A1 | 10/2012 |
| WO | 2013168106 A1 | 11/2013 |
| WO | 2015094207 A1 | 6/2015 |
| WO | 2015097599 A1 | 7/2015 |
| WO | 2017010998 A1 | 1/2017 |
| WO | 2017011127 A1 | 1/2017 |
| WO | 2019067466 A1 | 4/2019 |

OTHER PUBLICATIONS

Office Action dated Jun. 25, 2018 (43 pages), U.S. Appl. No. 15/719,107, filed Sep. 28, 2017.
Office Action dated Jul. 27, 2018 (24 pages), U.S. Appl. No. 15/167,017, filed May 27, 2016.
Imhoff, Donald W., et al., "Characterization of Methylaluminoxanes and Determination of Trimethylaluminum Using Proton NMR," Organometallics, 1998, pp. 1941-1945, vol. 17, American Chemical Society.
Office Action dated Aug. 2, 2018 (19 pages), U.S. Appl. No. 15/167,024, filed May 27, 2016.
Office Action (Final) dated Feb. 28, 2018 (43 pages), U.S. Appl. No. 15/167,017, filed May 27, 2016.
Morse, J. G., et al., "Substituted Difluoro- and Dichlorophosphines," Inorganic Syntheses, 1967, pp. 147-156, vol. 10, McGraw-Hill Book Company, Inc.
Singh, Rajendra P., et al., "The first application of SelectfluorTM in electrophilic fluorination of amines: a new route to -NF2, - NHF, and >NF compounds," Chemical Communication, 2001, pp. 1196-1197, vol. 13, Royal Society of Chemistry.
Office Action (Final) dated Feb. 6, 2018 (43 pages), U.S. Appl. No. 15/167,009, filed May 27, 2016.
Office Action (Final) dated Feb. 6, 2018 (53 pages), U.S. Appl. No. 15/167,024, filed May 27, 2016.
Bartlett, Stuart A., et al., "Activation of [CrCl3{R-Sn(H)S-R}] Catalysts for Selective Trimerization of Ethene: A Freeze-Quench Cr K-Edge XAFS Study," ACS Catalysis, Oct. 21, 2014, pp. 4201-4204, vol. 4, No. 11, American Chemical Society.
Bhaduri, Sumit, et al., "Density functional studies on chromium catalyzed ethylene trimerization," Journal of Organometallic Chemistry, Apr. 15, 2009, pp. 1297-1307, vol. 694, Elsevier B. V.
Britovsek, George, J. P.; "A DFT Mechanistic Study on Ethylene Tri- and Tetramerization with Cr/PNP Catalysts: Single versus Double Insertion Pathways," Chemistry A European Journal, Nov. 14, 2016, pp. 16891-16896, vol. 22, No. 47, Wiley-VCH Verlag GmbH & Co. KGaA, Weinheim.
Britovsek, George, J. P.; "Mechanistic study of ethylene tri- and tetramerisation with Cr/PNP catalysts: effects of additional donors," Catalysis Science & Technology, Oct. 28, 2016, pp. 8234-8241, vol. 6, No. 23, Royal Society of Chemistry.
Budzelaar, Peter H.M., "Ethene trimerization at CrI/CrIII—A Density functional theory (DFT) Study," Canadian Journal of Chemistry, 2009, pp. 832-837, vol. 87, Canadian Journal of Chemistry.
Filing receipt and specification for patent application entitled "Carbonyl-Containing Perfluorohydrocarbyl-N2-Phosphinyl Amidine Compounds, Chromium Salt Complexes and Their Use to Oligomerize Ethylene," by Steven M. Bischof, et al., filed Sep. 22, 2017 as U.S. Appl. No. 15/712,295.
Filing receipt and specification for patent application entitled "Perfluorohydrocarbyl-N2-Phosphinyl Amidine compounds, Chromium Salt Complexes, Catalyst Systems, and Their Use to Oligomerize Ethylene," by Steven M. Bischof, et al., filed Sep. 22, 2017 as U.S. Appl. No. 15/712,304.
Filing receipt and specification for patent application entitled "Fluorinated N2-Phosphinyl Amidine Compounds, Chromium Salt Com-

(56) References Cited

OTHER PUBLICATIONS plexes, Catalyst Systems, and Their Use to Oligomerize Ethylene," by Steven M. Bischof, et al., filed Sep. 22, 2017 as U.S. Appl. No. 15/712,307.
Gong, Minglan, et al., "Selective Co-Oligomerization of Ethylene and 1-Hexene by Chromium-PNP Catalysts: A DFT Study," Organometallics, Mar. 29, 2016, pp. 972-981, vol. 35, No. 7, American Chemical Society.
Hossain, Anwar, et al., "Spin-crossover in Chromium-catalyzed Ethylene Trimerization Density Functional Theory Study," Bulletin of the Korean Chemical Society, Sep. 2014, pp. 2835-2838, vol. 35, No. 9, Korea Chemical Society.
Marenich, Aleksandr V., et al., "Universal Solvation Model Based on Solute Electron Density and on a Continuum Model of the Solvent Defined by the Bulk Dielectric Constant and Atomic Surface Tensions," Journal of Physical Chemistry B, Apr. 14, 2009, pp. 6378-6396, vol. 113, No. 18, American Chemical Society.
Qi, Yuan, et al., "Role of 1,2-Dimethoxyethane in the Transformation from Ethylene Polymerization to Trimerization Using Chromium Tris(2-ethylhexanoate)-Based Catalyst System: A DFT Study," Organometallics, Mar. 2, 2010, pp. 1588-1602, vol. 29, No. 7, American Chemical Society.
Van Rensburg, Werner Janse, et al., "A DFT Study toward the Mechanish of Chromium-Catalyzed Ethylene Trimerization," Organometallics, Feb. 17, 2004, pp. 1207-1222, vol. 23, No. 6, American Chemical Society.
Yang, Yun, et al., "Mechanistic DFT Study on Ethylene Trimerization of Chromium Catalysts Supported by a Versatile Pyrrole Ligand System," Organometallics, May 15, 2014, pp. 2599-2607, vol. 33, No. 10, American Chemical Society.
Fawcett, F.S., et al., "Cyanogen Fluoride: Synthesis and Properties," Journal of the American Chemical Society, Jul. 5, 1964, pp. 2576-2579, vol. 86, No. 13, American Chemical Society.
AkzoNobel Product Data Sheet MMAO-3A/Heptane Solutions, 2014, 2 pgs.
AkzoNobel Safety Data Sheet MMAO-3A 7 wt% Al in Heptane, 2016, 17 pgs.
AkzoNobel Product Data Sheet MMAO-20/Heptane Solutions, 2014, 2 pgs.
AkzoNobel Safety Data Sheet MMAO-20 11-30% in Heptane, 2007, 9 pgs.
Kappler, B., et al., "Real-time Monitoring of Ethene/1-hexene Copolymerizations: Determination of Catalyst Activity, Copolymer Composition and Copolymerization Parameters," Polymer, 2003, vol. 44, pp. 6179-6186.
Filing receipt and specification for patent application entitled "Oligomerization Reactions Using Aluminoxanes," by Steven M. Bischof, et al., filed Sep. 28, 2017, 2017 as U.S. Appl. No. 15/719,107.
Office Action (Final) dated Nov. 1, 2017 (40 pages), U.S. Appl. No. 15/166,991, filed May 27, 2017.
Office Action dated Aug. 30, 2017 (28 pages), U.S. Appl. No. 15/167,017, filed May 27, 2016.
Foreign communication from a related counterpart application—International Search Report and Written Opinion, PCT/US2017/032199, dated Aug. 17, 2017, 14 pages.
Foreign communication from a related counterpart application—International Search Report and Written Opinion, PCT/US2017/032191, dated Aug. 14, 2017, 15 pages.
Kuhlmann, S,. et al,. "Chromium catalyzed tetramerization of ethylene in a continuous tube reactor—Proof of concept and kinetic aspects," Journal of Catalysis, 2009, pp. 83-91, vol. 262, No. 1, Elsevier Inc.
Foreign communication from a related counterpart application—International Search Report and Written Opinion, PCT/US2017/033165, dated Aug. 3, 2017, 11 pages.
Foreign communication from a related counterpart application—International Search Report and Written Opinion, PCT/US2017/033168, dated Aug. 3, 2017, 8 pages.

Office Action dated Aug. 2, 2017 (36 pages), U.S. Appl. No. 15/167,024, filed May 27, 2016.
Agapie, Theodor, et al., "Mechanistic Studies of Olefin and Alkyne Trimerization with Chromium Catalysts: Deuterium Labeling and Studies of Regiochemistry Using a Model Chromacyclopentane Complex," J. Am. Chem. Soc., 2007, pp. 14281-14295, vol. 129, No. 46, American Chemical Society.
Bollmann, Annette, et al., "Ethylene Tetramerization: A New Route to Produce 1-Octene in Exceptionally High Selectivities," J. Am. Chem. Soc., 2004, pp. 14712-14713, vol. 126, No. 45, American Chemical Society.
Carter, Anthea, et al., "High activity ethylene trimerisation catalysts based on diphospine ligands," Chemical Communications, vol. 8, 2002, pp. 858-859 plus 2 pages Supplementary Information.
Filing receipt and specification for International application entitled "Olefin Compositions," filed Jul. 14, 2015 as International application No. PCT/US2015/040433.
Filing receipt and specification for patent application entitled, "Reduced Polymer Formation for Selective Ethylene Oligomerizations," by Jared T. Fern, et al., filed May 27, 2016 as U.S. Appl. No. 15/167,009.
Filing receipt and specification for patent application entitled "Process Improvements for Chromium Based Ethylene Oligomerizations," by Steven M. Bischof, et al., filed May 27, 2016 as U.S. Appl. No. 15/167,017.
Filing receipt and specification for patent application entitled "Reduced Polymer Formation for Selective Ethylene Oligomerizations," by Jared T. Fern, et al., filed May 27, 2016 as U.S. Appl. No. 15/617,024.
Group notation revised in periodic table, Feb. 4, 1985, C&EN, pp. 26-27.
McNaught, Alan D., et al., "Compendium of Chemical Terminology," IUPAC Recommendations, Second edition, 1997, 5 pages, Wiley-Blackwell.
Office Action dated Apr. 25, 2017 (21 pages), U.S. Appl. No. 15/166,991, filed May 27, 2016.
Sydora, Orson L., et al., "Selective Ethylene Tri-/Tetramerization Catalysts," ACS Catalysis, 2012, pp. 2452-2455, vol. 2, American Chemical Society.
Filing receipt and specification for patent application entitled, "Process Improvements in Selective Ethylene Oligomerizations," by Steven M. Bischof, et al., filed May 27, 2016 as U.S. Appl. No. 15/166,991.
Office Action dated Jul. 24, 2017 (33 pages), U.S. Appl. No. 15/167,009, filed May 27, 2016.
Office Action dated Sep. 18, 2018 (31 pages), U.S. Appl. No. 15/712,295, filed Sep. 22, 2017.
Office Action dated Oct. 1, 2018 (26 pages), U.S. Appl. No. 15/167,009, filed May 27, 2016.
Foreign communication from a related counterpart application—International Search Report and Written Opinion, PCT/US2018/052709, dated Jan. 11, 2019, 12 pages.
Office Action (Final) dated Jan. 23, 2019 (25 pages), U.S. Appl. No. 15/166,991, filed May 27, 2016.
Office Action (Final) dated Jan. 23, 2019 (16 pages), U.S. Appl. No. 15/719,107, filed Sep. 28, 2017.
Notice of Allowance dated Jan. 29, 2019 (7 pages), U.S. Appl. No. 15/712,295, filed Sep. 22, 2017.
Office Action (Final) dated Feb. 13, 2019 (17 pages), U.S. Appl. No. 15/167,024, filed May 27, 2016.
Notice of Allowance dated Feb. 14, 2019 (9 pages), U.S. Appl. No. 15/167,009, filed May 27, 2016.
Foreign communication from a related counterpart application—International Search Report and Written Opinion, PCT/US2018/036068, dated Feb. 25, 2019, 15 pages.
Advisory Action dated May 1, 2019 (5 pages), U.S. Appl. No. 15/719,107, filed Sep. 28, 2017.
Receipt and Specification of U.S. Appl. No. 16/408,110, filed May 9, 2019, entitled, "Reduced Polymer Formation for Selective Ethylene Oligomerizations," 122 pages.
Notice of Allowance dated May 7, 2019 (8 pages), U.S. Appl. No. 15/167,024, filed May 7, 2019.

(56) References Cited

OTHER PUBLICATIONS

Notice of Allowance dated May 13, 2019 (13 pages), U.S. Appl. No. 15/166,991, filed May 27, 2016.

* cited by examiner

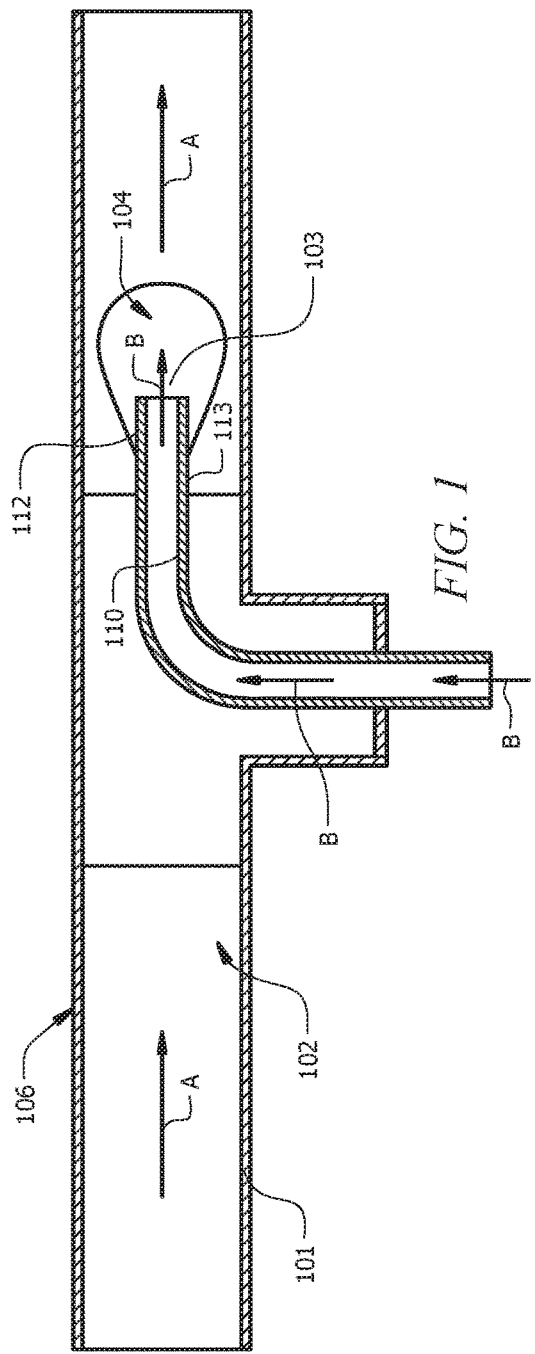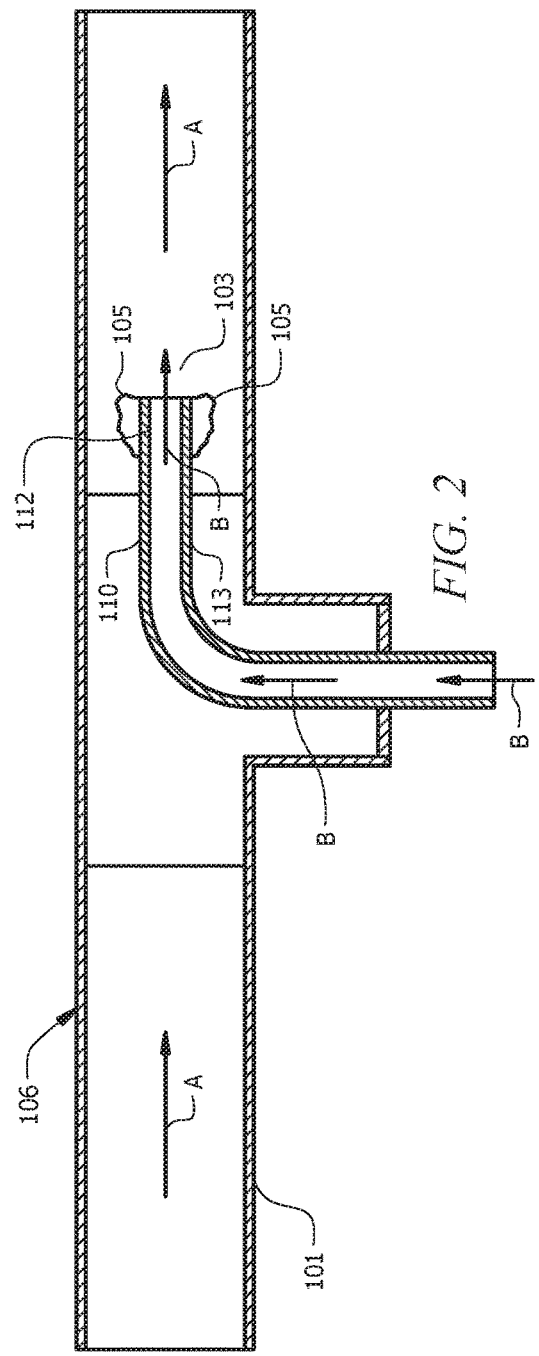

FOULING PROTECTION FOR AN OLIGOMERIZATION REACTOR INLET

REFERENCE TO RELATED APPLICATIONS

This application is a continuation of co-pending U.S. patent application Ser. No. 15/615,113 filed Jun. 6, 2017 and the disclosure of which is incorporated herein by reference in its entirety.

TECHNICAL FIELD

This disclosure relates to the fouling of a reactor inlet of an oligomerization reactor.

BACKGROUND

Oligomerization reactions convert one or more reactants (e.g., ethylene) to one or more products (e.g., 1-hexene). The reactions generally take place in an oligomerization reactor, where the reactant(s) are fed. Reactants generally can react with other components (e.g., other reactants and/or catalyst) upon contact in the reactor. Undesirable byproducts such as polymer can be formed, and in some cases, the byproducts can accumulate as solids which foul part(s) of the reactor. There is an ongoing need to address fouling of oligomerization reactors.

SUMMARY

Disclosed herein is a process to prevent fouling at a reactor inlet, the process comprising flowing a reactant into a reactor via the reactor inlet such that the reactant is introduced to an interior of the reactor via an end of the reactor inlet, and flowing an inert material into the reactor coaxially with respect to an outer surface of the end of the reactor inlet.

Also disclosed herein is a system to prevent fouling of a reactor inlet, the apparatus comprising a reactor, a reactor inlet coupled with the reactor such that an end of the reactor inlet extends into an interior of the reactor, and an inlet sleeve coupled with the reactor such that an end of the inlet sleeve extends into the interior of the reactor, wherein the inlet sleeve is placed coaxially around at least a portion of the reactor inlet such that an annular space is formed between an outer surface of the reactor inlet and an inner surface of the inlet sleeve.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific aspects presented herein.

FIG. 1 illustrates a cross-sectional view of a reactor which can be susceptible to fouling at the end of a reactor inlet.

FIG. 2 illustrates a cross-sectional view of a reactor which can be susceptible to fouling at the end of a reactor inlet.

Figure 3:
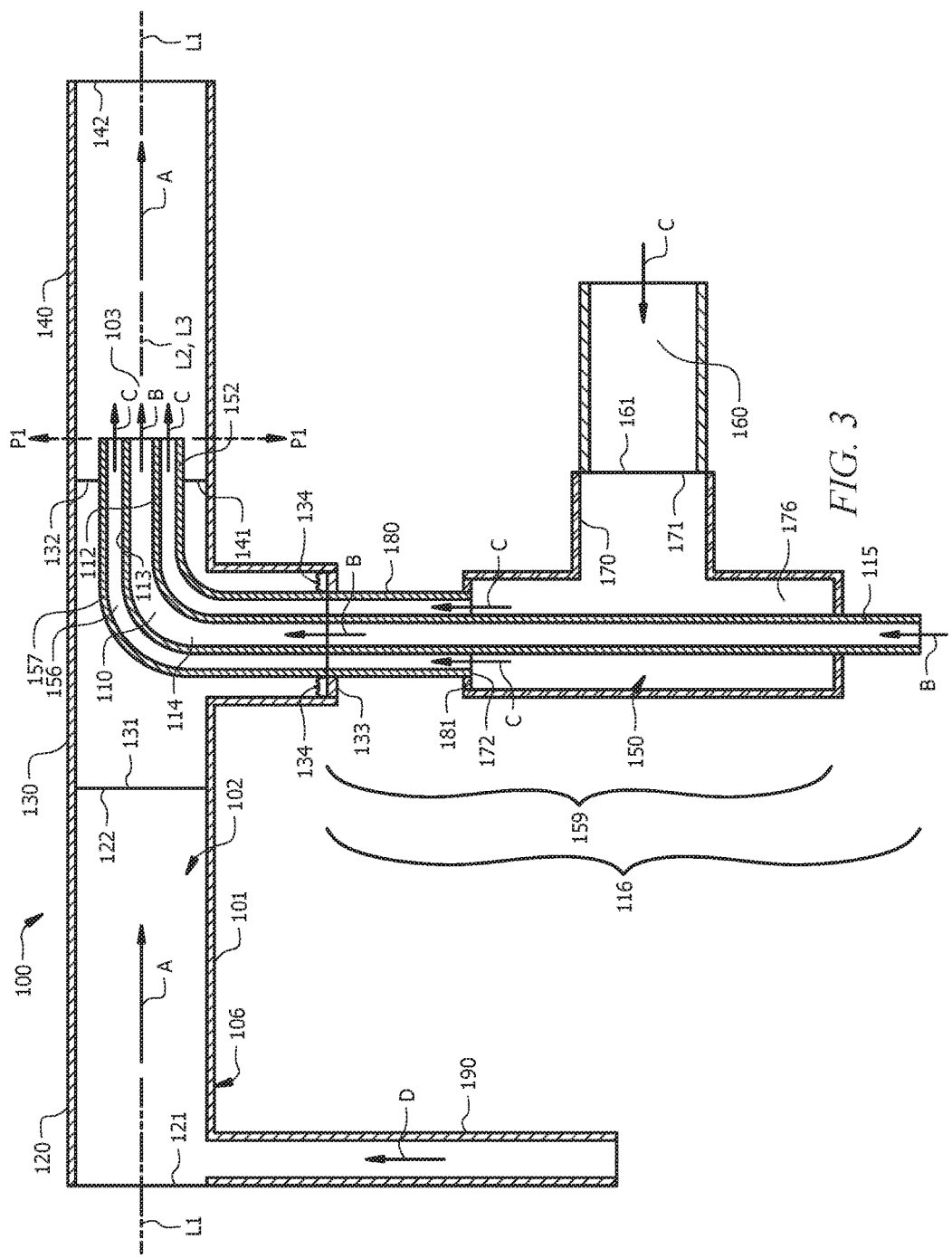
FIG. 3 illustrates a cross-sectional view of a system which can prevent fouling of a reactor inlet.

While the inventions disclosed herein are susceptible to various modifications and alternative forms, only a few specific aspects have been shown by way of example in the drawings and are described in detail below. The figures and detailed descriptions of these specific aspects are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DETAILED DESCRIPTION

The figures described above and the written description of specific structures and functions below are not presented to limit the scope of what Applicants have invented or the scope of the appended claims. Rather, the figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions can require numerous implementation-specific decisions to achieve the developer's ultimate goal for the commercial embodiment. Such implementation-specific decisions can include, and likely are not limited to, compliance with system-related, business-related, government-related and other constraints, which can vary by specific implementation, location, and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the figures and are not intended to limit the scope of the invention or the appended claims.

Within the scope of the system and processes disclosed herein, it is contemplated that various equipment associated with reactor systems (e.g., valves, pumps, accumulators, piping, reboilers, condensers, heaters, compressors, control systems, safety equipment, and the like), while may not be shown for purposes of clarity, can be included in various aspects according to techniques known in the art with the aid of this disclosure.

While the disclosed techniques are described in the context of selective oligomerization, it is contemplated that the inventive subject matter can apply to any process and system which can be susceptible to fouling caused by one or more reactants which results in fouling at a reactor inlet, for example, in olefin polymerization reactions.

Turning now to the figures, FIGS. 1 and 2 illustrate a cross-sectional view of reactor 101 having reactor inlet 110 which can be susceptible to fouling. As can be seen, reactor inlet 110 is placed within interior 102 of reactor 101 (i.e., 106 of reactor 101 shown) such that one or more reactants are fed into interior 102 of reactor 101 via end 112 of inlet 110. In FIGS. 1 and 2, reactants are fed from inlet 110 into reactor 101 in the direction of process flow (arrows A). The direction of flow of reactant(s) within inlet 110 is shown as arrows B.

It has been found that cloud 104 of a reactant fed into reactor 101 via inlet 110 can form at injection point 103. "Injection point" is defined as the location where reactant(s) enters the process flow in interior 102 of reactor 101. Without being limited by theory, it is believed currents in the process flow around reactor inlet 110 can cause cloud 104 to form as reactant(s) is injected into interior 102 of reactor 101. Cloud 104 can be a concentrated volume of reactant(s). For example, in selective oligomerization or trimerization reactions, cloud 104 of a concentrated volume of ethylene monomer can form at injection point 103. Under certain conditions, the concentrated volume of the reactant(s) can react to form a product (or more than one product) which accumulates on and fouls end 112 of the reactor inlet 110.

FIG. 2 illustrates exemplary fouling of reactor inlet 110, which can be an accumulation of undesirable product 105 on outer surface 113 of end 112 of reactor inlet 110. In the context of selective ethylene oligomerization, undesirable product 105 can be ethylene polymer, which is not the target product of the reaction and the formation of which is not desired anywhere in system 100.

The generation and accumulation of undesirable product 105 on reactor inlet 110 can cause various problems. For example, the amount of undesirable product 105 can build to such an amount that reactor 101 must be shut down for cleaning, thus reducing the run time of the desired reaction. For example, the contact of a high concentration of ethylene with a selective ethylene oligomerization catalyst system can make polymer fouling the major limiting factor in oligomer production. Another problem is the accumulation of undesirable product 105 also can cause flow issues within reactor 101. Flow conditions can change (and thus affect reaction conditions) since the process flow collides with and/or flows around the accumulation of undesirable product 105 on reactor inlet 110 (e.g., accumulation of undesirable product may result in increased flow velocity due to the narrowed flow path area). Accumulation of undesirable product 105 can also limit the temperature range in which reactions are operated. For example, in selective ethylene oligomerization, while selective oligomerization reactions can occur at temperatures below the melting point of undesirable product 105 of ethylene polymer, operation at temperatures above the melting point might be desirable to reduce the amount of ethylene polymer which accumulates at end 112 of reactor inlet 110; however, ethylene polymer formation on end 112 of reactor inlet 110 might not be avoided (and thus fouling is not prevented) by operating at temperatures above the melting point of the ethylene polymer.

Figure 4:
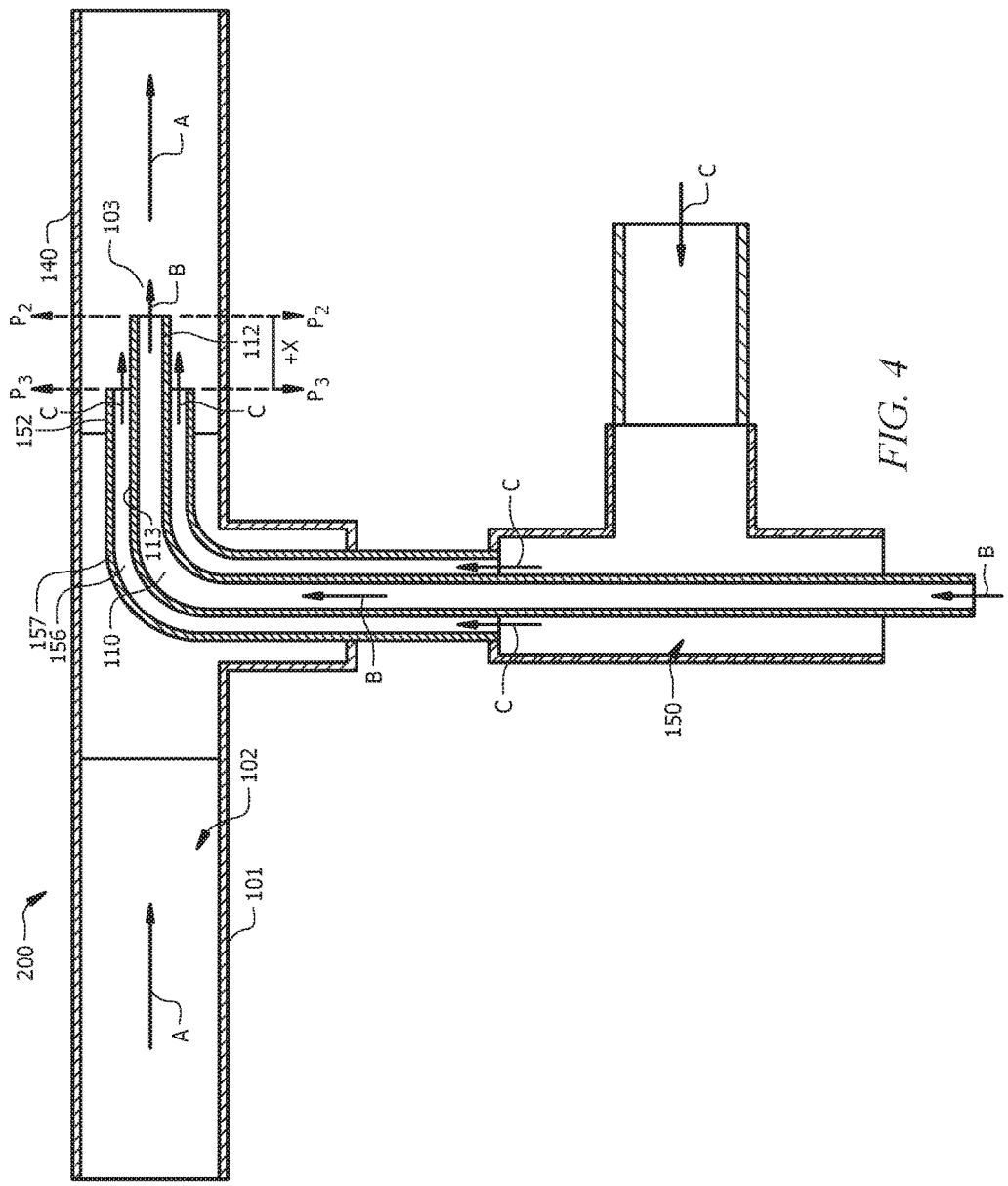
FIG. 4 illustrates a cross-sectional view of another system which can prevent fouling of a reactor inlet.
Figure 5:
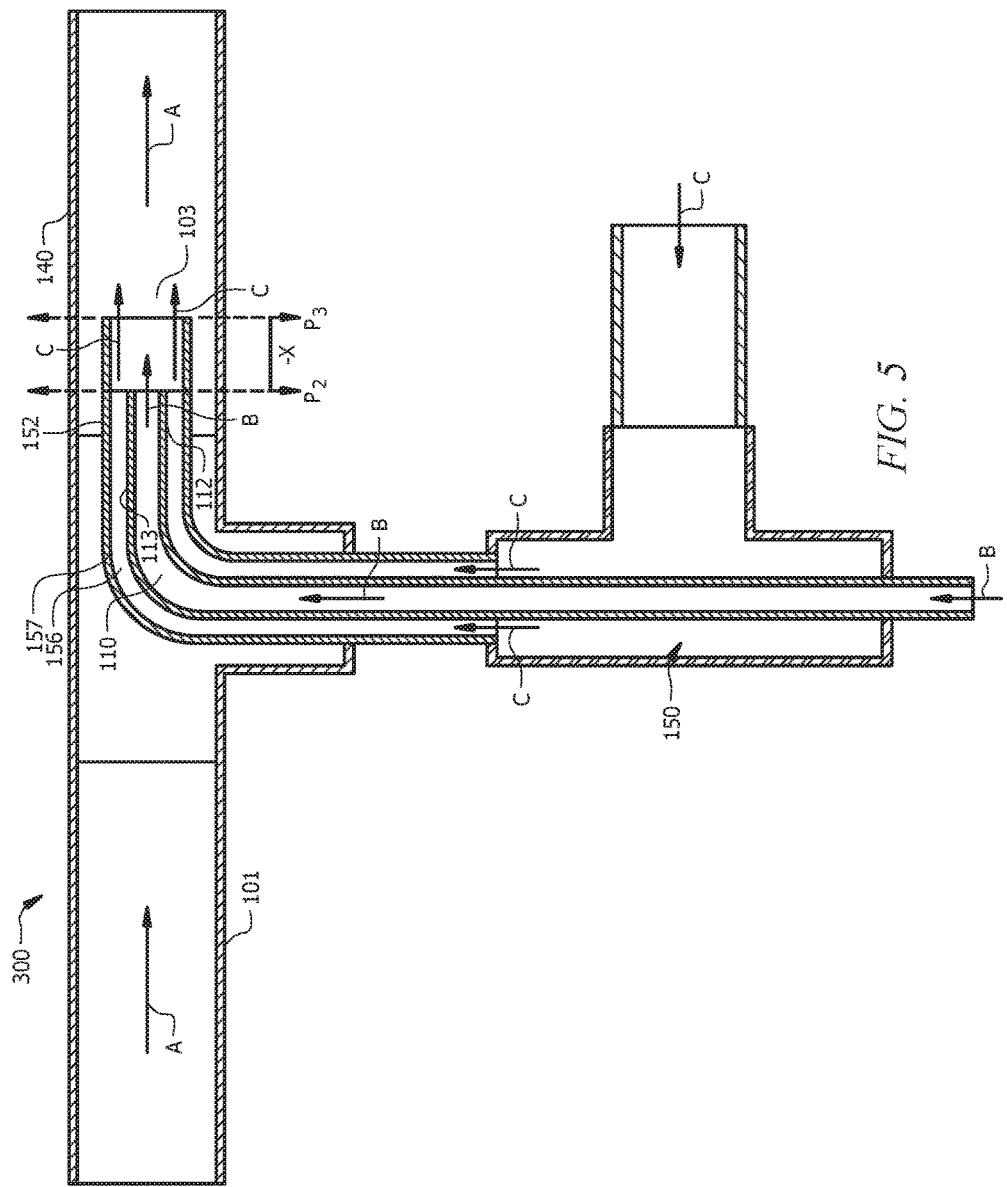
FIG. 5 illustrates a cross-sectional view of another system which can prevent fouling of a reactor inlet.

As such, systems and processes to prevent fouling of reactor inlet 110 are disclosed. Aspects of these systems and processes are shown in FIGS. 3 to 5. The processes of the disclosure are described concurrently with the description of the systems in the figures. The disclosed processes and systems can avoid fouling of reactor inlet 110. The use of inlet sleeve 150 as described herein can create a curtain of inert material around end 112 of reactor inlet 110 such that a concentrated volume of the reactant(s) which is injected by inlet 110 does not accumulate in cloud 104, and thus, does not react to form undesirable product 105 which can accumulate on end 112 of reactor inlet 110.

FIGS. 3 to 5 show systems 100, 200, and 300 where end 112 of reactor inlet 110 and end 152 of inlet sleeve 150 are in the same plane or in parallel planes offset by X or —X, as is described in detail below.

FIG. 3 illustrates a cross-sectional view of system 100 to prevent fouling of reactor inlet 110. System 100 includes reactor 101 (a portion 106 of which is shown), reactor inlet 110 which is coupled with reactor 101 such that end 112 of reactor inlet 110 extends into interior 102 of reactor 101, and inlet sleeve 150 which is coupled with reactor 101 such that end 152 of inlet sleeve 150 extends into interior 102 of reactor 101. System 100 can also include catalyst inlet 190.

Inlet sleeve 150 can be placed coaxially around at least portion 114 of reactor inlet 110 such that annular space 156 is formed between outer surface 113 of reactor inlet 110 and inner surface 157 of inlet sleeve 150. In FIG. 3, inlet sleeve 150 is not placed around another portion 115 of reactor inlet 110. That is, in aspects, at least some portion 115 of reactor inlet 110 is not covered by inlet sleeve 150.

In the embodiment of FIG. 3, end 112 of reactor inlet 110 and end 152 of the inlet sleeve 150 terminate in a common plane P1 in interior 102 of reactor 101. That is, an exit plane of end 152 of inlet sleeve 150 is the same plane P1 as the exit plane of end 112 of reactor inlet 110. Common plane P1 can be perpendicular to the longitudinal axis L1 of portion 106 of reactor 101, the longitudinal axis L2 of reactor inlet 110, the longitudinal axis L3 of inlet sleeve 150, or a combination thereof.

In an aspect, annular space 156 can be formed both inside (in interior 102) and outside of reactor 101. As shown in FIG. 3, annular space 156 is formed inside reactor 101, and also outside reactor 101 for portion 159 of inlet sleeve 150 which extends outside reactor 101 coaxially around reactor inlet 110. It is contemplated that inlet sleeve 150 can have configurations in which annular space 156 is formed only inside reactor 101, and no annular space 156 is formed outside reactor 101.

Annular space 156 is formed because the outer diameter of reactor inlet 110 is less than the inner diameter of inlet sleeve 150. The inner diameter of inlet sleeve 150 can be greater than the outer diameter of reactor inlet 110 by 1, 2, 3, 4, 5, 6, 7, 8, 9, or 10 mm, for example. Small differences between the outer diameter of reactor inlet 110 and the inner diameter of inlet sleeve 150 can increase the flow velocity on the outer surface 113 of end 112 of reactor inlet 110, which can reduce material buildup.

A first material can flow into reactor 101 via reactor inlet 110 such that the first material is introduced to interior 102 of the reactor via end 112 of reactor inlet 110. A second material can flow into reactor 101 coaxially with respect to outer surface 113 of end 112 of reactor inlet 110 via annular space 156, whereby flow of the second material prevents the formation of a concentrated cloud of the first material as shown in FIG. 1. The first material can be a reactant, for example, a first petrochemical. The second material can be a second petrochemical, an inert material, nitrogen, argon, or a combination thereof. The first petrochemical can be any reactant which can cause fouling of a reactor. In some aspects, the first petrochemical can be olefin monomer, olefin comonomer, or a combination thereof. The second petrochemical can be a petrochemical which is inert to the reaction(s) in reactor 101. In some aspects, the second petrochemical can be a diluent with respect to an oligomerization reaction in reactor 101, such as a saturated hydrocarbon (e.g., an alkane). Nonlimiting examples of saturated hydrocarbons include ethane, propane, n-butane, iso-butane, pentane, hexane, heptane, octane, nonane, decane, dodecane, or combinations thereof.

In additional aspects, a diluent can flow into reactor 101 via reactor inlet 110 (in combination with the reactant) such that a mixture of the reactant and the diluent is introduced to interior 102 of the reactor via end 112 of reactor inlet 110. In such aspects, the diluent which flows into reactor 101 via reactor inlet 110 (with the reactant) can be a primary source of diluent for a reaction in reactor 101, and the inert material which flows coaxially into reactor 101 in annular space 156 can be a secondary source of diluent for the reaction in reactor 101. The diluent of the primary source can be the same or different compound (e.g., alkane) from the diluent of the secondary source.

FIG. 3 shows the flow path indicated by arrows C for the inert material in annular space 156 is separate from the flow path indicated by arrows B for the reactant in reactor inlet 110. That is, the inert material which flows into reactor 101 via annular space 156 can flow separately from the reactant, which flows into the reactor via end 112 of reactor inlet 110. Also shown in FIG. 3, end 112 of reactor inlet 110 and end 152 of inlet sleeve 150 can terminate in a common plane P1. Termination in a common plane can be referred to as a "neutral orientation."

Portion 106 of reactor 101 shown in FIG. 3 can have a first section 120, a second section 130 connected to first section 120, and a third section 140 connected to second section 130. First section 120 and third section 140 can each be a tubular member (e.g., a tube or pipe such as a flow-loop reactor). Second section 130 can be a tee connector which has an end 131 connected to an end 122 of first section 120 and an end 132 connected to an end 141 of third section 140. As shown in FIG. 3, first section 120, second section 130, and third section 140 can share the same longitudinal axis L1. That is, portion 106 of reactor 101 shown in FIG. 3 has a longitudinal axis L1. Second section 130 can have another end 133 through which reactor inlet 110 and inlet sleeve 150 extend. End 132 and end 133 of second section 130 can be perpendicular to one another (e.g., forming a "T" configuration). First section 120, second section 130, and third section 140 of reactor 101 can form a continuous flow channel having a constant diameter. Alternatively, the diameter of the continuous flow channel can vary. End 133 of second section 130, as shown in FIG. 3, can be a portion of a tee connector which has a diameter the same as ends 131 and 132 of second section 130. However, it is contemplated that the diameter of end 133 can be different (larger or smaller) than the diameter of ends 131 and 132. In an alternative aspect, one or more of first section 120, second section 130, and third section 140 is embodied by equipment other than tubing or piping (e.g., sections of a reactor vessel). For example, second section 130 can be tubing or piping which is not a tee connector (e.g., a tee connector in a flow-loop reactor), but rather piping extending inward into an interior volume of a reactor vessel having any process required size and shape. For example, reactor inlet 110 and inlet sleeve 150 extend through a hole in the wall of any suitable reactor vessel incorporating one or more reactant inlets of the type described herein that are subject to fouling. In aspects where the diameter of end 133 of the second section 130 is larger than the diameter of inlet sleeve 150, second section 130 of reactor 101 can include a flange or wall 134 on end 133 to prevent process components from escaping from interior 102 of the reactor 101.

Process flow designated by arrows A enters portion 106 of reactor 101 shown in FIG. 3 via end 121 of first section 120, flows from first section 120 through second section 130 and third section 140, and exits via end 142 of third section 140. Components of the process flow can change as the process flow passes through first section 120, second section 130, and third section 140. For example, fresh reactant can be contained in third section 140 but not in first section 120 or second section 130. However, it is contemplated that unreacted reactant can be contained in the process flow in first section 120, for example, in reactor 101 having a loop configuration and/or effluent recycle equipment which injects recycled components upstream of injection point 103.

Reactor 101 in FIG. 3 can be any reactor configured to react a reactant to form a desired product. For example, reactor 101 can comprise an oligomerization reactor which can oligomerize ethylene to an oligomer product (e.g., 1-hexene, 1-octene, decenes, or combinations thereof). In an aspect, reactor 101 of any process and system described herein can comprise a stirred tank reactor, a plug flow reactor, an autoclave reactor, a continuously stirred tank reactor, a loop reactor, a solution reactor, a tubular reactor, a recycle reactor, a bubble reactor, or any combination thereof. In an aspect, reactor 101 is a stirred tank reactor; alternatively, a plug flow reactor; alternatively, an autoclave reactor; alternatively, a continuously stirred tank reactor; alternatively, a loop reactor; alternatively, a solution reactor; alternatively, a tubular reactor; alternatively, a recycle reactor; or alternatively, a bubble reactor. In some aspects, reactor 101 can be one of multiple reactors; or alternatively, only a single reactor. When multiple reactors are present, each of the reactors can be the same or different types of reactors, and may include one or more of reactors 101 as described herein having system 100 to prevent fouling therein. In aspects, reactor 101 can comprise a single reactor or be one of multiple reactors of any of the types disclosed herein operating in batch or continuous mode; or alternatively, in continuous mode.

The configuration of reactor 101 is not limited to reaction conditions or reactants. The pressure and temperature are limited only by those values known by those skilled in the art for a particular reaction.

For selective ethylene oligomerization, conditions under which the oligomer product can be formed (or alternatively, reactor 101 can have conditions) that can include one or more of catalyst system component ratios, chromium concentration, pressure, ethylene partial pressure, ethylene concentration, presence of hydrogen (and its partial pressure and/or hydrogen to ethylene weight ratio), temperature, reaction time, single pass ethylene conversion, and catalyst system productivity.

Exemplary values for the aluminum to chromium molar ratio can range from 10:1 to 5,000:1, from 50:1 to 3,000:1, from 50:1 to 1,000:1, from 75:1 to 2,000:1, from 100:1 to 2,000:1, of from 100:1 to 1,000:1.

Exemplary concentrations of chromium can range from $1 \times 10^{-6}$ Cr equivalents/liter to 1 Cr equivalents/liter, from $1 \times 10^{-5}$ Cr equivalents/liter to $5 \times 10^{-1}$ Cr equivalents/liter, from $5 \times 10^{-4}$ Cr equivalents/liter to $1 \times 10^{-1}$ Cr equivalents/liter. Other chromium concentration ranges that can be utilized are readily apparent to those skilled in the art with the aid of this disclosure.

Exemplary pressures can include a pressure from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 250 psi (1.72 MPa) to 1000 psig (6.89 MPa), or from 600 psi (4.1 MPa) to 1400 psi (9.65 MPa). Other pressure ranges that can be utilized for selective ethylene oligomerization which are readily apparent to those skilled in the art with the aid of this disclosure.

Exemplary ethylene partial pressure range from 5 psi (34.5 kPa) to 2,500 psi (17.2 MPa), from 5 psi (34.5 kPa) to 2,000 psi (13.8 MPa), from 50 psi (345 kPa) to 2,000 psi (13.8 MPa), from 100 psi (689 kPa) to 2,000 psi (13.8 MPa), from 100 psi (689 kPa) to 1,500 psi (10.3 MPa), from 500 psi (3.5 MPa) to 1500 psi (10.3 MPa), from 150 psi (1.03 MPa) to 1250 psi (8.62 MPa), from 150 psi (1.03 MPa) to 1250 psi (8.62 MPa), or from 250 psi (1.72 MPa) to 1000 psi (6.89 MPa). Other ethylene partial pressure ranges are readily apparent to those skilled in the art with the aid of this disclosure.

Exemplary ethylene concentrations can range from 4 mass % to 70 mass %, from 4 mass % to 60 mass %, from 10 mass % to 60 mass %, from 25 mass % to 55 mass %, 35 mass % to 50 mass %, or 40 mass % to 48 mass % based upon the total mass in the reactor. Other ethylene concentration ranges that can be utilized are readily apparent to those skilled in the art with the aid of this disclosure.

Exemplary ethylene to chromium mass ratio can range from 50,000:1 to 5,000,000:1, 150,000:1 to 2,500,000:1, 250,000:1 to 1,500,000:1, or 400,000:1 to 1,000,000:1. Other ethylene:chromium mass ratio ranges that can be utilized are readily apparent to those skilled in the art with the aid of this disclosure.

Exemplary hydrogen partial pressures can range from 1 psi (6.9 kPa) to 200 psi (1.4 MPa), from 5 psi (34 kPa) to 150 psi (1.03 MPa), from 10 psi (69 kPa) to 100 psi (689 kPa), or from 15 psi (100 kPa) to 75 psig (517 kPa). Other hydrogen partial pressure ranges that can be utilized are readily apparent to those skilled in the art with the aid of this disclosure.

Exemplary hydrogen to ethylene mass ratios can range from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other hydrogen to ethylene mass ratio ranges that can be utilized are readily apparent to those skilled in the art with the aid of this disclosure.

Exemplary hydrogen to chromium mass ratios can range from 1:1 to 100,000:1, 50:1 to 50,000:1, 100:1 to 10,000:1, or 200:1 to 3,000:1. Other hydrogen:chromium mass ratio ranges that can be utilized are readily apparent to those skilled in the art with the aid of this disclosure.

Exemplary temperatures can include a temperature from 0° C. to 200° C., from 25° C. to 150° C., from 25° C. to 130° C., from 40° C. to 100° C., from 50° C. to 100° C., or from 50° C. to 90° C. Other temperature ranges that can be utilized for selective ethylene oligomerization which are readily apparent to those skilled in the art with the aid of this disclosure.

Exemplary reaction times (or residence times) can range from 1 minute to 5 hours; alternatively, ranges from 5 minutes to 2.5 hours; alternatively, ranges from 10 minutes to 2 hours; or alternatively, ranges from 15 minutes to 1.5 hours. In some aspects (in continuous process embodiments), the reaction time (or residence time) can be stated as an average reaction time (or average residence time) and can range from 1 minute to 5 hours; alternatively, ranges from 5 minutes to 2.5 hours; alternatively, ranges from 10 minutes to 2 hours; or alternatively, ranges from 15 minutes to 1.5 hours.

Exemplary ethylene conversions can be at least 30%, 35%, 40%, or 45%.

Exemplary values for catalyst system productivity can be greater than 10,000, 50,000, 100,000, 150,000, 200,000, 300,000, or 400,000 grams (hexenes plus octenes, also designated as $C_6+C_8$) per gram of chromium.

Selective ethylene oligomerization can occur in an environment having any combination of the above conditions.

For ethylene oligomerization, conditions under which the oligomer product can be formed (or alternatively, reactor 101 can have conditions) that can include one or more of pressure, temperature, flow rate, mechanical agitation, product takeoff, residence time, and concentrations. Any combination of these conditions may be selected to achieve the desired oligomer properties. Conditions that are controlled for oligomerization efficiency and to provide desired product properties may include temperature, pressure, and the concentrations of various reactants. Oligomerization temperature can affect catalyst activity, molecular weight of the polyolefin, and molecular weight distribution of the polyolefin.

As depicted in FIGS. 2-5, reactor inlet 110 can be appropriate tubing or piping coupled with reactor 101 which delivers the reactant(s) to interior 102 of reactor 101. In an aspect, reactor inlet 110 can be a diptube. Reactor inlet 110 in FIG. 3 has an L-shape with a 90-degree bend on portion 114 which is placed in interior 102 of reactor 101, in the second section 130. A portion 116 of the reactor inlet 110 can extend outside the reactor 101 and receive flow of a first material (e.g., a reactant such as ethylene) in the direction of arrows B. It is contemplated that the reactor inlet 110 can have other configurations appropriate for the design of the reactor 101 and reaction involved. For example, the reactor inlet 110 can be located in a bend of the reactor 101, and the configuration of the reactor inlet 110 at this location can be straight.

The reactor inlet 110 in FIG. 3 can be placed in second section 130 such that end 112 of reactor inlet 110 extends into third section 140. A portion 116 of reactor inlet 110 extends outside second section 130 in a direction about perpendicular to the longitudinal axis L2 of end 112 of reactor inlet 110. Moreover, the longitudinal axis L2 of end 112 of reactor inlet 110 can be parallel to, or as shown in FIG. 3, can be the same as, longitudinal axis L1 of portion 106 of reactor 101.

Inlet sleeve 150 can be appropriate tubing or piping which coaxially surrounds at least a portion of reactor inlet 110 and thereby forms an annular space between at least a portion of reactor inlet 110 and inlet sleeve 150. FIG. 3 shows inlet sleeve 150 can have a first section 160, a second section 170, and a third section 180. End 161 of first section 160 can be connected to an end 171 of second section 170. Another end 172 of second section 170 can be connected to an end 181 of third section 180. First section 160 and third section 180 can be embodied as tubing or piping, and second section 170 can be a tee connector for connecting the tubing or piping of first section 160 and third section 180.

End 152 of inlet sleeve 150 can have a longitudinal axis L3. The longitudinal axis L3 of end 152 of inlet sleeve 150 can be the same as the longitudinal axis L2 of the end 112 of inlet 110. Moreover, the longitudinal axis L3 of end 152 of inlet sleeve 150 can be parallel to, or as shown in FIG. 3, can be the same as, longitudinal axis L1 of portion 106 of reactor 101.

End 161 of first section 160 can receive flow of a second material (e.g., an inert material) in the direction of arrows C. The inert material can flow through first section 160, into second section 170, and then into third section 180 before exiting inlet sleeve 150 into interior 102 of reactor 101 at injection point 103. As shown in FIG. 3, the flow path indicated as arrows C for the inert material in annular space 156 can involve two 90-degree turns before the inert material arrives at injection point 103. The first 90-degree turn can be in second section 170 of inlet sleeve 150, and the second 90-degree turn can be in third section 180 of inlet sleeve 150.

Without being limited by theory, it is believed the inert material which flows from annular space 156 into interior 102 of reactor 101 at the injection point 103 can prevent cloud 104 of reactant from forming on end 112 of reactor inlet 110, and thus can prevent the accumulation of undesired product 105 on end 112 of reactor inlet 110, due to a curtain of the inert material which exists over outer surface 113 of end 112 of reactor inlet 110. The flow of the inert material into reactor 101 at injection point 103 can mix with the reactant to likewise prevent cloud 104 of reactant forming on end 152 of inlet sleeve 150, and thus can prevent accumulation of undesired product 105 on end 152 of inlet sleeve 150. The flow of the inert material into reactor 101 at injection point 103 can further provide a turbulent region (e.g., a region with turbulent, non-laminar flow adjacent to end of 112 of reactor inlet 110) to likewise prevent cloud 104 of reactant forming on end 152 of inlet sleeve 150, and thus can prevent accumulation of undesired product 105 on end 152 of inlet sleeve 150.

The flow of the inert material in annular space 156 can be continuous or intermittent. In continuous flow, the inert material can continuously sweep the outer surface 113 of end 112 of reactor inlet 110 such that accumulation of undesired product 105 does not occur. In intermittent flow, the flow of the inert material can transition between flow modes (e.g., no flow and continuous flow) to periodically sweep away any accumulated undesired product 105 from outer surface 113 of end 112 of rector inlet 110 and/or to periodically disrupt cloud formation.

In aspects, the inert material which flows in annular space 156 is substantially free of the catalyst system. By "substantially free of the catalyst system" it is meant that the inert material has equal to or less than 1.0, 0.9, 0.8, 0.7, 0.6, 0.5, 0.4, 0.3, 0.2, or 0.1 wt. % of the catalyst system. In additional or alternative aspects, the inert material which flows in annular space 156 is substantially free of any reactant. By "substantially free of any reactant" it is meant that the inert material has equal to or less than 1.0, 0.9, 0.8, 0.7, 0.6, 0.5, 0.4, 0.3, 0.2, or 0.1 wt. % of any reactant.

A catalyst system can be fed to reactor 101 via catalyst inlet 190. Catalyst inlet 190 can be appropriate tubing or piping which can deliver the catalyst system to reactor 101. The direction of flow of the catalyst system is shown by arrow D. Catalyst inlet 190 is shown in FIG. 3 as feeding catalyst system to interior 102 of portion 106 of reactor 101 upstream (with regard to process flow of arrows A) of injection point 103 for the reactant. It is contemplated that catalyst inlet 190 can be located in another portion of reactor 101 either upstream and/or downstream of injection point 103. Alternatively, it is contemplated the catalyst system can be fed to reactor 101 via reactor inlet 110 in a mixture with the reactant, a diluent, or both the reactant and diluent.

FIG. 4 illustrates a cross-sectional view of another system 200 which prevents fouling of reactor inlet 110. System 200 is the same as system 100, except as described below.

The configuration of end 112 of reactor inlet 110 relative to end 152 of inlet sleeve 152 in system 200 is different than system 100. As can be seen, end 112 of inlet sleeve 110 can extend outside of inlet sleeve 150. An exit plane P2 of end 112 of reactor inlet 110 can be spaced apart in a positive orientation with respect to an exit plane P3 of end 152 of inlet sleeve 150. By "positive orientation" it is meant that end 112 of reactor inlet 110 can extend outside of inlet sleeve 150 and the distance between end 112 of reactor inlet 110 and end 152 of inlet sleeve 150 is a value of X, which is greater than 0 mm.

The symbol "+X" in FIG. 4 indicates the positive orientation between end 112 of reactor inlet 110 and end 152 of inlet sleeve 150 by distance X. Exemplary values for the distance X in positive orientation are greater than 0 mm and less than about 400 mm; alternatively, greater than 0 mm and less than about 300 mm; alternatively, greater than 0 mm and less than about 200 mm; alternatively, greater than 0 mm and less than about 100 mm; alternatively, greater than 0 mm and less than about 50 mm; alternatively, greater than 0 mm and less than about 40 mm; alternatively, greater than 0 mm and less than about 30 mm; alternatively, greater than 0 mm and less than about 20 mm; alternatively, greater than 0 mm and less than about 10 mm. In an aspect, +X is about 5, 10, 15, 20, 25, 30, 35, 40, 45, 50, 55, 60, 65, 70, 75, 80, 85, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mm.

FIG. 4 shows end 112 of reactor inlet 110 in FIG. 4 can be longer than end 112 of reactor inlet 110 of FIG. 3 by distance X. Likewise, injection point 103 can be moved as shown in FIG. 4, relative to the location shown in FIG. 3, by the distance X. Thus, 100 in FIG. 3 can be modified to the embodiment shown in system 200 of FIG. 4 by lengthening end 112 of reactor inlet 110 and moving injection point 103 further into third section 140 of reactor 101 by distance X.

A second material (e.g., an inert material) in system 200 can flow from annular space 156 into interior 102 of reactor 101 along outer surface 113 of end 112 of reactor inlet 110. It is believed the velocity of the inert material exiting end 152 of inlet sleeve 150 in FIG. 4 can maintain a layer of inert material (continuously or intermittently, as the operating mode may be) on outer surface 113 of end 112 of reactor inlet 110, and this layer can provide the curtain of inert material which can prevent cloud 104 of reactant (as seen in FIG. 1) from forming at end 112 of the reactor inlet 110. Mixing of the inert material with the reactant at injection point 103 can contribute to preventing formation of cloud 104 at end 112 of reactor inlet 110. The flow of the inert material along outer surface 113 of end 112 of reactor inlet 110 can likewise prevent cloud 104 of reactant from forming at end 152 of inlet sleeve 150. The distance X between end 152 of the inlet sleeve 150 and end 112 of reactor inlet 110, and mixing of the reactant with the inert material at injection point 103 can contribute to preventing formation of cloud 104 at end 152 of inlet sleeve 150.

Preventing cloud 104 (as seen in FIG. 1) of reactant from forming in system 200 can prevent the accumulation of undesired product 105 (as seen in FIG. 2) on end 112 of reactor inlet 110 and also on end 152 of inlet sleeve 150.

While the inert material curtain formed by inlet sleeve 150 configuration in FIG. 3 is contained within end 152 of inlet sleeve 150, at least a portion of the curtain of inert material formed by the moving inert material in the direction of arrow C on outer surface 113 of end 112 of reactor inlet 110 is not contained within inlet sleeve 150.

The relative dimensions for inlet sleeve 150 and reactor inlet 110 discussed for the embodiment shown in FIG. 4 are exemplary only, and other modifications to the lengths can be made one or both of inlet sleeve 150 and reactor inlet 110 to achieve the positive orientation shown in FIG. 4.

FIG. 5 illustrates a cross-sectional view alternative system 300 which can prevent fouling of reactor inlet 110. The system 300 is the same as system 100 and system 200, except as described below.

The configuration of end 112 of reactor inlet 110 relative to end 152 of inlet sleeve 150 in system 300 is different than both system 100 and system 200. As can be seen, end 112 of reactor inlet 110 can extend inside of inlet sleeve 150 such that an exit plane P2 of end 112 of reactor inlet 110 can be spaced apart in a negative orientation with respect to an exit plane P3 of end 152 of inlet sleeve 150. By "negative orientation" it is meant that end 112 of reactor inlet 110 is contained within inlet sleeve 150 and the distance between end 112 of reactor inlet 110 and end 152 of inlet sleeve 150 is a value of X, which is greater than 0 mm.

The symbol "−X" in FIG. 5 indicates the negative orientation between end 112 of reactor inlet 110 and end 152 of inlet sleeve 150 by distance X. Exemplary values for the distance X in negative orientation are greater than 0 mm and less than about 1,000 mm; alternatively, greater than 0 mm and less than about 900 mm; alternatively, greater than 0 mm and less than about 800 mm; alternatively, greater than 0 mm and less than about 700 mm; alternatively, greater than 0 mm and less than about 700 mm; alternatively, greater than 0 mm and less than about 600 mm; alternatively, greater than 0 mm and less than about 500 mm; alternatively, greater than 0 mm and less than about 400 mm; alternatively, greater than 0 mm and less than about 300 mm; alternatively, greater than 0 mm and less than about 200 mm; alternatively, greater than 0 mm and less than about 100 mm; alternatively, greater than 0 mm and less than about 50 mm; alternatively, greater than 0 mm and less than about 40 mm; alternatively, greater than 0 mm and less than about 30 mm; alternatively, greater than 0 mm and less than about 20 mm; alternatively, greater than 0 mm and less than about 10 mm. In an aspect, −X is about 1, 2, 3, 4, 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 450, 500, 550, 600, 650, 700, 750, 800, 850, 900, 950, or 1000 mm.

FIG. 5 shows end 152 of inlet sleeve 150 in FIG. 5 can be longer than end 112 of reactor inlet 110 of FIG. 3 by distance X. Likewise, injection point 103 can be moved as shown in FIG. 5, relative to the location shown in FIG. 3, by the distance X. Thus, system 100 in FIG. 3 can be modified to the embodiment shown in system 300 of FIG. 5 by lengthening end 152 of inlet sleeve 150 and moving injection point 103 further into third section 140 of reactor 101 by distance X.

FIG. 5 shows end 112 of reactor inlet 110 can terminate inside inlet sleeve 150. End 112 of reactor inlet 110 is thus completely enclosed by inlet sleeve 150, and such a configuration can prevent formation of cloud 104 (as seen in FIG. 1) of reactant at end 112 of reactor inlet 110. It is believed the velocity of the inert material flowing along inner surface 157 of inlet sleeve 150 in FIG. 5 can maintain a layer of inert material (continuously or intermittently, as the operating mode may be) on inner surface 157 of end 152 of inlet sleeve 150. This layer can surround the reactant as the reactant continues to flow within end 152 of inlet sleeve 150 to injection point 103. This layer of inert material can mix with the reactant within end 152 of inlet sleeve 150 and/or at injection point 103. The mixing in these locations of system 300 can prevent cloud 104 of reactant from forming at end 152 of inlet sleeve 150 and/or at injection point 103.

Preventing cloud 104 of reactant from forming in system 300 can prevent the accumulation of undesired product 105 (as seen in FIG. 2) on end 112 of reactor inlet 110 and/or on end 152 of inlet sleeve 150.

The relative dimensions for inlet sleeve 150 and reactor inlet 110 discussed for the embodiment shown in FIG. 5 are exemplary only, and other modifications to the lengths can be made one or both of inlet sleeve 150 and reactor inlet 110 to achieve the negative orientation shown in FIG. 5.

Figure 6:
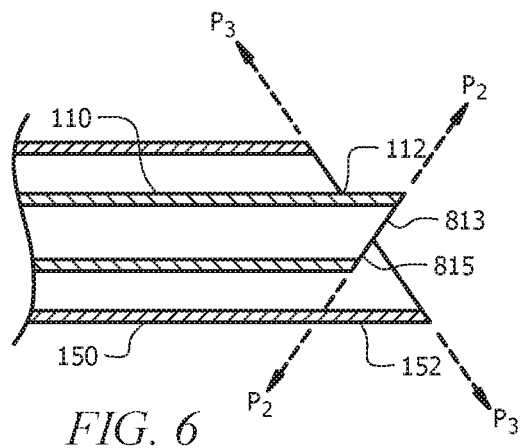
FIGS. 6 to 8 illustrate cross-sectional views of alternative configurations for the exit planes of the inlet sleeve and reactor inlet.
Figure 7:
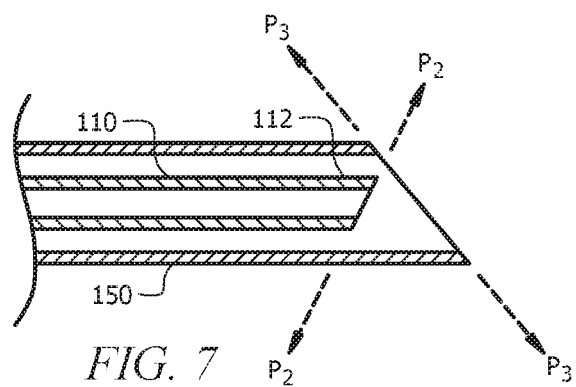
Figure 8:
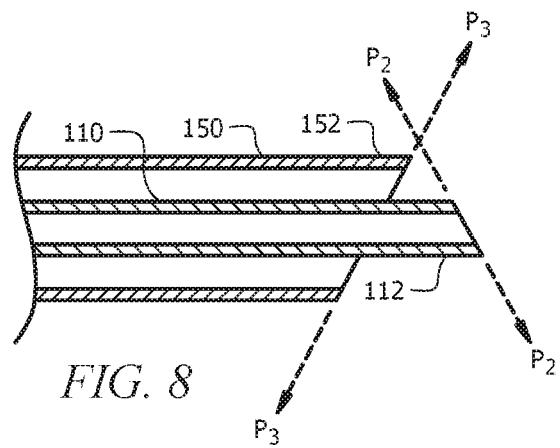

FIGS. 6 to 8 illustrate cross-sectional views of alternative configurations for the exit planes of the inlet sleeve and reactor inlet. FIGS. 6 to 8 show the exit planes P2 and P3 can be other than parallel to one another. In FIG. 6, the exit plane P2 of reactor inlet 110 intersects the exit plane P3 of inlet sleeve 150. First portion 813 of end 112 of reactor inlet 110 extends outside of end 152 of inlet sleeve 150, and second portion 815 of reactor inlet 110 is contained within end 152 of inlet sleeve 150. In FIG. 7, the exit plane P2 of reactor inlet 110 intersects the exit plane P3 of inlet sleeve 150. End 112 of reactor inlet 110 is contained entirely within inlet sleeve 150. In FIG. 8, the exit plane P2 of reactor inlet 110 intersects the exit plane P3 of inlet sleeve 150. End 112 of reactor inlet 110 extends outside end 152 of inlet sleeve 150. The angle of intersection of the exit planes P2 and P3 in FIGS. 6 to 8 can be any angle and is not limited to what is specified in this disclosure.

Figure 9:
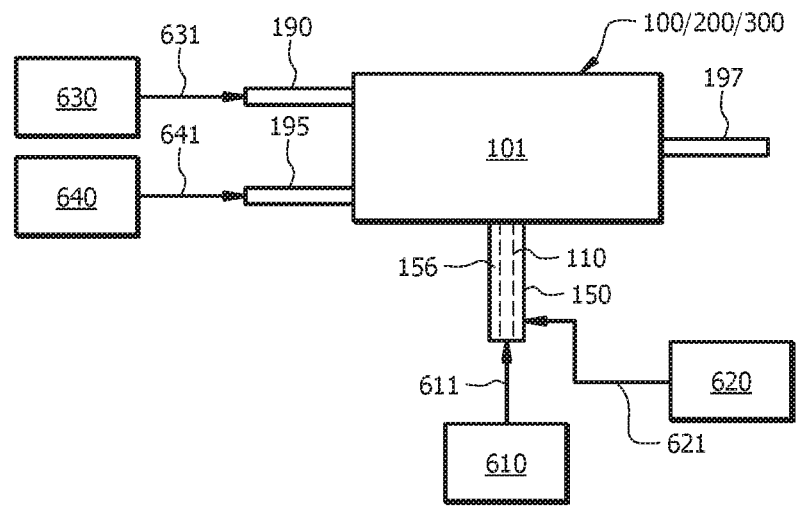
FIG. 9 illustrates the system of FIG. 3, 4, or 5 coupled to various material sources.

FIG. 9 illustrates system 100, 200, or 300 depicted in FIGS. 3, 4, and 5 can be coupled to various material sources. Any one of system 100/200/300 of FIGS. 3 to 5 can be coupled to one or more of a reactant source 610, an inert material source 620, a catalyst system source 630, and a diluent source 640. Reactant source 610 can provide a reactant (or more than one reactant, such as monomer and comonomer) to reactor 101 via reactor inlet 110 (shown with dashed lines in FIG. 9). The reactant can flow to reactor 101 through reactant feed line 611 which is fluidly connected to reactor inlet 110. Inert material source 620 can provide an inert material to reactor 101 via annular space 156 formed between inlet sleeve 150 and reactor inlet 110. The inert material can flow to reactor 101 through inert material feed line 621 which is fluidly connected to annular space 156. Catalyst system source 630 can provide a catalyst system to reactor 101. Catalyst system can flow to reactor 101 through catalyst system feed line 631 which is fluidly connected to catalyst system inlet 190. Diluent source 640 can provide a diluent for the reaction to reactor 101 through a diluent feed line 641 which is fluidly connected to diluent inlet 195.

A reactor effluent flows from reactor 101 via reactor outlet 197. It is contemplated that reactor 101 in each system 100/200/300 described above has reactor outlet 197. The reactor effluent can contain reaction product (the desired product of the reaction), unreacted reactants, inert and/or reactive gases, spent and/or unspent catalyst, or combinations thereof. In the context of selective ethylene oligomerization, the reaction product can include oligomers (e.g., 1-hexene, 1-octene, or both), diluent (e.g., isobutane), unreacted ethylene, components from the catalyst system, the inert material, or combinations thereof. The catalyst system can be injected via catalyst system inlet 190, diluent can be injected via diluent inlet 195, the reactant can be inject via reactor inlet 110, and inert material can be injected via annular space 156 of inlet sleeve 150. Catalyst system and diluent can mix in reactor 101 before the reactant (e.g., ethylene) contacts the catalyst system. Moreover, the reactant and the inert material (e.g., which can be the same as the diluent) can mix within reactor 101 before the reactant contacts the catalyst system. The desired product (e.g., oligomer, polyethylene) can be formed while preventing fouling of reactor inlet 110 via inclusion of one or more of systems 100/200/300. An effluent is removed from reactor 101 via reactor outlet 197.

Reactant source 610 can include any source of the reactant fed to reactor 101, for example a first petrochemical. In an aspect, reactant source 610 can be an ethylene source. Ethylene for any of the processes and systems described herein can be oligomerization grade ethylene. By "oligomerization grade ethylene" it is meant that ethylene can be present in reactant feed line 611 in an amount of at least 98.0, 98.5, 99.0, 99.1, 99.2, 99.3, 99.4, 99.5, 99.6, 99.7, 99.8, 99.9, 99.99, 99.999 mol % based on the total moles of components in the ethylene composition (e.g., in the reactant feed line 611). Reactant source 610 can be physically embodied, for example, as a storage tank or a line from a process which provides the reactant. In the case of ethylene as the reactant, the line can be from any source such as, for example, a cracking process, a monomer recovery process, an ethylene purification process, and the like.

Inert material source 620 can be any source of inert material which is inert to the reaction(s) in the reactor 101. The inert material can include nitrogen, argon, a second petrochemical, or a combination thereof. Nitrogen and argon can be available gases which are commonly used and available in plants for the chemicals and plastics industry. The second petrochemical can be a petrochemical which is inert to the reaction(s) in reactor 101. In some aspects, the second petrochemical can be a diluent with respect to an oligomerization reaction in reactor 101, such as a saturated hydrocarbon or alkane. Nonlimiting examples of saturated hydrocarbons include ethane, propane, n-butane, iso-butane, pentane, hexane, heptane, octane, nonane, decane, dodecane, or combinations thereof. In aspects where the inert material is a diluent, inert material source 620 can be a secondary source (in terms of the materials needed for the reaction in reactor 101) of the diluent, where the primary source for the diluent is diluent source 640. In aspects where the inert material is a diluent, a single or common diluent source (i.e., 620 or 640) may be used as the source of diluent feeding both diluent feed lines 621 and 641. Inert material source 620 can be physically embodied, for example, as a storage tank or a line from a process which provides the diluent. In the case of ethylene oligomerization, line 641 can be from a monomer recovery process which also recovers the diluent.

In an aspect, inert material source 620 can be also diluent source 640, and both inert material line 621 and diluent feed line 641 can be fluidly connected to inert material source 620.

Catalyst system source 630 can be any source of oligomerization catalyst for the reaction in reactor 101. The catalyst system can be mixed with a solvent and/or the diluent prior to being fed to reactor 101. While the disclosure is not limited to a particular oligomerization catalyst, specific embodiments of suitable oligomerization catalyst are discussed in detail below after the description of the figures.

Catalyst system source 630 can be physically embodied, for example, as a storage tank, a mixing device for mixing catalyst system components prior to injection into reactor 101, or both.

Diluent source 640 can be any source of diluent. The diluent is inert to the reaction(s) in reactor 101. With respect to an oligomerization reaction in reactor 101, the diluent can be a saturated hydrocarbon or alkane. Nonlimiting examples of saturated hydrocarbons include ethane, propane, n-butane, iso-butane, pentane, hexane, heptane, octane, nonane, decane, dodecane, or combinations thereof. Diluent source 640 can be the primary source for the diluent for the reaction in reactor 101. Diluent source 640 can be physically embodied, for example, as a storage tank or a line from a process which provides the diluent. In the case of ethylene oligomerization, the line can be from a monomer recovery process which also recovers the diluent.

In an aspect, diluent source 640 also can be inert material source 620, and both inert material line 621 and diluent feed line 641 can be fluidly connected to diluent source 640.

Figure 10:
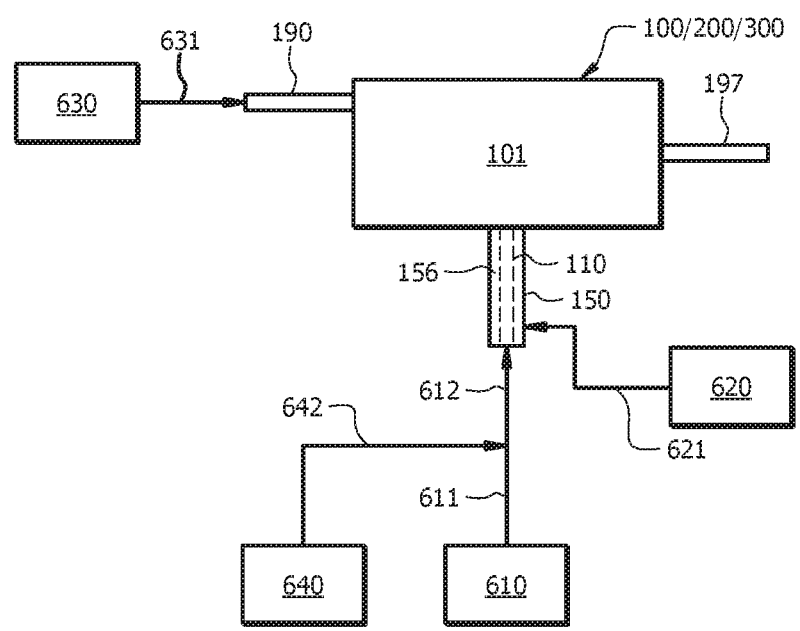
FIG. 10 illustrates an alternative configuration to that shown in FIG. 9.

FIG. 10 illustrates an alternative configuration to that shown in FIG. 9. Any one of system 100/200/300 of FIGS. 3 to 5 can be coupled to one or more of reactant source 610, inert material source 620, catalyst system source 630, and diluent source 640. FIG. 10 shows the diluent can flow from diluent source 640 via diluent feed line 642 and can combine with the reactant from reactant feed line 611 to form combined feed line 612. Combined feed line 612 can feed the mixture of diluent and reactant to reactor 101 via reactor inlet 110 (shown with dashed lines in FIG. 10).

Catalyst system can flow to reactor 101 through catalyst system feed line 631 which is fluidly connected to catalyst system inlet 190. Diluent and reactant can be injected via reactor inlet 110, and inert material source 620 can provide an inert material to reactor 101 via annular space 156 formed between inlet sleeve 150 and reactor inlet 110. The inert material can flow to reactor 101 through inert material feed line 621 which is fluidly connected to annular space 156. The reactant (e.g., ethylene) and the diluent can mix in line 612 before being injected to reactor 101 via reactor inlet 110. The reactant, diluent, and inert material (e.g., which can be the same as the diluent) can mix upon injection into reactor 101 at injection point 103 (see FIGS. 3 to 5 for injection point 103). The reactant can be mixed with the diluent and inert material prior to contact with the catalyst system in reactor 101, and the desired product (e.g., oligomer) can be formed while preventing fouling of reactor inlet 110. An effluent can be removed from reactor 101 via reactor outlet 197.

Figure 11:
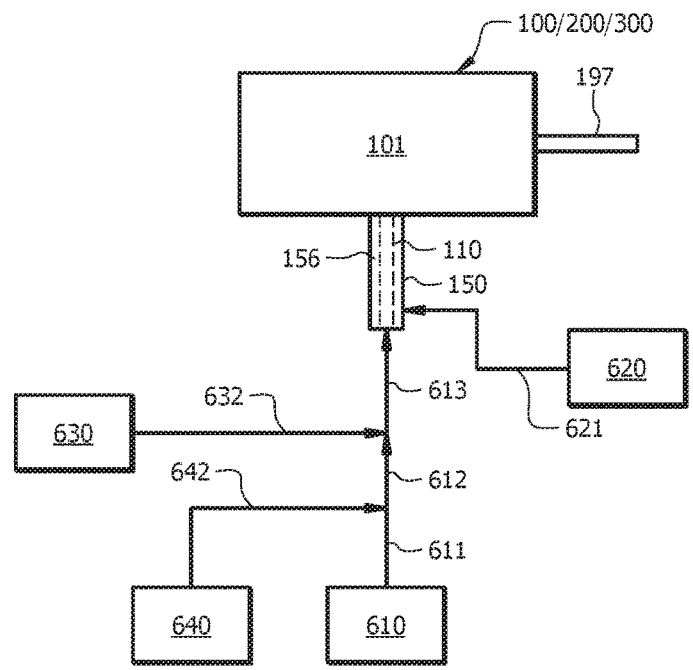
FIG. 11 illustrates an alternative configuration to those shown in FIG. 9 and FIG. 10.

FIG. 11 illustrates an alternative configuration to those shown in FIG. 9 and FIG. 10. Any one of system 100/200/300 of FIGS. 3 to 5 can be coupled to one or more of reactant source 610, inert material source 620, catalyst system source 630, and diluent source 640. FIG. 11 shows the diluent can flow from diluent source 640 via diluent feed line 642 and can combine with the reactant from reactant feed line 611 to form first combined feed line 612. FIG. 11 also shows the catalyst system can flow from catalyst system source 630 via catalyst system feed line 632 and can combine with first combined feed line 612 to form a second combined feed line 613. Second combined feed line 613 can feed the mixture of diluent, reactant, and catalyst system to reactor 101 via reactor inlet 110 (shown with dashed lines in FIG. 11).

Inert material source 620 can provide an inert material to reactor 101 via annular space 156 formed between inlet sleeve 150 and reactor inlet 110. The inert material can flow to reactor 101 through inert material feed line 621 which is fluidly connected to annular space 156. The reactant (e.g., ethylene) and the diluent can mix in line 612 before being combined with the catalyst system. The catalyst system, reactant, and diluent can mix in second combined feed line 613 before being injected to reactor 101 via reactor inlet 110. The catalyst system, reactant, diluent, and inert material (e.g., which can be the same as the diluent) can mix upon injection into reactor 101 at injection point 103 (see FIGS. 3 to 5 for injection point 103). Contrasted with FIG. 10, reactant in FIG. 11 can be mixed with the diluent in first combined feed line 612 prior to contact with the catalyst system in second combined feed line 613. That is, the reactant contacts the catalyst system outside of reactor 101 in FIG. 11, and said contact can form product in line 613 prior to injection to reactor 101. Even with contact of the catalyst system with the reactant prior to feeding to reactor 101 via reactor inlet 110, the desired product (e.g., oligomer) can be formed while preventing fouling of reactor inlet 110. Fouling of end 112 of reactor inlet 110 can be prevented because even though product can be formed in line 613, accumulation of the product on end 112 of reactor inlet 110 can be mitigated via the techniques disclosed herein. An effluent can be removed from reactor 101 via reactor outlet 197.

Figure 12:
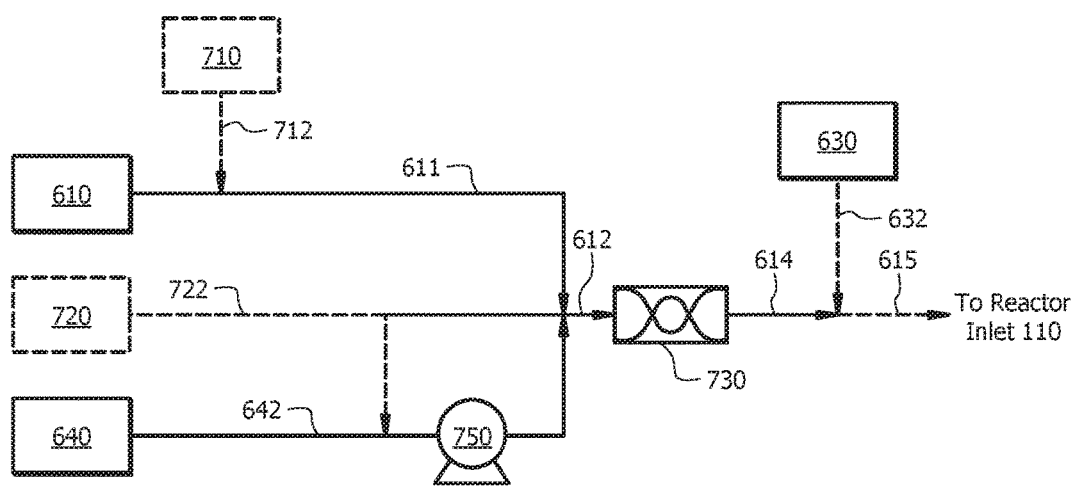
FIG. 12 illustrates an alternative configuration to those shown in FIGS. 9 to 11.

FIG. 12 illustrates an alternative configuration to those shown in FIGS. 9 to 11. The reactant can flow from reactant source 610 in reactant feed line 611, and the diluent can flow from diluent source 640 in diluent feed line 642. Reactant feed line 611 and diluent feed line 642 can combine to form combined feed line 612. A pump 750 can be utilized to flow the diluent feed line 642 for combination with the reactant feed line 611.

The reactant and diluent in combined feed line 612 can flow to a mixing device 730. Mixing device 730 can be any device which can mix/disperse the reactant (e.g., ethylene) and the diluent. Such mixing/dispersing can be implemented to minimize areas of high reactant concentration within reactor inlet 110 and also at injection point 103 (injection point 103 is shown in FIGS. 3-5). Mixing device 730 can provide mixing of reactant and diluent via agitation of the flow there through. For example, mixing device 730 can be a static mixer having fixed baffles (e.g., in a helical arrangement, or any other baffle arrangement) placed within a housing, where the baffles continuously blend the reactant and diluent to disperse the reactant and diluent in the mixture. Alternatively, mixing device 730 can have moving parts such as a propeller or impeller. In an aspect, mixing device 730 can be useful for embodiments in which the reactant is contacted with the catalyst system prior to entering reactor 101 (e.g., as seen in FIGS. 3-5) via reactor inlet 110 because the mixing device can provide a pre-diluted reactant which is injected via reactor inlet 110. It is contemplated that pre-dilution can enhance the prevention of fouling on end 112 (as seen in FIGS. 3-5) of reactor inlet 110. In some aspects the mixing or dispersion of the reactant and diluent can be accomplished using a precontactor device, such as a vessel having mixing device 730 disposed therein.

The mixed/dispersed mixture of reactant and diluent can flow from the mixing device 730 via mixed feed line 614. Mixed feed line 614 can fluidly connect directly with reactor inlet 110 of systems 100, 200, or 300. Alternatively, mixed feed line 614 can combine with catalyst system feed line 632 (shown with dashed lines flowing from catalyst system source 630) to form mixed catalyst feed line 615. Mixed catalyst feed line 615 can fluidly connect directly with reactor inlet 110 of system 100, 200, or 300.

Reactant feed line 611 can optionally include hydrogen received from a hydrogen source 710 via hydrogen feed line 712 (shown with dashed lines). While the location of hydrogen injection is shown in reactant feed line 611 in FIG. 12, it is contemplated that hydrogen can additionally or alternatively be injected into diluent feed line 642, combined feed line 612, mixed feed line 614, catalyst system feed line 632, mixed catalyst feed line 615, reactor 101, or a combination thereof.

A scrub agent source 720 and associated scrub agent feed line 722 can optionally be included (shown with dashed lines). The scrub agent source 720 can be physically embodied, for example, as a storage tank or precontactor. In aspects, the scrub agent can be an alkylaluminum compound. In an aspect, the alkylaluminum compound which can be utilized as the scrub agent can be an aluminoxane. Aluminoxanes are independently disclosed herein (e.g., as a component of the catalyst system) and any of the general or specific aluminoxanes disclosed herein can be utilized without limitation as the scrub agent utilized in the processes and systems disclosed herein.

The disclosed systems 100/200/300 and associated processes are not limited to a particular catalyst system, and it is contemplated that the configurations of inlet sleeve 150 and reactor inlet 110 disclosed herein can prevent fouling for any reactant/catalyst system combination for which fouling is a problem.

$N^2$-phosphinyl

In aspects and embodiments, the catalyst system can comprise i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and ii) an aluminoxane. In some aspects, the catalyst system can comprise i) a chromium component comprising an $N^2$-phosphinyl formamidine chromium compound complex and ii) an aluminoxane; alternatively, i) a chromium component comprising an $N^2$-phosphinyl amidine chromium compound complex and ii) an aluminoxane; or alternatively, i) a chromium component comprising an $N^2$-phosphinyl guanidine chromium compound complex and ii) an aluminoxane. Generally, the $N^2$-phosphinyl amidine chromium compound complex, the $N^2$-phosphinyl formamidine chromium compound complex, the $N^2$-phosphinyl guanidine chromium compound complex, the aluminoxane, and any other element of the catalyst system described herein are independent elements of the catalyst systems. These catalyst system elements are independently described herein and can be utilized without limitation, and in any combination, to further describe a catalyst system utilized in aspects and/or embodiments of the processes and systems described herein.

In an aspect, the $N^2$-phosphinyl formamidine chromium compound complex utilized in the catalyst systems described herein can comprise, can consist essentially of, or can be, an $N^2$-phosphinyl formamidine chromium compound complex having the Structure NPFCr1. In an aspect, the $N^2$-phosphinyl amidine chromium compound complex utilized in the catalyst systems described herein can comprise, can consist essentially of, of can be, an $N^2$-phosphinyl amidine chromium compound complex having the Structure NPACr1. In an aspect, the $N^2$-phosphinyl guanidine chromium compound complex utilized in the catalyst systems described herein can comprise, can consist essentially of, or can be, an N²-phosphinyl guanidine chromium compound complex having the Structure GuCr1, GuCr2, GuCr3, GuCr4, or GuCr5; alternatively, an N²-phosphinyl guanidine chromium compound complex having the Structure GuCr1; alternatively, an N²-phosphinyl guanidine chromium compound complex having the Structure GuCr2; alternatively, an N²-phosphinyl guanidine chromium compound complex having the Structure GuCr3; alternatively, an N²-phosphinyl guanidine chromium compound complex having the Structure GuCr4; or alternatively, an N²-phosphinyl guanidine chromium compound complex having the Structure GuCr5.

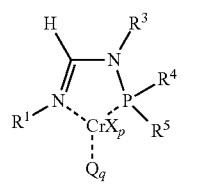

Structure NPFCr1

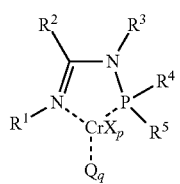

Structure NPACr1

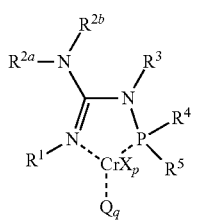

Structure GuCr1

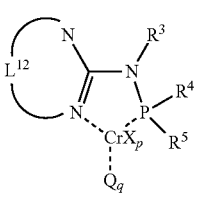

Structure GuCr2

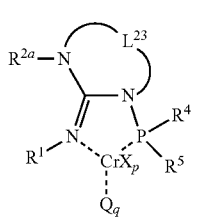

Structure GuCr3

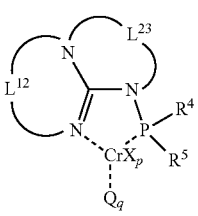

Structure GuCr4

-continued

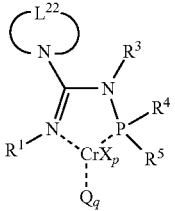

Structure GuCr5

Within the N²-phosphinyl formamidine chromium compound complexes and the N²-phosphinyl amidine chromium compound complexes, the nitrogen participating in a double bond with the central carbon atom is referred to as the N¹ nitrogen and the nitrogen atom participating in a single bond with the central carbon atom is referred to as the N² nitrogen. Similarly, within the N²-phosphinyl guanidine chromium compound complexes, the nitrogen participating in a double bond with the central carbon atom of the guanidine core is referred to as the N¹ nitrogen, the nitrogen atom participating in a single bond with the central carbon atom of the guanidine core and a bond with the phosphorus atom of the phosphinyl group is referred to as the N² nitrogen, and the remaining nitrogen atom participating in a single bond with the central carbon atom of the guanidine core is referred to as the N³ nitrogen. It should be noted that the guanidine group of the guanidine in the N²-phosphinyl guanidine transition metal complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

R¹, R³, R⁴, and R⁵ within the N²-phosphinyl formamidine chromium compound complexes having Structure NPFCr1, the N²-phosphinyl amidine chromium compound complexes having Structure NPACr1, and the N²-phosphinyl guanidine chromium compound complexes having the Structures GuCr1, GuCr2, GuCr3, GuCr4, and/or GuCr5 are independently described herein and can be utilized without limitation to further describe the N²-phosphinyl formamidine chromium compound complexes having Structure NPFCr1, the N²-phosphinyl amidine chromium compound complexes having Structure NPACr1, and/or the N²-phosphinyl guanidine chromium compound complexes having the Structures GuCr1, GuCr2, GuCr3, GuCr4, and/or GuCr5. Similarly, R² within the N²-phosphinyl amidine chromium compound complexes having Structure NPACr1 are independently described herein and can be utilized without limitation to further describe the N²-phosphinyl amidine chromium compound complexes having Structure NPACr1. Similarly, $R^{2a}$, $R^{2b}$, $L^{12}$, $L^{22}$, and $L^{23}$ within the N²-phosphinyl guanidine chromium compound complexes having the Structures GuCr1, GuCr2, GuCr3, GuCr4, or GuCr5 are independently described herein and can be utilized without limitation to further describe the N²-phosphinyl guanidine chromium compound complexes having the Structures GuCr1, GuCr2, GuCr3, GuCr4, and/or GuCr5. $MX_p$, Q, and q of the N²-phosphinyl formamidine chromium compound complexes, the N²-phosphinyl amidine chromium compound complexes, and the N²-phosphinyl guanidine chromium compound complexes are independently described herein and can be utilized in any combination, and without limitation, to further describe the $N^2$-phosphinyl formamidine chromium compound complexes, the $N^2$-phosphinyl amidine chromium compound complexes, and the $N^2$-phosphinyl guanidine chromium compound complexes. Additionally, $MX_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complexes, the $N^2$-phosphinyl amidine chromium compound complexes, and the $N^2$-phosphinyl guanidine chromium compound complexes described herein which have an $R^1$, $R^2$, $R^{2a}$, $R^{2b}$, $R^3$, $R^4$, $R^5$, $L^{12}$, $L^{22}$, and/or $L^{23}$.

Generally, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an organyl group; alternatively, an organyl group consisting essentially of inert functional groups; or alternatively, a hydrocarbyl group. In an aspect, the $R^1$ organyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group. In an aspect, the $R^1$ organyl group consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ organyl group consisting essentially of inert functional groups. In an aspect, the $R^1$ hydrocarbyl group of the $N^2$-phosphinyl formamidine chromium compound complexes, the $N^2$-phosphinyl amidine chromium compound complexes, and/or the $N^2$-phosphinyl guanidine chromium compound complexes, which have an $R^1$ group, can be a $C_1$ to $C_{20}$, a $C_1$ to $C_{15}$, a $C_1$ to $C_{10}$, or a $C_1$ to $C_5$ hydrocarbyl group.

In an aspect, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group. In some aspects, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^1$ of the $N^2$-phosphinyl formamidine chromium compound complexes, the $N^2$-phosphinyl amidine chromium compound complexes, and/or the $N^2$-phosphinyl guanidine chromium compound complexes which have an $R^1$ group can be an alkyl group; alternatively, a substituted alkyl group; alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^1$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^1$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^1$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^1$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^1$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^1$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^1$ can be a $C_7$ to $C_{20}$, a $C_7$ to $C_{15}$, or a $C_7$ to $C_{10}$ aralkyl group. In any aspect or embodiment disclosed herein, the substituted aralkyl group which can be utilized as $R^1$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^1$.

In an aspect, $R^1$ can be a methyl group, an ethyl group, a propyl group, a butyl group, a pentyl group, a hexyl group, a heptyl group, or an octyl group. In some aspects, one or more of $R^1$ can be a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some aspects, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an aspect, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized as $R^1$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an aspect, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting aspect, $R^1$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, any one or more of $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, one or more of $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^1$ can be a phenyl group, a substituted phenyl group; alternatively, a phenyl group; or alternatively, a substituted phenyl group. In an aspect, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting aspect, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^1$. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, one or more of $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidine chromium compound complexes can be an organyl group; alternatively, an organyl group consisting essentially of inert functional groups; or alternatively, a hydrocarbyl group. In an aspect, $R^2$ organyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group. In an aspect, $R^2$ organyl group consisting essentially of inert functional groups of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ organyl group consisting essentially of inert functional groups. In an aspect, $R^2$ hydrocarbyl group of the $N^2$-phosphinyl amidine chromium compound complexes can be a $C_1$ to $C_{20}$, a $C_1$ to $C_{15}$, a $C_1$ to $C_{10}$, or a $C_1$ to $C_5$ hydrocarbyl group.

In an aspect, $R^2$ of the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group. In some aspects, $R^2$ of the $N^2$-phosphinyl amidine chromium compound complexes can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^2$ of the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^2$ can be a $C_1$ to $C_{20}$, a $C_1$ to $C_{10}$, or a $C_1$ to $C_5$ alkyl group. In any aspect or embodiment disclosed herein, the substituted alkyl group which can be utilized as $R^2$ can be a $C_1$ to $C_{20}$, a $C_1$ to $C_{10}$, or a $C_1$ to $C_5$ substituted alkyl group. In any aspect or embodiment disclosed herein, the cycloalkyl group which can be utilized as $R^2$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^2$ can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^2$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^2$ can be a $C_6$ to $C_{20}$, a $C_6$ to $C_{15}$, or a $C_6$ to $C_{10}$ substituted aryl group. In any aspect or embodiment disclosed herein, the aralkyl group which can be utilized as $R^2$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^2$ can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an aspect, $R^2$ can be a methyl group, an ethyl group, a propyl group, a butyl group, a pentyl group, a hexyl group, a heptyl group, or an octyl group. In some aspects, one or more of $R^2$ can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some aspects, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an aspect, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized as $R^2$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an aspect, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting aspect, $R^2$ can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, any one or more of $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, one or more of $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^2$ can be a phenyl group, a substituted phenyl group; alternatively, a phenyl group; or alternatively, a substituted phenyl group. In an aspect, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting aspect, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting aspects, one or more of $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^2$ can be a phenyl group, a 2-alkoxyphenyl group, or a 4-alkoxyphenyl group. In some non-limiting aspects, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting aspect, $R^2$ can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some aspects, $R^2$ can be a phenyl group, a 2-fluorophenyl group, a 4-fluorophenyl group, or a 2,6-difluorophenyl group.

In an aspect, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

Generally, $R^{2a}$ and/or $R^{2b}$, of the $N^2$-phosphinyl guanidine chromium compound complexes which have an $R^{2a}$ and/or $R^{2b}$ group, independently can be hydrogen or an organyl group; alternatively, hydrogen; or alternatively, an organyl group. In another aspect, $R^{2a}$ and/or $R^{2b}$, of the $N^2$-phosphinyl guanidine chromium compound complexes which have an $R^{2a}$ and/or $R^{2b}$ group, independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$, of the $N^2$-phosphinyl guanidine chromium compound complexes which have an $R^{2a}$ and/or $R^{2b}$ group, independently can be hydrogen or a hydrocarbyl group; alternatively, hydrogen; or alternatively, a hydrocarbyl group. In an aspect, the $R^{2a}$ and $R^{2b}$ organyl groups of the $N^2$-phosphinyl guanidine chromium compound complexes which have an $R^{2a}$ and/or $R^{2b}$ organyl group, independently can be a $C_1$ to $C_{20}$, a $C_1$ to $C_{15}$, a $C_1$ to $C_{10}$, or a $C_1$ to $C_5$ organyl group. In some aspects, the $R^{2a}$ and/or $R^{2b}$ organyl groups consisting of inert functional groups, of the $N^2$-phosphinyl guanidine chromium compound complexes which have an $R^{2a}$ and/or $R^{2b}$ organyl consisting of inert functional groups, independently can be a $C_1$ to $C_{20}$, a $C_1$ to $C_{15}$, a $C_1$ to $C_{10}$, or a $C_1$ to $C_5$ organyl group consisting essentially of inert functional groups. In other aspects, the $R^{2a}$ and/or $R^{2b}$ hydrocarbyl groups, of the $N^2$-phosphinyl guanidine chromium compound complexes which have an $R^{2a}$ and/or $R^{2b}$ hydrocarbyl group, independently can be a $C_1$ to $C_{20}$, a $C_1$ to $C_{15}$, a $C_1$ to $C_{10}$, or a $C_1$ to $C_5$ hydrocarbyl group.

In an aspect, $R^{2a}$ and $R^{2b}$, of the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group. In some aspects, $R^{2a}$ and $R^{2b}$, of the $N^2$-phosphinyl guanidine chromium compound complexes which have an $R^{2a}$ and/or $R^{2b}$ organyl group, independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{2a}$ and $R^{2b}$, of the $N^2$-phosphinyl guanidine chromium compound complexes which have an $R^{2a}$ and/or $R^{2b}$ organyl group, independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, $R^{2a}$ and/or $R^{2b}$ independently can be $C_1$ to $C_{20}$, a $C_1$ to $C_{10}$, or a $C_1$ to $C_5$ alkyl group. In any aspect or embodiment disclosed herein, the cycloalkyl group which can be utilized as $R^{2a}$ and/or $R^{2b}$ independently can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{2a}$ and/or $R^{2b}$ independently can be a $C_4$ to $C_{20}$, a $C_4$ to $C_{15}$, or a $C_4$ to $C_{10}$ substituted cycloalkyl group. In any aspect or embodiment disclosed herein, the aryl group which can be utilized as $R^{2a}$ and/or $R^{2b}$ independently can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{2a}$ and/or $R^{2b}$ independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidine chromium compound complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine chromium compound complexes can be joined to form a group, $L^{23}$, wherein $L^{23}$, the $N^2$ nitrogen atom, and the $N^3$ nitrogen atom can form a ring or a ring system. In an aspect, $L^{12}$ and/or $L^{23}$, of the $N^2$-phosphinyl guanidine chromium compound complexes which have an $L^{12}$ group and/or an $L^{23}$ group, independently can be an organylene group; alternatively, an organylene group consisting of inert functional groups; or alternatively, a hydrocarbylene group. The organylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group. The organylene group consisting of inert functional groups which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ organylene group consisting of inert functional groups. The hydrocarbylene group which can be utilized as $L^{12}$ and/or $L^{23}$ of the $N^2$-phosphinyl guanidine chromium compound complexes which have an $L^{12}$ group and/or an $L^{23}$ group independently can be a $C_2$ to $C_{20}$, a $C_2$ to $C_{15}$, a $C_2$ to $C_{10}$, or a $C_2$ to $C_5$ hydrocarbylene group.

In an aspect, $L^{12}$ and/or $L^{23}$ can have any structure provided in Table 1. In some aspects, $L^{12}$ and/or $L^{23}$ can have Structure 1L, Structure 2L, Structure 3L, Structure 4L or Structure 5L. In some aspects, $L^{12}$ and/or $L^{23}$ can have Structure 2L or Structure 3L; alternatively, Structure 4L or Structure 5L. In other aspects, $L^{12}$ and/or $L^{23}$ can have Structure 1L; alternatively, Structure 2L; alternatively, Structure 3L; alternatively, Structure 4L; or alternatively, Structure 5L. In some aspects, $L^{12}$ and/or $L^{23}$ can have Structure 6L. It should be noted that when $L^{12}$ has Structure 6L the corresponding $R^{2b}$ is null because of the double bond link (depicted as real but can be delocalized through aromatic resonance) with the $N^3$ nitrogen atom of the $N^2$-phosphinyl guanidine metal complex.

TABLE 1

Structures for Linking Groups $L^{12}$ and/or $L^{23}$.

| | |
|---|---|
| —$(CR^{L1}R^{L2})_m$— | Structure 1L |
| —$CR^{L3}R^{L4}$—$CR^{L5}R^{L6}$— | Structure 2L |
| —$CR^{L3}R^{L4}$—$CR^{L7}R^{L8}$—$CR^{L5}R^{L6}$— | Structure 3L |
| —$CR^{11L}$=$CR^{12L}$— | Structure 4L |
| 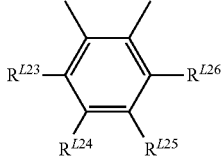 | Structure 5L |
| =$CR^{27}$—$CR^{28}$=$CR^{29}$— | Structure 6L |

Within the structures of Table 1, the undesignated valences represent the points at which $L^{12}$ and/or $L^{23}$, when present, attach to the respective nitrogen atoms of the $N^2$-phosphinyl guanidine chromium compound complex. Generally, m can be an integer ranging from 2 to 5. In further aspects, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$ and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, and/or Structure 5L. In an aspect, $L^{12}$ and/or $L^{23}$ can be an eth-1,2-ylene group (—$CH_2CH_2$—), an ethen-1,2-ylene group (—CH=CH—), a prop-1,3-ylene group (—$CH_2CH_2CH_2$—), a 1-methylethen-1,2-ylene group (—C($CH_3$)=CH—), a but-1,3-ylene group (—$CH_2CH_2$CH($CH_3$)—), or a 3-methylbut-1,3-ylene group (—$CH_2CH_2$C($CH_3$)$_2$—); alternatively, an eth-1,2-ylene group (—$CH_2CH_2$—), an ethen-1,2-ylene group (—CH=CH—), a prop-1,3-ylene group (—$CH_2CH_2CH_2$—), or a phen-1,2-ylene group; alternatively, an eth-1,2-ylene group (—$CH_2CH_2$—) or a prop-1,3-ylene group (—$CH_2CH_2CH_2$—); alternatively, an ethen-1,2-ylene group (—CH=CH—) or a phen-1,2-ylene group. In other aspects, $L^{12}$ and/or $L^{23}$ can be an eth-1,2-ylene group (—$CH_2CH_2$—); alternatively, an ethen-1,2-ylene group (—CH=CH—); alternatively, a prop-1,3-ylene group (—$CH_2CH_2CH_2$—); alternatively, a 1-methylethen-1,2-ylene group (—C($CH_3$)=CH—); alternatively, a but-,3-lene group (—$CH_2CH_2$CH($CH_3$)—); alternatively, a 3-methylbut-1,3-ylene group (—$CH_2CH_2$C($CH_3$)$_2$—); or alternatively, a phen-1,2-ylene group. In some aspects, $12^2$ and/or $L^{23}$ can be a —CH=CH—CH=group.

In an aspect, $L^{12}$ can have a structure that can comprise at least one substituent located on the carbon atom attached to the $N^1$ nitrogen atom of the $N^2$-phosphinyl guanidine chromium compound complex; alternatively, can comprise only one substituent located on the carbon atom attached to the $N^1$ nitrogen atom of the $N^2$-phosphinyl guanidine chromium compound complex; or alternatively, can comprise two substituents located on the carbon atom attached to the $N^1$ nitrogen atom of the $N^2$-phosphinyl guanidine chromium compound complex. In another aspect, $12^2$ can have a structure that can consist of one substituent located on the carbon atom attached to the $N^1$ nitrogen atom of the $N^2$-phosphinyl guanidine chromium compound complex; or alternatively, can consist of two substituents located on the carbon atom attached to the $N^1$ nitrogen atom of the $N^2$-phosphinyl guanidine chromium compound complex.

In an aspect, $R^e$a and $R^{2b}$ of the $N^2$-phosphinyl guanidine chromium compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an aspect, $L^{22}$ of the $N^2$-phosphinyl guanidine chromium compound complexes having an $L^{22}$ group can be an organylene group; alternatively, an organylene group consisting of inert functional groups; or alternatively, a hydrocarbylene group. The organylene group which can be utilized as $L^{22}$ of the $N^2$-phosphinyl guanidine chromium compound complexes having an $L^{22}$ group can be a $C_3$ to $C_{20}$, a $C_3$ to $C_{15}$, or a $C_3$ to $C_{10}$ organylene group. The organylene group consisting of inert functional groups which can be utilized as $L^{22}$ of the $N^2$-phosphinyl guanidine chromium compound complexes having an $L^{22}$ group can be a $C_3$ to $C_2o$, a $C_3$ to $C_{15}$, or a $C_3$ to $C_{10}$ organylene group consisting of inert functional groups. The hydrocarbylene group which can be utilized as $L^{22}$ of the $N^2$-phosphinyl guanidine chromium compound complexes having an $L^{22}$ group can be a $C_4$ to $C_2o$, a $C_4$ to $C_{15}$, or a $C_4$ to $C_{10}$ hydrocarbylene group.

In an aspect, $L^{22}$ can have any structure provided in Table 2. In some aspects, $L^{22}$ can have Structure 11L, Structure 12L, Structure 13L, Structure 14L, Structure 15L, or Structure 16L. In other aspects, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

| | |
|---|---|
| —$(CR^{L31}R^{L32})_n$—<br>Structure 11L | —$CR^{L41}R^{L42}$—$CR^{L45}R^{L46}$ $CR^{L47}R^{L48}$ $CR^{L43}R^{L44}$—<br>Structure 12L |
| —$CR^{L41}R^{L42}$—$CR^{L45}R^{L46}$—$CR^{L49}R^{L50}$—$CR^{L47}R^{L48}$—$CR^{L43}R^{L44}$—<br>Structure 13L | |
| —$CR^{L41}R^{L42}$—$CR^{L45}R^{L46}$—O—$CR^{L47}R^{L48}$—$CR^{L43}R^{L44}$—<br>Structure 14L | —$CR^{L51}$=$CR^{L53}$—$CR^{L54}$=$CR^{L52}$—<br>Structure 15L |

Within the structures of Table 2, the undesignated valences represent the points at which $L^{22}$ of the $N^2$-phosphinyl guanidine chromium compound complexes, when present, attach to the $N^3$ nitrogen atom of the $N^2$-phosphinyl guanidine chromium compound complex. Generally, n can be an integer ranging from 4 to 7. In further aspects, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an aspect, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

Generally, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be hydrogen or an organyl group; hydrogen or an organyl group consisting essentially of inert functional group; alternatively, hydrogen or a hydrocarbyl group; alternatively, hydrogen; alternatively, an organyl group; alternatively, an organyl group consisting essentially of inert functional group; or alternatively, a hydrocarbyl group. In an aspect, the organyl group which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ organyl group. In an aspect, the organyl group consisting essentially of inert functional groups which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{20}$, a $C_1$ to $C_{15}$, a $C_1$ to $C_{10}$, or a $C_1$ to $C_5$ organyl group consisting essentially of inert functional groups. In an aspect, the hydrocarbyl group which can utilized as $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a, a $C_1$ to $C_{20}$, a $C_1$ to $C_{15}$, a $C_1$ to $C_{10}$, or a $C_1$ to $C_5$ hydrocarbyl group. In other aspects, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other aspects, $R^3$ of the $N^2$-phosphinyl formamidine chromium compound complexes, the $N^2$-phosphinyl amidine chromium compound complexes, and/or the $N^2$-phosphinyl guanidine chromium compound complexes which have an $R^3$ group can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ of any of the $N^2$-phosphinyl formamidine chromium compound complexes, the $N^2$-phosphinyl amidine chromium compound complexes, and/or the $N^2$-phosphinyl guanidine chromium compound complexes having a non-hydrogen $R^3$ group.

Generally, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an organyl group; alternatively, an organyl group consisting essentially of inert functional groups; or alternatively, a hydrocarbyl group. In an aspect, the $R^4$ and/or $R^5$ organyl groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting essentially of inert functional groups of the $N^2$-phosphinyl formamidine chromium compound complexes, the $N^2$-phosphinyl amidine chromium compound complexes, and/or the $N^2$-phosphinyl guanidine chromium compound complexes independently can be a $C_1$ to $C_{20}$, a $C_1$ to $C_{15}$, a $C_1$ to $C_{10}$, or a $C_1$ to $C_5$ organyl group consisting essentially of inert functional groups. In an aspect, the $R^4$ and/or $R^5$ hydrocarbyl groups of the $N^2$-phosphinyl formamidine chromium compound complexes, the $N^2$-phosphinyl amidine chromium compound complexes, and/or the $N^2$-phosphinyl guanidine chromium compound complexes independently can be a, a $C_1$ to $C_{20}$, a $C_1$ to $C_{15}$, a $C_1$ to $C_{10}$, or a $C_1$ to $C_5$ hydrocarbyl group. In further aspects, $R^4$ and $R^5$ of the $N^2$-phosphinyl formamidine chromium compound complexes, the $N^2$-phosphinyl amidine chromium compound complexes, and/or the $N^2$-phosphinyl guanidine chromium compound complexes can be joined to form a ring or a ring system.

In an aspect, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group, a substituted alkyl group, a cycloalkyl group, a substituted cycloalkyl group, an aryl group, a substituted aryl group, an aralkyl group, or a substituted aralkyl group. In some aspects, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^4$ and/or $R^5$ of the $N^2$-phosphinyl formamidine chromium compound complexes, the $N^2$-phosphinyl amidine chromium compound complexes, and/or the $N^2$-phosphinyl guanidine chromium compound complexes independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^4$ and/or $R^5$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^4$ and/or $R^5$ independently can be a $C_1$ to $C_{20}$, a $C_1$ to $C_{10}$, or $C_1$ to $C_5$ substituted alkyl group. In any aspect or embodiment disclosed herein, each cycloalkyl group which can be utilized as $R^4$ and/or $R^5$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^4$ and/or $R^5$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^4$ and/or $R^5$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^4$ and/or $R^5$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized $R^4$ and/or $R^5$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^4$ and/or $R^5$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group. In some aspects, $R^4$ and $R^5$ independently can be a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$ independently.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an aspect where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect, $R^4$ and $R^5$ independently can be a cyclohexyl group, a 2-alkylcyclohexyl group, or a 2,6- dialkylcyclohexyl group; alternatively, a cyclopentyl group, a 2-alkylcyclopentyl group, or a 2,5-dialkylcyclopentyl group; alternatively, cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, or 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^1$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting aspect, $R^4$ and $R^5$ independently can be a phenyl group, a 2-halophenyl group, a 4-halophenyl group, or a 2,6-dihalophenyl group. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

Generally, the chromium compound of the $N^2$-phosphinyl formamidine chromium compound complexes, the $N^2$-phosphinyl amidine chromium compound complexes, and/or the $N^2$-phosphinyl guanidine chromium compound complexes described herein can have the formula $CrX_p$ where X represents a monoanionic ligand, and p represent the number of monoanionic ligands (and the oxidation state of the chromium in the chromium compound). The monoanionic ligand (X) and p are independent elements of the chromium compound and are independently described herein. The independent descriptions of the monoanionic ligand (X) and p can be utilized without limitation, and in any combination, to further describe the chromium compound of the $N^2$-phosphinyl formamidine chromium compound complexes, the $N^2$-phosphinyl amidine chromium compound complexes, and/or the $N^2$-phosphinyl guanidine chromium compound complexes.

Generally, the chromium atom of the chromium compound ($CrX_p$) can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound ($CrX_p$) can have an oxidation state of +1; alternatively, +2; alternatively, +3; or alternatively, +4.

The monoanion, X, of the chromium compound can be any monoanion. In an aspect, the monoanion, X, can be a halide, a carboxylate, a β-diketonate, a hydrocarboxide, a nitrate, or a chlorate. In some aspects, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion, X, can be a halide, a carboxylate, a β-diketonate, or an alkoxide; or alternatively, a halide or a β-diketonate. In other aspects, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an aspect, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion, X, of the chromium compound independently can be fluorine, chlorine, bromine, or iodine; or alternatively, chlorine, bromine, or iodine. In an aspect, each halide monoanion, X, of the chromium compound can be chlorine; alternatively, bromine; or alternatively, iodine.

Generally, each carboxylate monoanion of the chromium compound independently can be a $C_1$ to $C_{20}$ carboxylate; or alternatively, a $C_1$ to $C_{10}$ carboxylate. In an aspect, each carboxylate monoanion of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate monoanion of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, the carboxylate monoanion of the chromium compound can be triflate (trifluoroacetate).

Generally, each β-diketonate monoanion of the chromium compound independently can be any $C_1$ to $C_{20}$ a β-diketonate; or alternatively, any $C_1$ to $C_{10}$ β-diketonate. In an aspect, each β-diketonate monoanion of the chromium compound independently can be acetylacetonate (i.e., 2,4-pentanedionate), hexafluoroacetylacetone (i.e., 1,1,1,5,5,5-hexafluoro-2,4-pentanedionate), or benzoylacetonate); alternatively, acetylacetonate; alternatively, hexafluoroacetylacetone; or alternatively, benzoylacetonate.

Generally, each hydrocarboxide monoanion of the chromium compound independently can be any $C_1$ to $C_{20}$ hydrocarboxide; or alternatively, any $C_1$ to $C_{10}$ hydrocarboxide. In an aspect, each hydrocarboxide monoanion of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide monoanion of the chromium compound independently can be methoxide, ethoxide, a propoxide, or a butoxide. In some aspects, each alkoxide monoanion of the chromium compound independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In a non-limiting aspect, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein can comprise, can consist essentially of, or consist of, a chromium(II) halide, a chromium(III) halide, a chromium(II) carboxylate, chromium(III) carboxylate, a chromium(II) β-diketonate, or a chromium(III) β-diketonate. In some non-limiting aspects, the chromium compound of any of the $N^2$-phosphinyl formamidine chromium compound complexes, $N^2$-phosphinyl amidine chromium compound complexes, and/or the $N^2$-phosphinyl guanidine chromium compound complexes described herein described herein can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, a chromium(II) halide; alternatively, a chromium(III) halide; alternatively, a chromium (II) carboxylate; alternatively, a chromium(III) carboxylate;

alternatively, a chromium(II) β-diketonate; or alternatively, a chromium(III) β-diketonate.

In a non-limiting aspect, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(II) chloride, chromium(III) chloride, chromium(II) fluoride, chromium (III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (III) benzoylacetonate, or chromium(III) benzoylacetonate. In some non-limiting aspects, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can comprise, can consist essentially of, or consist of, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium (III) acetylacetonate, chromium(III) hexafluoracetylacetonate, or chromium(III) benzoylacetonate. In further aspects, the chromium compound of any of the $N^2$-phosphinyl formamidine chromium compound complexes, $N^2$-phosphinyl amidine chromium compound complexes, and/or $N^2$-phosphinyl guanidine chromium compound complexes described herein can be chromium(III) chloride, or chromium(III) acetylacetonate; alternatively, chromium(III) chloride; or alternatively, chromium(III) acetylacetonate.

Generally, the neutral ligand, Q, of any of the $N^2$-phosphinyl formamidine chromium compound complexes, the $N^2$-phosphinyl amidine chromium compound complexes, and/or the $N^2$-phosphinyl guanidine chromium compound complexes described herein, if present, independently can be any neutral ligand that forms an isolatable compound with the $N^2$-phosphinyl formamidine chromium compound complex, the $N^2$-phosphinyl amidine chromium compound complex, and/or the $N^2$-phosphinyl guanidine chromium compound complex. In an aspect, each neutral ligand independently can be a nitrile or an ether; alternatively, a nitrile; or alternatively, an ether. The number of neutral ligands, q, can be any number that forms an isolatable compound with the $N^2$-phosphinyl formamidine chromium compound complexes, the $N^2$-phosphinyl amidine chromium compound complexes, and/or the $N^2$-phosphinyl guanidine chromium compound complexes. In an aspect, the number of neutral ligands of any of the $N^2$-phosphinyl formamidine chromium compound complexes, the $N^2$-phosphinyl amidine chromium compound complexes, and/or the $N^2$-phosphinyl guanidine chromium compound complexes described herein can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

In a non-limiting aspect, the $N^2$-phosphinyl formamidine chromium compound complex can be any one or more of NPFCr I, NPFCr II, NPFCrR III, NPFCr IV, NPFCr V, and NPFCr VI. In a non-limiting aspect, the $N^2$-phosphinyl amidine chromium compound complex can be any one or more of NPACR I, NPACR II, NPACr III, NPACr IV, NPACr V, NPACr VI, NPACr VII, NPACr VIII, NPACr IX, NPACr X, NPACr XI, and NPACr XII. In a non-limiting aspect, the $N^2$-phosphinyl guanidine chromium compound complex can be any one or more of GuFCr I, GuCr II, GuCr III, GuCr IV, GuCr V, and GuCr VI. In a non-limiting aspects, the chromium compound, $CrX_3$, of any of NPFCr I, NPFCr II, NPFCrR III, NPFCr IV, NPFCr V, NPFCr VI, NPACR I, NPACR II, NPACr III, NPACr IV, NPACr V, NPACr VI, NPACr VII, NPACr VIII, NPACr IX, NPACr X, NPACr XI, NPACr XII, GuFCr I, GuCr II, GuCr III, GuCr IV, GuCr V, and GuCr VI can be chromium(III) chloride or chromium(III) acetylacetonate; alternatively, chromium(III) chloride; or alternatively, chromium(III) acetylacetonate.

NPFCr I

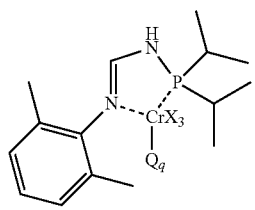

NPFCr II

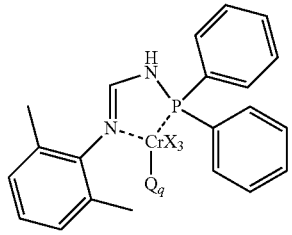

NPFCr III

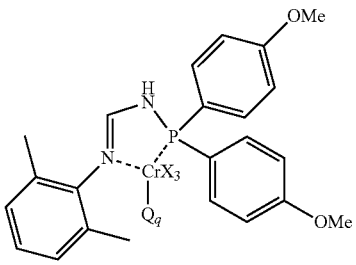

NPFCr IV

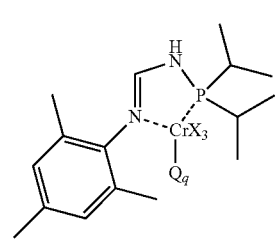

NPFCr V

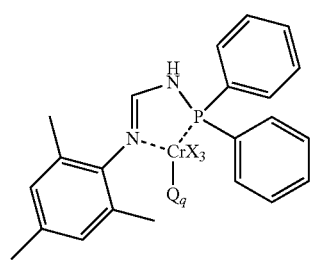

NPFCr VI

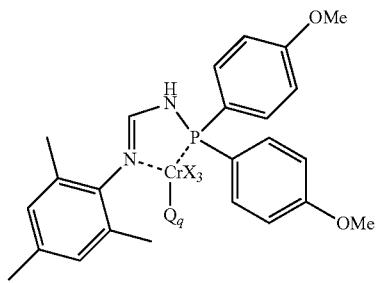

NPACr I

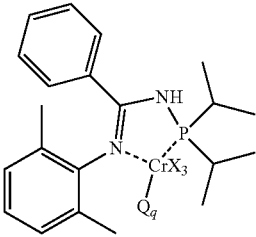

NPACr II

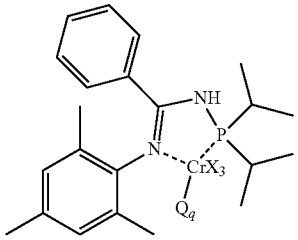

NPACr III

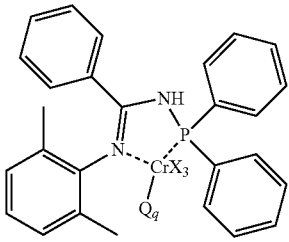

NPACr IV

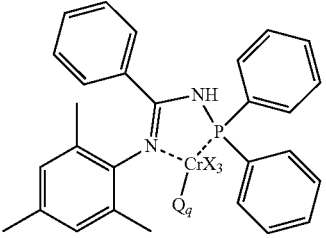

NPACr V

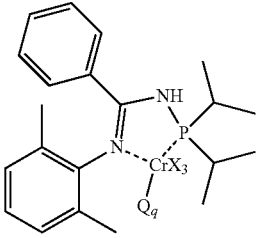

-continued
NPACr VI
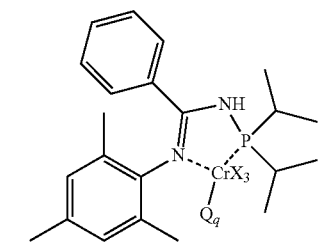
NPACr VII
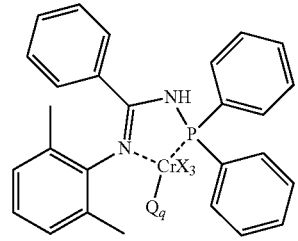
NPACr VIII
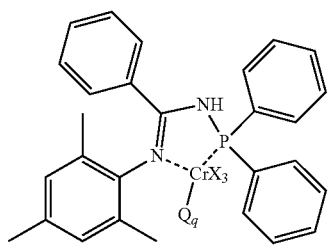
NPACr IX
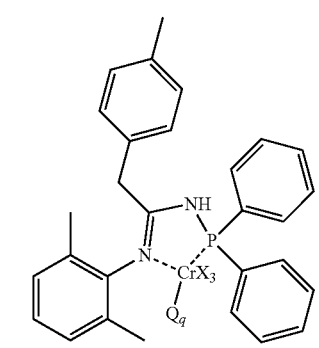
NPACr X
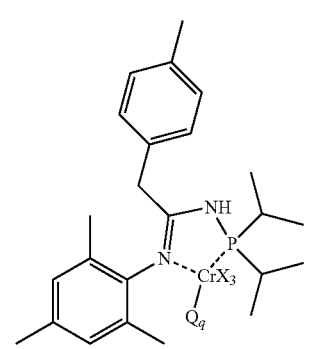
-continued
NPACr XI
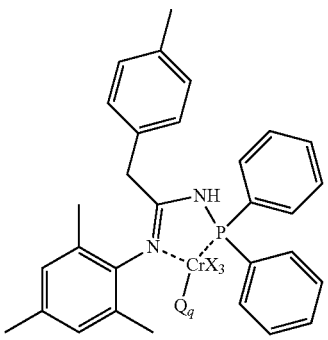
NPACr XII
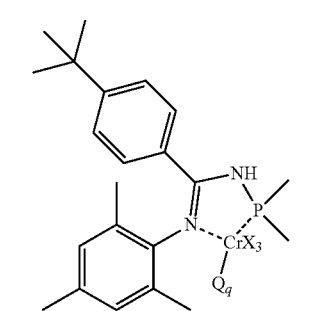
NPACr I
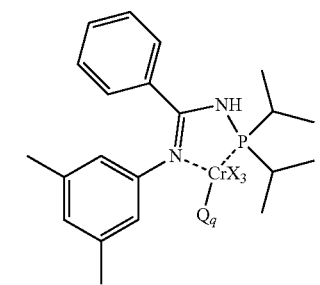
NPACr I
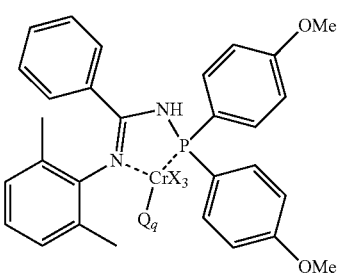
NPACr I
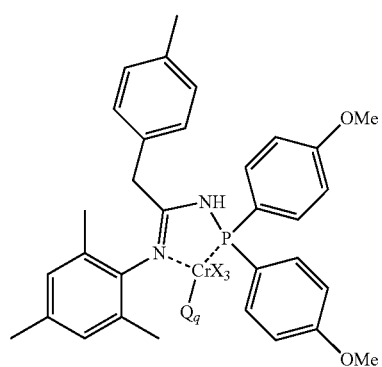

NPACr I

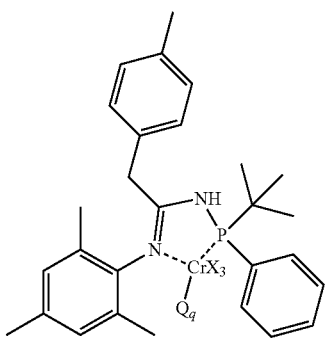

GuCr I

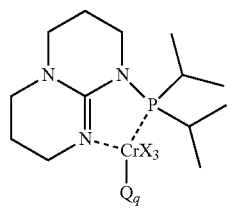

GuCr II

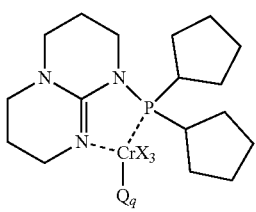

GuCr III

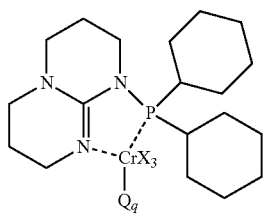

GuCr IV

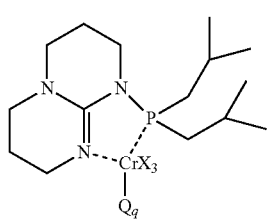

GuCr V

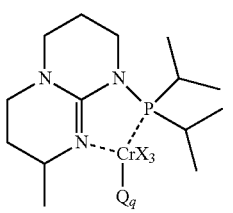

GuCrV I

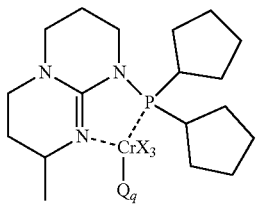

Cr-PNP Catalyst

Aspects and embodiments of the herein described processes and systems can utilize a catalyst system comprising i) a chromium component comprising a chromium compound, ii) a heteroatomic ligand, and iii) an aluminoxane; or alternatively, i) a chromium component comprising a heteroatomic ligand chromium compound complex, and ii) an aluminoxane. Generally, the chromium compound, the heteroatomic ligand, the chromium compound, the heteroatomic ligand chromium compound complex, the aluminoxane, and any other element of the catalyst system described herein are independent elements of their respective catalyst systems. These catalyst system elements are independently described herein and can be utilized without limitation, and in any combination, to further describe catalyst system utilized in aspects and/or embodiments of the processes and systems described herein.

Generally, the chromium compound or the chromium compound of the heteroatomic ligand chromium compound complexes described herein can have formula $CrX_p$ where X represents a monoanionic ligand, and p represent the number of monoatomic ligands (and the oxidation state of the chromium in the chromium compound. The monoanionic ligand (X) and p are independent elements of the chromium compound or the chromium compound of the heteroatomic ligand chromium compound complexes described herein and are independently described herein. The independent descriptions of the monoanionic ligand (X) and p can be utilized without limitation, and in any combination, to further describe the chromium compound or the chromium compound of the heteroatomic ligand chromium compound complexes described herein.

Generally, the chromium atom of the chromium compound or the chromium compound of the heteroatomic ligand chromium compound complexes described herein can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound or the chromium compound of the heteroatomic ligand chromium compound complexes described herein can have an oxidation state of +1; alternatively, +2; alternatively, +3; or alternatively, +4.

The monoanion, X, of the chromium compound or the chromium compound of the heteroatomic ligand chromium compound complexes described herein can be any monoanion. In an aspect, the monoanion, X, can be a halide, a carboxylate, a β-diketonate, a hydrocarboxide, a nitrate, or a chlorate. In some aspects, the monoanion, X, can be a halide, a carboxylate, a β-diketonate, or a hydrocarboxide. In any aspect or embodiment, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion, X, can be a halide, a carboxylate, a β-diketonate, or an alkoxide; or alternatively, a halide or a β-diketonate. In other aspects, the monoanion, X, can be a halide; alternatively, a carboxylate; alternatively, a β-diketonate; alternatively, a hydrocarboxide; alternatively, an alkoxide; or alternatively, an aryloxide. Generally, the number, p, of monoanions can equal the oxidation state of the metal atom. In an aspect, the number, p, of monoanions, X, can be from 2 to 6; alternatively, from 2 to 4; alternatively, from 2 to 3; alternatively, 1; alternatively, 2; alternatively, 3; or alternatively, 4.

Generally, each halide monoanion, X, of the chromium compound or the chromium compound of the heteroatomic ligand chromium compound complexes described herein independently can be fluorine, chlorine, bromine, or iodine; or alternatively, chlorine, bromine, or iodine. In an aspect, each halide monoanion, X, of the chromium compound or the chromium compound of the heteroatomic ligand chromium compound complexes described herein can be chlorine; alternatively, bromine; or alternatively, iodine.

Generally, each carboxylate monoanion of the chromium compound or the chromium compound of the heteroatomic ligand chromium compound complexes described herein independently can be a $C_1$ to $C_{20}$ carboxylate; or alternatively, a $C_1$ to $C_{10}$ carboxylate. In an aspect, each carboxylate monoanion of the chromium compound or the chromium compound of the heteroatomic ligand chromium compound complexes described herein independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate monoanion of the chromium compound or the chromium compound of the heteroatomic ligand chromium compound complexes described herein independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate); or alternatively, 2-ethylhexanoate. In some aspects, the carboxylate monoanion of the chromium compound or the chromium compound of the heteroatomic ligand chromium compound complexes described herein can be triflate (trifluoroacetate).

Generally, each β-diketonate monoanion of the chromium compound or the chromium compound of the heteroatomic ligand chromium compound complex independently can be any $C_1$ to $C_{20}$ a β-diketonate; or alternatively, any $C_1$ to $C_{10}$ β-diketonate. In an aspect, each β-diketonate monoanion of the chromium compound or the chromium compound of the heteroatomic ligand chromium compound complexes described herein independently can be acetylacetonate (i.e., 2,4-pentanedionate), hexafluoroacetylacetone (i.e., 1,1,1,5,5,5-hexafluoro-2,4-pentanediuonate), or benzoylacetonate); alternatively, acetylacetonate; alternatively, hexafluoroacetylacetone; or alternatively, benzoylacetonate.

Generally, each hydrocarboxide monoanion of the chromium compound or the chromium compound of the heteroatomic ligand chromium compound complexes described herein independently can be any $C_1$ to $C_{20}$ hydrocarboxide; or alternatively, any $C_1$ to $C_{10}$ hydrocarboxide. In an aspect, each hydrocarboxide monoanion of the chromium compound or the chromium compound of the heteroatomic ligand chromium compound complexes described herein independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide monoanion of the chromium compound or the chromium compound of the heteroatomic ligand chromium compound complexes described herein independently can be methoxide, ethoxide, a propoxide, or a butoxide. In some aspects, each alkoxide monoanion of the chromium compound or the chromium compound of the heteroatomic ligand chromium compound complexes described herein independently can be methoxide, ethoxide, isopropoxide, or tert-butoxide; alternatively, methoxide; alternatively, an ethoxide; alternatively, an iso-propoxide; or alternatively, a tert-butoxide. In an aspect, the aryloxide can be phenoxide.

In a non-limiting aspect, the chromium compound or the chromium compound of the heteroatomic ligand chromium compound complex can comprise, can consist essentially of, or consist of, a chromium(II) halide, a chromium(III) halide, a chromium(II) carboxylate, chromium(III) carboxylate, a chromium(II) β-diketonate, or a chromium(III) β-diketonate. In some non-limiting aspects, the chromium compound or the chromium compound of the heteroatomic ligand chromium compound complex can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound or the chromium compound of the heteroatomic ligand chromium compound complex can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate.

In a non-limiting aspect, the chromium compound or the chromium compound of the heteroatomic ligand chromium compound complexes described herein can comprise, can consist essentially of, or consist of, chromium(II) chloride, chromium(III) chloride, chromium(II) fluoride, chromium (III) fluoride, chromium(II) bromide, chromium(III) bromide, chromium(II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium (III) benzoylacetonate, or chromium(III) benzoylacetonate. In some non-limiting aspects, the chromium compound or the chromium compound of the heteroatomic ligand chromium compound complexes described herein can comprise, can consist essentially of, or consist of, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium (III) acetylacetonate, chromium(III) hexafluoracetylacetonate, or chromium(III) benzoylacetonate. In further aspects, the chromium compound or the chromium compound of the heteroatomic ligand chromium compound complexes described herein described herein can be chromium(III) chloride, or chromium(III) acetylacetonate; alternatively, chromium(III) chloride; or alternatively, chromium(III) acetylacetonate.

In an aspect, the heteroatomic ligand or the heteroatomic ligand of the heteroatomic ligand chromium compound complex can have the formula $(R^{1s})_m X^{1s}(L^{1s})X^{2s}(R^{2s})_n$ while the heteroatomic ligand of the heteroatomic ligand chromium compound complex can have the formula:

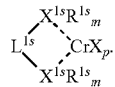

In some aspects, the heteroatomic ligand or the heteroatomic ligand of the heteroatomic ligand chromium compound complex can have two groups capable of being described by the formula $(R^{1s})_m X^{1s}(L^{1s})X^{2s}(R^{2s})_n$. In instances wherein the heteroatomic ligand can have two groups capable of being described by the formula $(R^{1s})_m X^{1s}(L^{1s})X^{2s}(R^{2s})_n$, the two $L^{1s}$ groups are linked and the heteroatomic ligand and the heteroatomic ligand chromium compound complex can have the formulas:

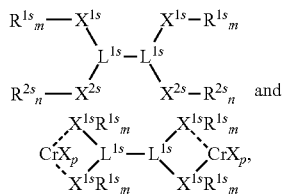

respectively.

In the heteroatomic ligand or the heteroatomic ligand of the heteroatomic ligand chromium compound complex having formula $(R^{1s})_m X^{1s}(L^{1s})X^{2s}(R^{2s})_n$ or having two linked $(R^{1s})_m X^{1s}(L^{1s})X^{2s}(R^{2s})_n$ groups, each $X^{1s}$ and each $X^{2s}$ is independently selected from the group consisting of N, P, O, and S; each $L^{1s}$ is an independent linking group between the respective $X^{1s}$s and $X^{2s}$s; each m and each n are independently 1 or 2; and each $R^{1s}$ and each $R^{2s}$ are independently hydrogen, an organyl group (or alternatively, an organyl group consisting essentially of inert functional group; or alternatively, a hydrocarbyl group), or a heterohydrocarbyl group, where when there are two or more $R^{1s}$s and/or two $R^{2s}$s, each $R^{1s}$ can be the same or different (alternatively, the same; or alternatively, different) and/or each $R^{2s}$ can be the same or different (alternatively, the same; or alternatively, different). Additionally, in the heteroatomic ligand chromium compound complex, X is a monoanionic ligand and p is the number of monoanionic ligands in the heteroatomic ligand chromium compound complex. $L^{1s}$, $X^{1s}$, $X^{2s}$, $R^{1s}$, $R^{2s}$, m, and n are independent elements of any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n and are independently described herein. These independent descriptions of $L^{1s}$, $X^{1s}$, $X^{2s}$, $R^{1s}$, $R^{2s}$, m, and n can be utilized without limitation, and in any combination, to further describe any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n. Additionally, X and p are independent elements of the chromium compound of the heteroatomic ligand chromium compound complex, are independently described herein, and can be utilized without limitation, and in any combination, to further describe the chromium compound of the heteroatomic ligand chromium compound complex, and can be utilized without limitation, and in any combination with $L^{1s}$, $X^{1s}$, $X^{2s}$, $R^{1s}$, $R^{2s}$, m, and n of the heteroatomic ligand to further describe the heteroatomic ligand chromium compound complexes contemplated herein.

Each $X^{1s}$ and each $X^{2s}$ of any heteroatomic ligand described herein or any heteroatomic ligand of any heteroatomic ligand chromium compound complex described herein having an $X^{1s}$ and/or $X^{2s}$ can be independently selected from N, P, O, and S; alternatively, independently selected from N and P; or alternatively, independently selected from O and S. In some aspects, each $X^{1s}$ and each $X^{2s}$ can be N; alternatively, P; alternatively O; or alternatively S. Each m and each n of any heteroatomic ligand described herein or any heteroatomic ligand of any heteroatomic ligand chromium compound complex described herein having an m and/or n can be independently selected from 1 or 2; alternatively, 1; or alternatively, 2. Is some particular aspects, each m and/or each n can be 1 when $X^{1s}$ and/or $X^{2s}$, respectively, is O or S; alternatively, O; or alternatively, S. In some other particular aspects, each m and/or each n can be 2 when $X^{1s}$ and/or $X^{2s}$, respectively, is N or P; alternatively, N; or alternatively, P.

In a non-limiting aspect, the heteroatomic ligand can have the formula $R^{1s}S(L^{1s})SR^{2s}$, $(R^{1s})_2P(L^{1s})P(R^{2s})_2$, or $(R^{1s})_2N(L^{1s})N(R^{2s})_2$; alternatively, $R^{1s}S(L^{1s})SR^{2s}$; alternatively, $(R^{1s})_2P(L^{1s})P(R^{2s})_2$; or alternatively, $(R^{1s})_2N(L^{1s})NP(R^{2s})_2$ while heteroatomic ligand chromium compound complex can have any one of the formulas

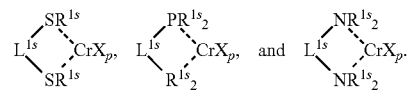

In non-limiting aspects where the heteroatomic ligand or the heteroatomic ligand of the heteroatomic ligand chromium compound complex has two linked heteroatomic groups, the heteroatomic ligand can have the formula selected from one or more of

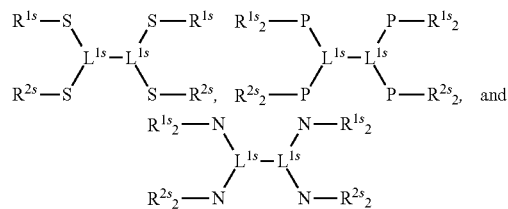

while the heteroatomic ligand chromium compound complex can have any one of the formulas

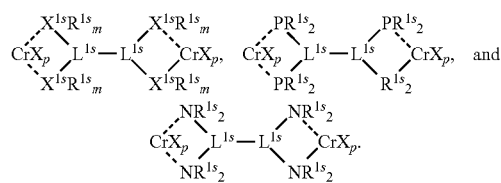

In an aspect, each $L^{1s}$ of any heteroatomic ligand described herein or any heteroatomic ligand of the heteroatomic ligand chromium compound complex described herein independently can be any group capable of linking group $X^{1s}$ and $X^{2s}$. In some aspects, each $L^{1s}$ independently can be an organylene group, an amin-di-yl group, or a phosphin-di-yl group; alternatively, an organylene group consisting of inert functional groups, an amin-di-yl group, or a phosphin-di-yl group; alternatively, a hydrocarbylene group, an amin-di-yl group, or a phosphin-di-yl group; alternatively an amin-di-yl group or a phosphin-di-yl group; alternatively, an organylene group; alternatively, an organylene group consisting of inert functional groups; alternatively, a hydrocarbylene group; alternatively, an amin-di-yl group; or alternatively, a phosphin-di-yl group. In an aspect, the $L^{1s}$ organylene group that can be utilized as $L^{1s}$ can be a $C_1$ to $C_{20}$, a $C_1$ to $C_{15}$, a $C_1$ to $C_{10}$, or, a $C_1$ to $C_5$ organylene group. In an aspect, the $L^{1s}$ organylene group consisting of inert functional groups that can be utilized as $L^{1s}$ can be a $C_1$ to $C_{20}$, a $C_1$ to $C_{15}$, a $C_1$ to $C_{10}$, or, a $C_1$ to $C_5$ organylene group consisting of inert functional groups. In an aspect, the $L^{1s}$ hydrocarbylene group that can be utilized as $L^{1s}$ can be a $C_1$ to $C_{20}$, a $C_1$ to $C_{15}$, a $C_1$ to $C_{10}$, or a $C_1$ to $C_5$ hydrocarbylene group. In an aspect, the amin-di-yl group that can be utilized as $L^{1s}$ can be a $C_1$ to $C_{30}$, a $C_1$ to $C_{20}$, a $C_1$ to $C_{15}$, or a $C_1$ to $C_{10}$ amin-di-yl group. In an aspect, the phosphin-di-yl group that can be utilized as $L^{1s}$ can be a $C_1$ to $C_{30}$, a $C_1$ to $C_{20}$, a $C_1$ to $C_{15}$, or a $C_1$ to $C_{10}$ phosphin-di-yl group.

In an aspect, the each organylene $L^{1s}$ group can have the formula -($L^{3s}$)$NR^5$($L^{4s}$)- or -($L^{3s}$)$PR^5$($L^{4s}$)-; alternatively, -($L^{3s}$)$NR^5$($L^{4s}$)-; or alternatively, -($L^{3s}$)$PR^5$($L^{4s}$)-. In an aspect, the each amin-di-yl group can have the formula —N($R^5$)—. In an aspect, each phosphin-di-yl group can have the formula —P($R^5$)—. In these $L^{1s}$ group formulas, the dashes represent the undesignated valance to which the $X^{1s}$ and $X^{2s}$ of the heteroatomic ligand described herein or the heteroatomic ligand of the heteroatomic ligand of the heteroatomic ligand chromium compound complex described herein attach. In some non-limiting aspects, the heteroatomic ligand can have Structure PNP1, Structure PNP2, Structure NRN, Structure PRP, Structure SRN, Structure PRN, and Structure NRP; alternatively, Structure PNP1 or Structure PNP2; alternatively, Structure PRP, Structure SRN, or Structure PRN; alternatively, Structure PNP1; alternatively, Structure PNP2; alternatively, Structure NRN; alternatively, Structure PRP; alternatively, Structure SRN; alternatively, Structure PRN; or alternatively, Structure NRP. In some non-limiting aspects, the heteroatomic ligand chromium compound complex having a heteroatomic ligand $(R^{1s})_m X^{1s}(L^{1s})X^{2s}(R^{2s})_n$ which can be utilized in catalyst systems described herein can have Structure PNPCr1, Structure PNPCr2, Structure NRNCr, Structure PRPCr, Structure SRNCr, Structure PRNCr, and Structure NRPCr; alternatively, Structure PNPCr1 or Structure PNPCr2; alternatively, Structure PRPCr, Structure SRNCr, or Structure PRNCr; alternatively, Structure PNPCr1; alternatively, Structure PNPCr2; alternatively, Structure NRNCr; alternatively, Structure PRPCr; alternatively, Structure SRNCr; alternatively, Structure PRNCr; or alternatively, Structure NRPCr.

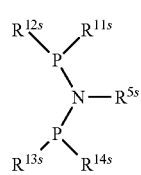

Structure PNP1

-continued

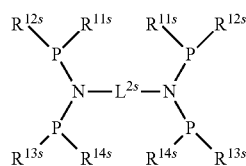

Structure PNP2

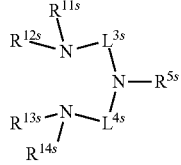

Structure NRN

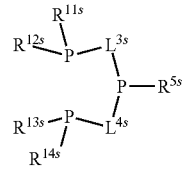

Structure PRP

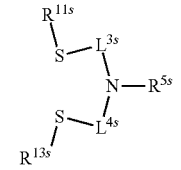

Structure SRN

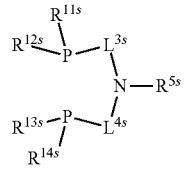

Structure PRN

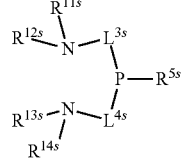

Structure NRP

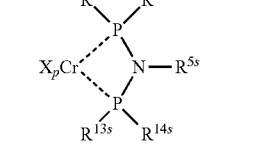

Structure PNPCr1

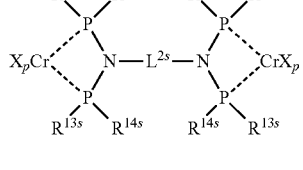

Structure PNPCr2

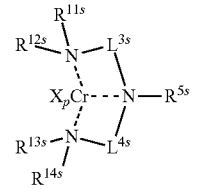

Structure NRNCr

-continued

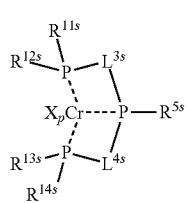
Structure PRPCr

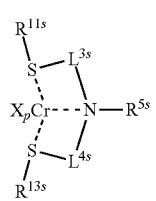
Structure SRNCr

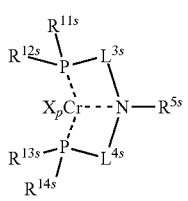
Structure PRNCr

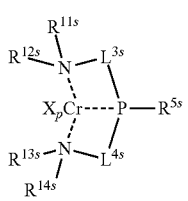
Structure NRPCr $R^{5s}$, $L^{2s}$, $L^{3s}$, $L^{4s}$, $R^{11s}$, $R^{12s}$, $R^{13s}$, and $R^{14s}$ are each independent elements of any of the organylene groups described herein, any of the amin-di-yl groups described herein, any of the phosphin-di-yl groups described herein, any of the heteroatomic ligands having Structure PNP1, Structure PNP2, Structure NRN, Structure PRP, Structure SRN, Structure PRN, and Structure NRP, and any heteroatomic ligand portion of the heteroatomic ligand chromium compound complexes having Structure PNCr1, Structure PNPCr2, Structure NRNCr, Structure PRPCr, Structure SRNCr, Structure PRNCr, and Structure NRPCr in which they occur and are independently described herein. The independent descriptions of $R^{5s}$, $L^{2s}$, $L^{3s}$, $L^{4s}$, $R^{11s}$, $R^{12s}$, $R^{13s}$, and $R^{14s}$ can be utilized without limitation, and in any combination, to further describe any of the organylene groups described herein, any of the amin-di-yl groups described herein, any of the phosphin-di-yl groups described herein, any heteroatomic ligand structure provided herein, and/or any heteroatomic ligand chromium compound complex structure provided herein in which they occur. Similarly, $CrX_p$ is an independent element of the heteroatomic ligand chromium compound complexes having Structure PNCr1, Structure PNPCr2, Structure NRNCr, Structure PRPCr, Structure SRNCr, Structure PRNCr, and Structure NRPCr and is independently described herein. The independent description of $CrX_p$ can be utilized without limitation, and in any combination, to further describe the chromium compound portion of any heteroatomic ligand chromium compound complex described herein and/or any heteroatomic ligand chromium compound complex structure provided herein. Additionally, the independent description of $CrX_p$ can be utilized without limitation, and in any combination, with the independently described $R^{5s}$, $L^{2s}$, $L^{3s}$, $L^{4s}$, $R^{11s}$, $R^{12s}$, $R^{13s}$, and $R^{14s}$ provided herein to further describe any heteroatomic ligand chromium compound complex structure provided herein.

Generally, each $R^{1s}$, $R^{2s}$, $R^{11s}$, $R^{12s}$, $R^{13s}$, and $R^{14s}$ of any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein having a $R^{1s}$, $R^{2s}$, $R^{11s}$, $R^{12s}$, $R^{13s}$, and $R^{14s}$ independently can be an organyl group; alternatively, an organyl group consisting of inert functional groups; or alternatively, a hydrocarbyl group. In an aspect, the organyl group which can be utilized as $R^{1s}$, $R^{2s}$, $R^{11s}$, $R^{12s}$, $R^{13s}$, and $R^{14s}$ can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{1s}$, $R^{2s}$, $R^{11s}$, $R^{12s}$, $R^{13s}$, and/or $R^{14s}$ can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{1s}$, $R^{2s}$, $R^{11s}$, $R^{12s}$, $R^{13s}$, and/or $R^{14s}$ can be a $C_1$ to $C_{20}$, a $C_1$ to $C_{15}$, a $C_1$ to $C_{10}$, or a $C_1$ to $C_5$ hydrocarbyl group. In further aspects, $R^{1s}$ and $R^{2s}$, $R^{11s}$ and $R^{12s}$, and/or $R^{13s}$ and $R^{14s}$ can be joined to form a ring or a ring system.

In an aspect, each $R^{1s}$, $R^{2s}$, $R^{11s}$, $R^{12s}$, $R^{13s}$, and $R^{14s}$ of any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein having a $R^{1s}$, $R^{2s}$, $R^{11s}$, $R^{12s}$, $R^{13s}$, and/or $R^{14s}$ independently can be independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, each $R^{1s}$, $R^{2s}$, $R^{11s}$, $R^{12s}$, $R^{13s}$, and $R^{14s}$ of any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein having a $R^{1s}$, $R^{2s}$, $R^{11s}$, $R^{12s}$, $R^{13s}$, and/or $R^{14s}$ independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, each alkyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{10}$, or a $C_1$ to $C_5$ alkyl group. In any aspect or embodiment disclosed herein, each substituted alkyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{10}$, or a $C_1$ to $C_5$ substituted alkyl group. In any aspect or embodiment disclosed herein, each cycloalkyl group which can be utilized as $R^{1s}$, $R^{2s}$, $R^{11s}$, $R^{12s}$, $R^{13s}$, and/or $R^{14s}$ independently can be a $C_4$ to $C_{20}$, a $C_4$ to $C_{15}$, or a $C_4$ to $C_{10}$ cycloalkyl group. In any aspect or embodiment disclosed herein, each substituted cycloalkyl group which can be utilized as $R^{1s}$, $R^{2s}$, $R^{11s}$, $R^{12s}$, $R^{13s}$, and/or $R^{14s}$ independently can be a $C_4$ to $C_{20}$, a $C_4$ to $C_{15}$, or a $C_4$ to $C_{10}$ substituted cycloalkyl group. In any aspect or embodiment disclosed herein, each aryl group which can be utilized as $R^{1s}$, $R^{2s}$, $R^{11s}$, $R^{12s}$, $R^{13s}$, and/or $R^{14s}$ independently can be a $C_6$ to $C_{20}$, a $C_6$ to $C_{15}$, or a $C_6$ to $C_{10}$ aryl group. In any aspect or embodiment disclosed herein, each substituted aryl group which can be utilized as $R^{1s}$, $R^{2s}$, $R^{11s}$, $R^{12s}$, $R^{13s}$, and/or $R^{14s}$ independently can be a $C_6$ to $C_{20}$, a $C_6$ to $C_{15}$, or a $C_6$ to $C_{10}$ substituted aryl group. In any aspect or embodiment disclosed herein, each aralkyl group which can be utilized as $R^{1s}$, $R^{2s}$, $R^{11s}$, $R^{12s}$, $R^{13s}$, and/or $R^{14s}$ independently can be a $C_7$ to $C_{20}$, a $C_7$ to $C_{15}$, or a $C_7$ to $C_{10}$ aralkyl group. In any aspect or embodiment disclosed herein, each substituted aryl group which can be utilized as $R^{1s}$, $R^{2s}$, $R^{11s}$, $R^{12s}$, $R^{13s}$, and/or $R^{14s}$ independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe a substituted group (general or specific) which can be utilized $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a methyl group, an ethyl group, a propyl group, a butyl group, a pentyl group, a hexyl group, a heptyl group, or an octyl group; alternatively, a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some aspects, the alkyl groups which can be utilized as each $R^{1s}$, $R^{2s}$, $R^{11s}$, $R^{12s}$, $R^{13s}$, and $R^{14s}$ independently can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for any of $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted cyclohexyl group, a 2,6-disubstituted cyclohexyl group, a 2-substituted cyclopentyl group, or a 2,6-disubstituted cyclopentyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-substituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-substituted cyclopentyl group; or alternatively, a 2,6-disubstituted cyclopentyl group. In an aspect, one or more substituents of a multi-substituted cycloalkyl group utilized as $R^{1s}$, $R^{2s}$, $R^{11s}$, $R^{12s}$, $R^{13s}$, and/or $R^{14s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{11s}$, $R^{12s}$, $R^{13s}$, and/or $R^{14s}$. Generally, the alkyl substituents of a disubstituted cyclohexyl or cyclopentyl group can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group or a substituted phenyl group; alternatively, a phenyl group; or alternatively, a substituted phenyl group. In an aspect, the substituted phenyl group which can be utilized for each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^{1s}$, $R^{2s}$, $R^{11s}$, $R^{12s}$, $R^{13s}$, and/or $R^{14s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 4-alkylphenyl group; alternatively, a 2,4-dialkylphenyl group; alternatively, a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{11s}$, $R^{12s}$, $R^{13s}$, and/or $R^{14s}$. Generally, the alkyl substituents of dialkylphenyl groups (general or specific) or trialkylphenyl groups (general or specific) can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-alkoxyphenyl group, or a 4-alkoxyphenyl group.

In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group.

In a non-limiting aspect, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-halophenyl group, a 4-halophenyl group, or a 2,6-dihalophenyl group. Generally, the halides of a dihalophenyl group can be the same, or alternatively, the halides can be different. In some aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-fluorophenyl group, a 4-fluorophenyl group, or a 2,6-difluorophenyl group.

In an aspect, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a benzyl group or a substituted benzyl group; alternatively, a benzyl group; or alternatively, a substituted benzyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{11s}$, $R^{12s}$, $R^{13s}$, and/or $R^{14s}$.

Generally, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be an organyl group; alternatively, an organyl group consisting of inert functional groups; or alternatively, a hydrocarbyl group. In an aspect, the organyl group which can be utilized as $R^{5s}$ can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{5s}$ can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{5s}$ can be a $C_1$ to $C_{20}$, a $C_1$ to $C_{15}$, a $C_1$ to $C_{10}$, or a $C_1$ to $C_5$ hydrocarbyl group.

In an aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be an alkyl group, a substituted alkyl group, a cycloalkyl group, a substituted cycloalkyl group, an aryl group, a substituted aryl group, an aralkyl group, or a substituted aralkyl group. In some aspects, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect or embodiment disclosed herein, the alkyl group which can be utilized as $R^{5s}$ can be a $C_1$ to $C_{20}$, a $C_1$ to $C_{15}$, or a $C_1$ to $C_{10}$ alkyl group. In any aspect or embodiment disclosed herein, the substituted alkyl group which can be utilized as $R^{5s}$ can be a $C_1$ to $C_{20}$, a $C_1$ to $C_{15}$, or a $C_1$ to $C_{10}$ substituted alkyl group. In any aspect or embodiment disclosed herein, the cycloalkyl group which can be utilized as $R^{5s}$ can be a $C_4$ to $C_{20}$, a $C_4$ to $C_{15}$, or a $C_4$ to $C_{10}$ cycloalkyl group. In any aspect or embodiment disclosed herein, the substituted cycloalkyl group which can be utilized as $R^{5s}$ can be a $C_4$ to $C_{20}$, a $C_4$ to, or a $C_4$ to $C_{10}$ substituted cycloalkyl group. In any aspect or embodiment disclosed herein, the aryl group which can be utilized as $R^{5s}$ can be a $C_6$ to $C_{20}$, a $C_6$ to $C_{15}$, or a $C_6$ to $C_{10}$ aryl group. In any aspect or embodiment disclosed herein, the substituted aryl group which can be utilized as $R^{5s}$ can be a $C_6$ to $C_{20}$, a $C_6$ to $C_{15}$, or a $C_6$ to $C_{10}$ substituted aryl group. In any aspect or embodiment disclosed herein, each aralkyl group which can be utilized as $R^{5s}$ can be a $C_7$ to $C_{20}$, a $C_7$ to $C_{15}$, or a $C_7$ to $C_{10}$ aralkyl group. In any aspect or embodiment disclosed herein, the substituted aryl group which can be utilized as $R^{5s}$ can be a $C_7$ to $C_{20}$, a $C_7$ to $C_{15}$, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted group (general or specific) which can be utilized $R^{5s}$.

In an aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a methyl group, an ethyl group, a propyl group, a butyl group, a pentyl group, a hexyl group, a heptyl group, or an octyl group; alternatively, a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; alternatively, a methyl group, an ethyl group, an iso-propyl (2-propyl) group, a tert-butyl (2-methyl-2-propyl) group, or a neopentyl (2,2-dimethyl-1-propyl) group; alternatively, a methyl group; alternatively, an ethyl group; alternatively, a n-propyl (1-propyl) group; alternatively, an iso-propyl (2-propyl) group; alternatively, a tert-butyl (2-methyl-2-propyl) group; or alternatively, a neopentyl (2,2-dimethyl-1-propyl) group. In some aspects, the alkyl groups which can be utilized as $R^{5s}$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a cyclopentyl group, a substituted cyclopentyl group, a cyclohexyl group, a substituted cyclohexyl group; alternatively, a cyclopentyl group or a substituted cyclopentyl group; alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In further aspects, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a 2-substituted cyclohexyl group, a 2,6-disubstituted cyclohexyl group, a 2-subsituted cyclopentyl group, or a 2,6-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-substituted cyclopentyl group or a 2,6-disubstituted cyclopentyl group; alternatively, a 2-substituted cyclohexyl group or a 2-subsituted cyclopentyl group; alternatively, a 2,6-disubstituted cyclohexyl group or a 2,6-disubstituted cyclopentyl group; alternatively, a 2-substituted cyclohexyl group; alternatively, a 2,6-disubstituted cyclohexyl group; alternatively, a 2-subsituted cyclopentyl group; or alternatively, a 2,6-disubstituted cyclopentyl group. In an aspect, one or more substituents of a multi-substituted cycloalkyl group utilized as $R^{5s}$ can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting aspects, $R^{5s}$ heteroatomic ligand structure provided herein, and/or any heteroatomic ligand chromium compound complex structure provided herein can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an aspect, $R^{5s}$ heteroatomic ligand structure provided herein, and/or any heteroatomic ligand chromium compound complex structure provided herein can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a phenyl group or a substituted phenyl group; alternatively, a phenyl group; or alternatively, a substituted phenyl group. In some aspects, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; alternatively, a 2,4-disubstituted phenyl group; alternatively, a 2,6-disubstituted phenyl group; or alternatively, a 2,4,6-trisubstituted phenyl group. In an aspect, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$.

In a non-limiting aspect, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5s}$. Generally, the alkyl substituents of dialkylphenyl groups (general of specific) or trialkylphenyl groups (general or specific) can be the same, or alternatively, the alkyl substituents can be different. In some non-limiting aspects, $R^{5s}$ of any organylene $L^{1s}$ group disclosed herein, any amin-di-yl group disclosed herein, any phosphin-di-yl group disclosed herein, any heteroatomic ligand structure provided herein, and/or any heteroatomic ligand chromium compound complex structure provided herein can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{2s}$ of the heteroatomic ligand having Structure PNP2 and/or the heteroatomic ligand chromium compound complex having Structure PNPCr2 can be an organylene group; alternatively, an organylene group consisting of inert functional groups; or alternatively, a hydrocarbylene group. In an aspect, the organylene group which can be utilized as $L^{2z}$ can be a $C_1$ to $C_{20}$, a $C_1$ to $C_{15}$, or a $C_1$ to $C_{10}$ organylene group. In an aspect, the organylene group consisting of inert functional groups which can be utilized as $L^{2s}$ can be a $C_1$ to $C_{20}$, a $C_1$ to $C_{15}$, or a $C_1$ to $C_{10}$ organylene group consisting of inert functional groups. In an aspect, the hydrocarbylene group which can be utilized as $L^{2s}$ can be a $C_1$ to $C_{20}$, a $C_1$ to $C_{15}$, or a $C_1$ to $C_{10}$ hydrocarbylene group. In an aspect, $L^{1s}$ of the heteroatomic ligand having Structure PNP2 and/or the heteroatomic ligand chromium compound complex having Structure PNPCr2 can be a $C_1$ to $C_{20}$, $C_1$ to $C_{15}$, or a $C_1$ to $C_{10}$ alkylene group.

In an aspect, $L^{2s}$ of the heteroatomic ligand having Structure PNP2 and/or the heteroatomic ligand chromium compound complex having Structure PNPCr2 can be —(CR$^P$R$^{P'}$)$_m$— where each R$^P$ and R$^{P'}$ can independently be hydrogen, methyl, ethyl, propyl, isopropyl, or butyl groups and m can be an integer from 1 to 12. In some aspects, $L^{2s}$ of the heteroatomic ligand having Structure PNP2 and/or the heteroatomic ligand chromium compound complex having Structure PNPCr2 can be a methylene group (—CH$_2$—), an ethylene group (—CH$_2$CH$_2$—), a propylene group (—CH$_2$CH$_2$CH$_2$—), a —CH(CH$_3$)CH$_2$— group, —C(CH$_3$)$_2$— group, a butylene group (—CH$_2$CH$_2$CH$_2$—CH$_2$—), or a —CH$_2$CH(CH$_3$)—CH$_2$— group. In other aspects, $L^{2s}$ of the heteroatomic ligand having Structure PNP2 and/or the heteroatomic ligand chromium compound complex having Structure PNPCr2 can be a methylene group (—CH$_2$—), an ethylene group (—CH$_2$CH$_2$—), or a —CH(CH$_3$)CH$_2$— group; alternatively, a methylene group (—CH$_2$—); alternatively, an ethylene group (—CH$_2$CH$_2$—); alternatively, a propylene group (—CH$_2$CH$_2$CH$_2$—); alternatively, a —CH(CH$_3$)CH$_2$— group; alternatively, a —C(CH$_3$)$_2$— group; or alternatively, a —CH$_2$CH(CH$_3$)—CH$_2$— group.

In an aspect, $L^{2s}$ of the heteroatomic ligand having Structure PNP2 and/or the heteroatomic ligand chromium compound complex having Structure PNPCr2 can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)-methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)propane, a substituted 1,2-bis(3-cyclohexylene)propane, 1,2-bis(4-cyclohexylene)propane, a substituted 1,2-bis(4-cyclohexylene)-propane, 2,2-bis(3-cyclohexylene)propane, a substituted 2,2-bis(3-cyclohexylene)propane, 2,2-bis(4-cyclohexylene)propane, or a substituted 2,2-bis(4-cyclohexylene)propane. In some aspects, $L^{2s}$ of the heteroatomic ligand having Structure PNP2 and/or the heteroatomic ligand chromium compound complex having Structure PNPCr2 can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane. In an aspect, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{2s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{2s}$.

In an aspect, $L^{2s}$ of the heteroatomic ligand having Structure PNP2 and/or the heteroatomic ligand chromium compound complex having Structure PNPCr2 can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some aspects, $L^{2s}$ of the heteroatomic ligand having Structure PNP2 and/or the heteroatomic ligand chromium compound complex having Structure PNPCr2 can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane. In an aspect, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$.

Generally, $L^{3s}$ and $L^{4s}$ of any organylene $L^{1s}$ group disclosed herein, any heteroatomic ligand structure provided herein, and/or any heteroatomic ligand chromium compound complex structure provided herein independently can be an organylene group; alternatively, an organylene group consisting of inert functional groups; or alternatively, a hydrocarbylene group. In an aspect, the organylene group which can be utilized as $L^{3s}$ and/or $L^{4s}$ can be a $C_1$ to $C_{20}$, a $C_1$ to $C_{15}$, or a $C_1$ to $C_{10}$ organylene group. In an aspect, the organylene group consisting of inert functional groups which can be utilized as $L^{3s}$ and/or $L^{4s}$ can be a $C_1$ to $C_{20}$, a $C_1$ to $C_{15}$, or a $C_1$ to $C_{10}$ organylene group consisting of inert functional groups. In an aspect, the hydrocarbylene group which can be utilized as $L^{3s}$ and/or $L^{4s}$ can be a $C_1$ to $C_{20}$, a $C_1$ to $C_{15}$, or a $C_1$ to $C_{10}$ hydrocarbylene group. In an aspect, $L^{3s}$ and $L^{4s}$ of any organylene $L^{1s}$ group disclosed herein, any heteroatomic ligand structure provided herein, and/or any heteroatomic ligand chromium compound complex structure provided herein independently can be a $C_1$ to $C_{20}$, $C_1$ to $C_{15}$, or a $C_1$ to $C_{10}$ alkylene group.

In an aspect, $L^{3s}$ and $L^{4s}$ of any organylene $L^{1s}$ group disclosed herein, any heteroatomic ligand structure provided herein, and/or any heteroatomic ligand chromium compound complex structure provided herein independently can be —$(CR^P R^{P'})_m$— where each $R^P$ and $R^{P'}$ can independently be hydrogen, methyl, ethyl, propyl, isopropyl, or butyl groups and m can be an integer from 1 to 12. In some aspects, $L^{3s}$ and $L^{4s}$ of any organylene $L^{1s}$ group disclosed herein, any heteroatomic ligand structure provided herein, and/or any heteroatomic ligand chromium compound complex structure provided herein independently can be a methylene group (—$CH_2$—), an eth-1,2-ylene group (—$CH_2CH_2$—), an ethen-1,2-ylene group (—CH═CH—), a prop-1,3-ylene group (—$CH_2CH_2CH_2$—), a prop-1,2-ylene group (—CH($CH_3$)$CH_2$—), a prop-2,2-ylene group (—C($CH_3$)$_2$—), a 1-methylethen-1,2-ylene group (—C($CH_3$)═CH—), a but-1,4-ylene group (—$CH_2CH_2CH_2CH_2$—), a but-1,3-ylene group (—$CH_2CH_2$CH($CH_3$)—), a but-2,3-ylene group (—CH($CH_3$)CH($CH_3$)—), a but-2-en-2,3-ylene group (—C($CH_3$)C($CH_3$)—), a 3-methylbut-1,3-ylene group (—$CH_2CH_2$C($CH_3$)$_2$—), a 1,2-cyclopentylene group, a 1,2-cyclohexylene group, or a phen-1,2-ylene group; alternatively, a methylene group (—$CH_2$—), an eth-1,2-ylene group (—$CH_2CH_2$—), a prop-1,3-ylene group (—$CH_2CH_2CH_2$—), a prop-1,2-ylene group (—CH($CH_3$)$CH_2$—), a prop-2,2-ylene group (—C($CH_3$)$_2$—), a but-1,4-ylene group (—$CH_2CH_2CH_2$—$CH_2$—), a but-1,3-ylene group (—$CH_2CH_2$CH($CH_3$)—), a but-2,3-ylene group (—CH($CH_3$)CH($CH_3$)—), a 1,2-cyclopentylene group, a 1,2-cyclohexylene group, or a phen-1,2-ylene group; alternatively, an eth-1,2-ylene group (—$CH_2CH_2$—), a prop-1,3-ylene group (—$CH_2CH_2CH_2$—), a prop-1,2-ylene group (—CH($CH_3$)$CH_2$—), a but-1,3-ylene group (—$CH_2CH_2$CH($CH_3$)—), a but-2,3-ylene group (—CH($CH_3$)CH($CH_3$)—), a 1,2-cyclopentylene group, a 1,2-cyclohexylene group, or a phen-1,2-ylene group. In some aspects, $L^{3s}$ and $L^{4s}$ of any organylene $L^{1s}$ group disclosed herein, any heteroatomic ligand structure provided herein, and/or any heteroatomic ligand chromium compound complex structure provided herein independently can be an eth-1,2-ylene group (—$CH_2CH_2$—); alternatively, a prop-1,3-ylene group (—$CH_2CH_2CH_2$—); alternatively, a prop-1,2-ylene group (—CH($CH_3$)$CH_2$—); alternatively, a but-1,3-ylene group (—$CH_2CH_2$CH($CH_3$)—); alternatively, a but-2,3-ylene group (—CH($CH_3$)CH($CH_3$)—); alternatively, a 1,2-cyclopentylene group; alternatively, a 1,2-cyclohexylene group; or alternatively, a phen-1,2-ylene group.

While not shown, one of ordinary skill in the art will recognize that a neutral ligand can be associated with the chromium compounds or heteroatomic ligand chromium compound complexes described herein. Additionally it should be understood that while chromium compounds or heteroatomic ligand chromium compound complexes provided herein do not formally show the presence of a neutral ligand, the chromium compounds or heteroatomic ligand chromium compound complexes having neural ligands (e.g., nitriles and ethers, among others) are fully contemplated as potential chromium compounds or heteroatomic ligand chromium compound complexes that can be utilized in the catalyst system used in aspects and embodiments of the herein described inventions.

In a non-limiting aspect, the heteroatomic ligand can be any one or more of HL 1, HL 2, HL 3, HL 4. HL 5, HL 6, HL 7, HL 7, and HL 9. In some non-limiting aspects, the diphosphino amine transition metal compound complex can be a chromium compound complex of any one or more of HLCr 1, HLCr 2, HLCr 3, HLCr 4, HLCr 5, HLCr 6, HLCr 7, HLCr 8, and HLCr 9. In other non-limiting aspects, the diphosphino amine transition metal compound complex can be a chromium(III) chloride or chromium(III) acetylacetonate complex of any one or more of HLCr 1, HLCr 2, HLCr 3, HLCr 4, HLCr 5, HLCr 6, HLCr 7, HLCr 8, and HLCr 9.

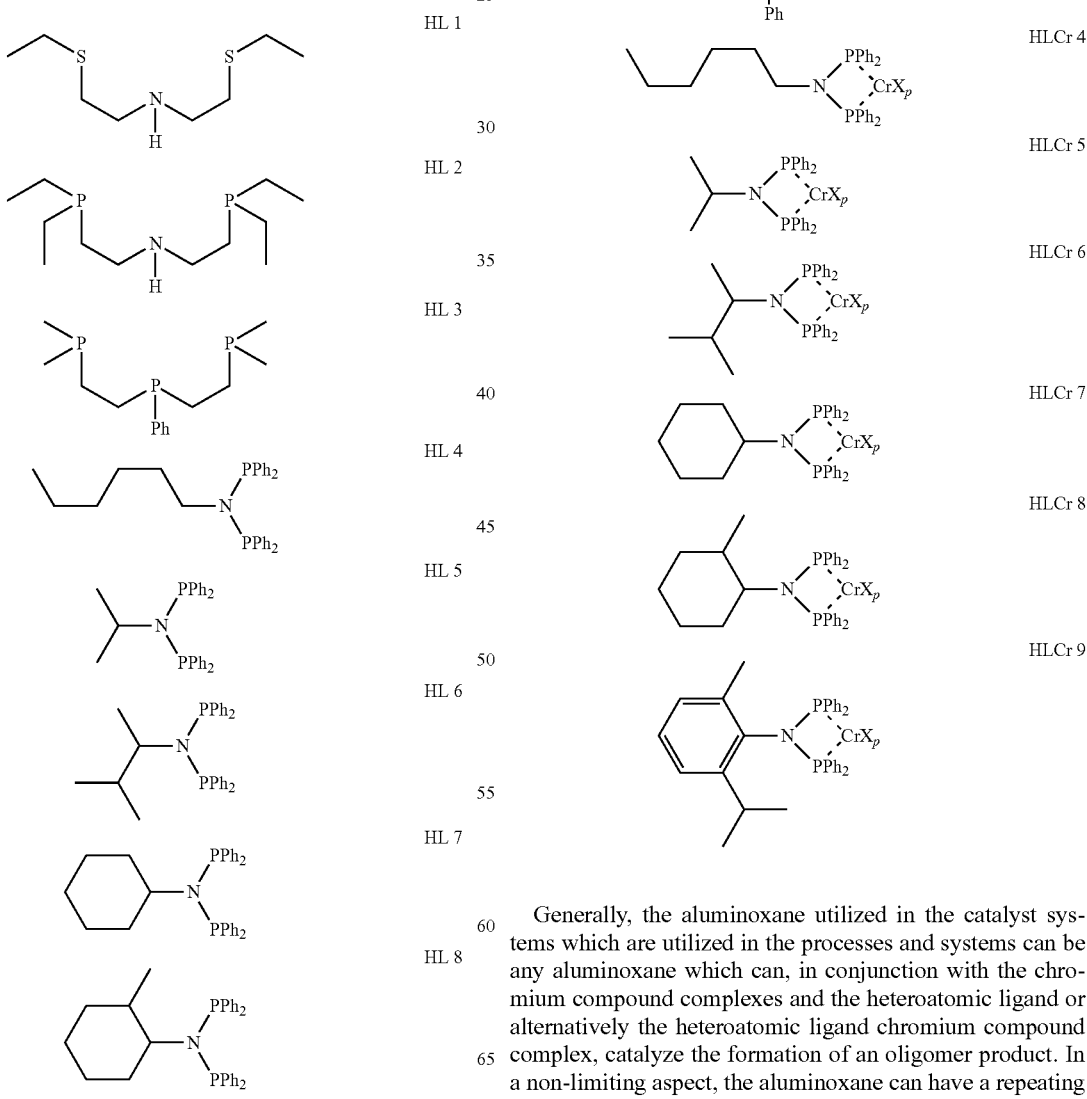

Generally, the aluminoxane utilized in the catalyst systems which are utilized in the processes and systems can be any aluminoxane which can, in conjunction with the chromium compound complexes and the heteroatomic ligand or alternatively the heteroatomic ligand chromium compound complex, catalyze the formation of an oligomer product. In a non-limiting aspect, the aluminoxane can have a repeating unit characterized by the Formula I:

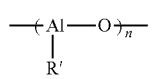

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an aspect, n can range from 2 to 15; or alternatively, range from 3 to 10.

In an aspect, each alkyl group of the aluminoxane independently can be, comprise, or consist essentially of, a $C_1$ to $C_{20}$ alkyl group; alternatively, a $C_1$ to $C_{10}$ alkyl group; or alternatively, a $C_1$ to $C_6$ alkyl group. In an aspect, each alkyl group of the aluminoxane independently can be, comprise, or consist essentially of, a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some aspects, each alkyl group or the aluminoxane independently can be, comprise, or consist essentially of, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In a non-limiting aspect, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, or mixtures thereof. In some non-limiting aspects, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentyl-aluminoxane.

The processes and systems (e.g., systems 100, 200, and/or 300) described herein can provide various advantages.

One advantage of the disclosure is that the disclosed processes and systems can provide a curtain of inert material along outer surface 113 of end 112 of reactor inlet 110. The curtain can provide a flow of the inert material such that a coaxial layer of the inert material is present on outer surface 113 of reactor inlet 110. The coaxial layer formed by the curtain can provide a boundary layer of flowing material which can prevent any fouling particles from adhering to outer surface 113 of reactor inlet 110. For any fouling particles that do adhere to outer surface 113, for example, due to intermittent flow of the inert material and accumulation of fouling particles during a no-flow period, the re-started flow of the inert material can sweep away the fouling particles which have accumulated on outer surface 113.

Another advantage of the disclosed processes and systems is that the cloud of concentrated reactant which forms at the end of the reactor inlet is disturbed and/or formation is prevented by the inert material curtain, which flows along outer surface 113 of reactor inlet 110. Without a concentrated cloud of reactant, reactions at the end of the reactor inlet are reduced and the accumulation of fouling particles (e.g., polymer) can be prevented.

Another advantage is that use of inlet sleeve 150 in combination with reactor inlet 110 is a cost-effective solution for reducing and/or minimizing fouling of reactor inlet 110. The material of construction of inlet sleeve 150 can be the same as reactor inlet 110, and inlet sleeve 150 has no moving parts which need maintenance and/or can fail.

Another advantage is that by preventing and/or reducing the accumulation of fouling material on end 112 of reactor inlet 110, run times (or, operating times) for the reaction(s) in reactor 101 can be prolonged, since problematic fouling levels on reactor inlet 110 are reduced and any accumulation of fouling material either occurs over a longer period of time or does not occur during the time reactor 101 is operated.

Another advantage is that the configuration of reactor inlet 110 relative to inlet sleeve 150 can have various orientations such as those shown in FIGS. 3 to 5. The different orientations (e.g., neutral orientation of FIG. 3, positive orientation of FIG. 4, negative orientation of FIG. 5) can allow for application in a variety of reactor shapes and process flow configurations. For example, the positive orientation may be desirable when space is limited for process flow around inlet sleeve 150. Neutral orientation may be desirable when part of all of the process flow is tangential to the flow of the inert material along outer surface 113 of reactor inlet 110. Negative orientation may be desirable when mixing of the inert material and reactant is desirable before joining the process flow. These scenarios are exemplary only and it is not intended that neutral, positive, and negative orientations be limited to the above described applications.

Another advantage that can be realized by the processes and systems described herein is that inlet sleeve 150/reactor inlet 110 configuration can be utilized in combination with other foul mitigation techniques shown in FIGS. 10 to 12, where an inert material (same or different than the inert material which flows in annular space 156) can be fed to the reactor 101 and mixed with the reactant. Thus, the techniques in FIGS. 10 to 12 not only reduce the concentration of the reactant flowing in reactor 101 via the reactor inlet 110, but the curtain of inert material operates in tandem with the reduced concentration of reactant to prevent formation of product which can accumulate on end 112 of reactor inlet 110.

In respect to selective ethylene oligomerization which utilizes techniques shown in one of FIGS. 10 to 12 with the inlet sleeve 150/reactor inlet 110 of one of FIGS. 3 to 5, another advantage is the mass of polymer (e.g., polyethylene in contrast to desired oligomers of ethylene) per mass of oligomer in the reactor 101 can be reduced (or alternatively can be less than a mass of polymer per mass of oligomer product formed) as compared to otherwise similar processes and systems which do not utilize inlet sleeve 150 and which do not contact ethylene with at least a portion of the diluent prior to contact of ethylene with the catalyst systems disclosed herein.

ADDITIONAL DISCLOSURE

The following is provided as additional disclosure for combinations of features and aspects of the present invention.

Aspect 1 is a process to prevent fouling at a reactor inlet, the process comprising:
flowing a reactant into a reactor via the reactor inlet such that the reactant is introduced to an interior of the reactor via an end of the reactor inlet; and
flowing an inert material into the reactor coaxially with respect to an outer surface of the end of the reactor inlet.

Aspect 2 is the process of aspect 1, wherein the reactant is a first petrochemical, and wherein the inert material is selected from a second petrochemical, nitrogen, argon, or a combination thereof.

Aspect 3 is the process of any one of aspects 1-2, wherein the reactor is an oligomerization reactor, wherein the reactant is an olefin, and wherein the inert material is a diluent with respect to an oligomerization reaction in the reactor.

Aspect 4 is the process of any one of aspects 1-3, wherein the end of the reactor inlet extends into the interior of the reactor, and wherein an end of an inlet sleeve extends into the interior of the reactor.

Aspect 5 is the process of any one of aspects 1-4, further comprising:
flowing diluent into the reactor via the reactor inlet such that a mixture of the reactant and diluent is introduced to the interior of the reactor via the end of the reactor inlet,
wherein the diluent which flows into the reactor via the reactor inlet is a primary source of diluent for a reaction in the reactor, and
wherein the inert material which flows coaxially into the reactor is a secondary source of diluent for the reaction in the reactor.

Aspect 6 is the process of any one of aspects 1-5, wherein the inert material flows coaxially with respect to the outer surface of the end of the reactor inlet via an annular space formed between an inner surface of an inlet sleeve and the outer surface of the reactor inlet.

Aspect 7 is the process of any one of aspects 1-6, wherein the inert material flows into the reactor via the annular space separately from the flow of the reactant into the reactor via the end of the reactor inlet.

Aspect 8 is the process of any one of aspects 6-7, wherein an exit plane of the end of the reactor inlet is spaced apart from an exit plane of an end of the inlet sleeve.

Aspect 9 is the process of any one of aspects 6-8, wherein the end of the reactor inlet extends outside of the inlet sleeve.

Aspect 10 is the process of any one of aspects 6-8, wherein the end of the reactor inlet is contained within the inlet sleeve.

Aspect 11 is the process of any one of aspects 6-7, wherein the end of the reactor inlet and an end of the inlet sleeve terminate in a common plane.

Aspect 12 is the process of any one of aspects 1-11, further comprising:
feeding a catalyst system to the reactor via a catalyst inlet or via the reactor inlet.

Aspect 13 is the process of any one of aspects 1-12, wherein flowing the inert material into the reactor provides a turbulent region at an injection point.

Aspect 14 is a system to prevent fouling of a reactor inlet, the apparatus comprising:
a reactor;
a reactor inlet coupled with the reactor such that an end of the reactor inlet extends into an interior of the reactor; and
an inlet sleeve coupled with the reactor such that an end of the inlet sleeve extends into the interior of the reactor,
wherein the inlet sleeve is placed coaxially around at least a portion of the reactor inlet such that an annular space is formed between an outer surface of the reactor inlet and an inner surface of the inlet sleeve.

Aspect 15 is the system of aspect 14, further comprising:
a reactant source coupled to the reactor, wherein the reactant source provides a reactant, a diluent, or a mixture of the reactant and diluent to reactor via the reactor inlet; and
an inert material source coupled to the reactor, wherein the inert material source provides an inert material to the reactor via the annular space.

Aspect 16 is the system of any one of aspects 14-15, further comprising:
a catalyst system source coupled to the reactor, wherein the catalyst system source provides a catalyst system to the reactor via the reactor inlet or via a catalyst inlet.

Aspect 17 is the system of any one of aspects 14-16, wherein the reactant is a first petrochemical, and wherein the inert material is selected from a second petrochemical, nitrogen, argon, or a combination thereof.

Aspect 18 is the system of any one of aspects 14-17, wherein the reactor is an oligomerization reactor, wherein the reactant is an olefin, and wherein the inert material is the same as the diluent.

Aspect 19 is the system of any one of aspects 14-18, wherein an exit plane of the end of the reactor inlet is spaced apart from an exit plane of the end of the inlet sleeve.

Aspect 20 is the system of any one of aspects 14-19, wherein the end of the reactor inlet extends outside of the inlet sleeve.

Aspect 21 is the system of any one of aspects 14-19, wherein the end of the reactor inlet is contained within the inlet sleeve.

Aspect 22 is the system of any one of aspects 14-18, wherein the end of the reactor inlet and the end of the inlet sleeve terminate in a common plane in the interior of the reactor.

Aspect 23 is the system of any one of aspects 14-22, wherein the annular space is formed both inside and outside of the reactor.

While aspects and embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15, . . . ). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention.

What is claimed is:

1. A process for introducing reactants into an oligomerization reactor inlet, the process comprising:
   flowing ethylene into an oligomerization reactor via the oligomerization reactor inlet such that the ethylene is introduced to an interior of the oligomerization reactor via an end of the oligomerization reactor inlet; and
   flowing a saturated hydrocarbon into the oligomerization reactor coaxially with respect to an outer surface of the end of the oligomerization reactor inlet; and
wherein the saturated hydrocarbon flows coaxially with respect to the outer surface of the end of the oligomerization reactor inlet via an annular space formed between an inner surface of an inlet sleeve and the outer surface of the oligomerization reactor inlet.

2. The process of claim 1, further comprising feeding a catalyst system to the oligomerization reactor via a catalyst inlet or via the oligomerization reactor inlet, the catalyst system comprising
   1) a chromium component comprising a chromium compound, a heteroatomic ligand, and an aluminoxane; or
   2) a chromium component comprising a heteroatomic ligand chromium compound complex, and an aluminoxane.

3. The process of claim 1, further comprising feeding a catalyst system to the oligomerization reactor via a catalyst inlet or via the oligomerization reactor inlet, the catalyst system comprising:
   1) i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and
   ii) an aluminoxane;
   2) i) a chromium component comprising a chromium compound having the formula $CrX_p$,
   ii) a heteroatomic ligand having the formula
   $(R^{1s})_m X^{1s}(L^{1s})X^{2s}(R^{2s})_n$ or

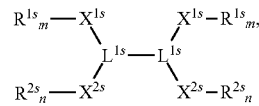

and
   iii) an aluminoxane; or
   3) i) a chromium component comprising a heteroatomic ligand chromium compound complex having the formula

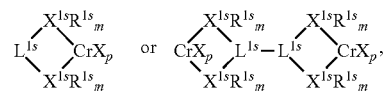

and
   ii) an aluminoxane;
wherein each $X^{1s}$ and each $X^{2s}$ is independently selected from the group consisting of N, P, O, and S,
wherein each $L^{1s}$ is an independent linking group between the respective $X^{1s}$s and $X^{2s}$s and independently are an organylene group, an amin-di-yl group, or a phosphin-di-yl group,
wherein each $R^{1s}$ and each $R^{2s}$ are independently hydrogen, an organyl group or a heterohydrocarbyl group, where when there are two or more $R^{1s}$s and/or two $R^{2s}$s, each $R^{1s}$ can be the same or different and/or each $R^{2s}$ can be the same or different,
wherein each m and each n are independently 1 or 2, and
wherein X represents a monoanionic ligand selected from a halide, a carboxylate, a β-diketonate, a hydrocarboxide, a nitrate, or a chlorate, and p can be from 2 to 4.

4. The process of claim 3, wherein the catalyst system comprises
   i) an $N^2$-phosphinyl formamidine chromium compound complex having structure

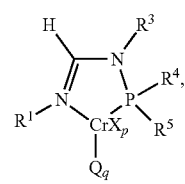

an $N^2$-phosphinyl amidine chromium compound complex having structure

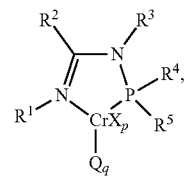

an $N^2$-phosphinyl guanidine chromium compound complex having the structure

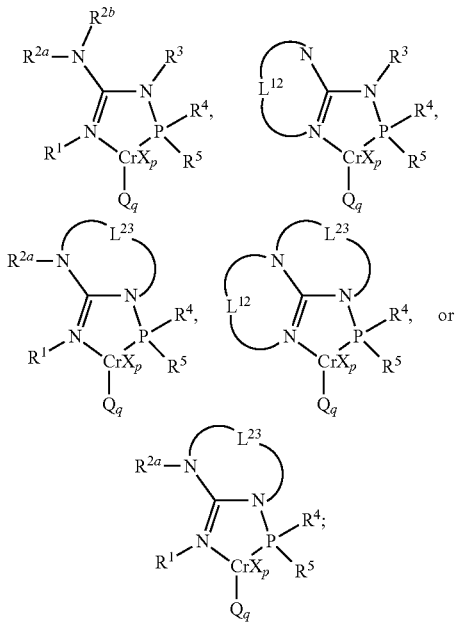

and
wherein
$R^1$ is a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group,
$R^2$ is a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group,
$R^{2a}$ and $R^{2b}$ independently are $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group,
$L^{12}$ and $L^{23}$ independently are a $C_2$ to $C_{20}$ organylene group consisting of inert functional groups,
$L^{22}$ is a $C_3$ to $C_{20}$ organylene group consisting of inert functional groups,
$R^3$ is hydrogen, a $C_1$ to $C_{20}$ alkyl group, a phenyl group, or a $C_6$ to $C_{20}$ substituted phenyl group,
$R^4$ and $R^5$ are each independently a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group,
$CrX_p$ represents the chromium salt where X is a $C_1$ to $C_{20}$ carboxylate, a $C_1$ to $C_{20}$ β-diketonate, or a halide, and p ranges from 2 to 3,
Q is a neutral ligand and each neutral ligand independently is a $C_2$ to $C_{20}$ nitrile or a $C_2$ to $C_{40}$ ether, a ranges from 0 to 6, and
wherein each substituent independently can be a halide, a hydrocarbyl group, or a hydrocarboxy group, and ii) an aluminoxane comprising methylaluminoxane, modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof.

5. The process of claim 4, wherein
$R^1$ is a phenyl group or a $C_6$ to $C_{10}$ substituted phenyl group,
$R^2$ is a $C_6$ to $C_{10}$ aryl group, a $C_6$ to $C_{10}$ substituted aryl group, a $C_7$ to $C_{10}$ aralkyl group, or a $C_7$ to $C_{10}$ substituted aralkyl group,
$R^{2a}$ and $R^{2b}$ independently are a $C_1$ to $C_5$ alkyl group, a $C_4$ to $C_{10}$ cycloalkyl group, a phenyl group, or a $C_6$ to $C_{10}$ substituted phenyl group,
$L^{12}$ and $L^{23}$ independently are $C_2$ to $C_{10}$ hydrocarbylene group,
$L^{22}$ is a $C_4$ to $C_{10}$ hydrocarbylene group,
$R^3$ is hydrogen,
$R^4$ and $R^5$ are each independently a $C_1$ to $C_{10}$ alkyl group, a $C_4$ to $C_{10}$ cycloalkyl group, a phenyl group, or a $C_6$ to $C_{20}$ substituted phenyl group.

6. The process of claim 3, wherein the catalyst system comprises
1) i) a chromium component comprising a chromium compound having the formula $CrX_p$,
ii) a heteroatomic ligand having the formula $R^{1s}S(L^{1s})SR^{2s}$, $(R^{1s})_2P(L^{1s})P(R^{2s})_2$, or $(R^{1s})_2N(L^{1s})N(R^{2s})_2$, and
iii) an aluminoxane; or
2) i) a chromium component comprising a heteroatomic ligand chromium compound complex having the formula

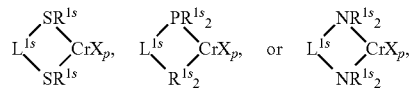

and
ii) an aluminoxane;
wherein $L^{1s}$ has the -$(L^{3s})NR^{5s}(L^{4s})$-, -$(L^{3s})PR^{5s}(L^{4s})$-, —$N(R^{5s})$—, or —$P(R^{5s})$— where $L^{3s}$ and $L^{4s}$ independently are a $C_1$ to $C_{20}$ organylene group consisting of inert functional groups and $R^{5s}$ is a $C_1$ to $C_{20}$ alkyl group, a substituted $C_1$ to $C_{20}$ alkyl group, a $C_4$ to $C_{20}$ cycloalkyl group, a substituted $C_4$ to $C_{20}$ cycloalkyl group, a $C_6$ to $C_{20}$ aryl group, a substituted $C_6$ to $C_{20}$ aryl group, a $C_7$ to $C_{20}$ aralkyl group, or a $C_7$ to $C_{20}$ substituted aralkyl group where each substituent of the substituted alkyl group, substituted cycloalkyl group, substituted aryl group, or substituted aralkyl group is a halogen, hydrocarbyl group, or a hydrocarboxyl group;
wherein each $R^{1s}$ and each $R^{2s}$ independently are a $C_1$ to $C_{20}$ alkyl group, a substituted $C_1$ to $C_{20}$ alkyl group, a $C_4$ to $C_{20}$ cycloalkyl group, a substituted $C_4$ to $C_{20}$ cycloalkyl group, a $C_6$ to $C_{20}$ aryl group, a substituted $C_6$ to $C_{20}$ aryl group, a $C_7$ to $C_{20}$ aralkyl group, or a $C_7$ to $C_{20}$ substituted aralkyl group;
where X is a halide, a $C_1$ to $C_{20}$ carboxylate, a $C_1$ to $C_{20}$ β-diketonate, or a halide, and p ranges from 2 to 3; and
wherein the aluminoxane comprises methylaluminoxane, modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof.

7. The process of claim 6, wherein $L^{3s}$ and $L^{4s}$ independently are a $C_1$ to $C_{10}$ hydrocarbylene group;

$R^{5s}$ is a $C_1$ to $C_{10}$ alkyl group, a $C_5$ to $C_{10}$ cycloalkyl group, a substituted $C_5$ to $C_{10}$ cycloalkyl group, a phenyl group or a $C_6$ to $C_{10}$ substituted phenyl group, or a $C_7$ to $C_{10}$ aralkyl group, where each substituent independently is an alkyl group; and wherein each $R^{1s}$ and each $R^{2s}$ are independently $C_1$ to $C_{10}$ alkyl group, a $C_4$ to $C_{10}$ cycloalkyl group, a $C_6$ to $C_{10}$ aryl group, or a $C_7$ to $C_{10}$ aralkyl group where each substituent independently is an alkyl group.

8. The process of claim 1, wherein the end of the oligomerization reactor inlet extends into the interior of the oligomerization reactor, and wherein an end of the inlet sleeve extends into the interior of the oligomerization reactor.

9. The process of claim 1, further comprising:

flowing the saturated hydrocarbon into the oligomerization reactor via the oligomerization reactor inlet such that a mixture of ethylene and saturated hydrocarbon is introduced to the interior of the oligomerization reactor via the end of the oligomerization reactor inlet, wherein the saturated hydrocarbon which flows into the oligomerization reactor via the oligomerization reactor inlet is a primary source of the saturated hydrocarbon for an oligomerization reaction in the oligomerization reactor, and wherein the saturated hydrocarbon which flow's coaxially into the oligomerization reactor is a secondary source of the saturated hydrocarbon for the oligomerization reaction in the oligomerization reactor.

10. The process of claim 1, wherein the saturated hydrocarbon flows into the oligomerization reactor via the annular space separately from the flow of the ethylene into the oligomerization reactor via the end of the oligomerization reactor inlet.

11. The process of claim 10, wherein the end of the oligomerization reactor inlet extends outside of the inlet sleeve, wherein the end of the oligomerization reactor inlet is contained within the inlet sleeve, or wherein the end of the oligomerization reactor inlet and an end of the inlet sleeve terminate in a common plane.

12. The process of claim 1, wherein flowing the saturated hydrocarbon into the oligomerization reactor provides a turbulent region at an injection point.

13. A system for introducing reactants into an oligomerization reactor inlet, the system comprising:

an oligomerization reactor;

an oligomerization reactor inlet coupled with the oligomerization reactor such that an end of the oligomerization reactor inlet extends into an interior of the oligomerization reactor;

an inlet sleeve coupled with the oligomerization reactor such that an end of the inlet sleeve extends into the interior of the oligomerization reactor;

a reactant source coupled to the oligomerization reactor;

an inert material source coupled to the oligomerization reactor;

wherein the inlet sleeve is placed coaxially around at least a portion of the oligomerization reactor inlet such that an annular space is formed between an outer surface of the oligomerization reactor inlet and an inner surface of the inlet sleeve, wherein the reactant source provides reactant or a mixture of the reactant and diluent to the oligomerization reactor via the oligomerization reactor inlet, wherein the inert material source provides an inert material to the oligomerization reactor via the annular space, wherein the reactant is ethylene, and wherein the inert material and diluent are independently a saturated hydrocarbon.

14. The system of claim 13, further comprising:

a catalyst system source coupled to the oligomerization reactor; and wherein the catalyst system source provides a catalyst system to the oligomerization reactor via the oligomerization reactor inlet or via a catalyst inlet.

15. The system of claim 14, wherein the catalyst system comprises 1) a chromium component comprising a chromium compound, a heteroatomic ligand, and an aluminoxane; or
2) a chromium component comprising a heteroatomic ligand chromium compound complex, and an aluminoxane.

16. The system of claim 15, wherein the catalyst system comprises 1) i) a chromium component comprising an $N^2$-phosphinyl formamidine chromium compound complex, an $N^2$-phosphinyl amidine chromium compound complex, an $N^2$-phosphinyl guanidine chromium compound complex, or any combination thereof, and
   ii) an aluminoxane;
2) i) a chromium component comprising a chromium compound having the formula $CrX_p$,
   ii) a heteroatomic ligand, and
   iii) an aluminoxane; or
3) i) a chromium component comprising a heteroatomic ligand chromium compound complex, and
   ii) an aluminoxane;

where the heteroatomic ligand has the formula $(R^{1s})_m X^{1s}(L^{1s})X^{2s}(R^{2s})_n$ or

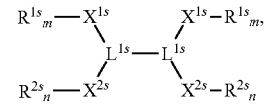

where the heteroatomic ligand chromium compound complex has the formula

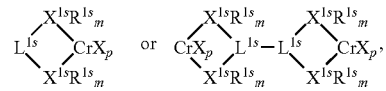

wherein each $X^{1s}$ and each $X^{2s}$ is independently selected from the group consisting of N, P, O, and S, wherein each $L^{1s}$ is an independent linking group between the respective $X^{1s}$s and $X^{2s}$s and independently are an organylene group, an amin-di-yl group, or a phosphin-di-yl group, wherein each $R^{1s}$ and each $R^{2s}$ are independently hydrogen, an organyl group or a heterohydrocarbyl group, where when there are two or more $R^{1s}$s and/or two $R^{2s}$s, each $R^{1s}$ can be the same or different and/or each $R^{2s}$ can be the same or different, wherein each m and each n are independently 1 or 2, and wherein X represents a monoanionic ligand selected from a halide, a carboxylate, a β-diketonate, a hydrocarboxide, a nitrate, or a chlorate, and p can be from 2 to 4.

17. The system of claim 16, wherein the catalyst system comprises i) an $N^2$-phosphinyl formamidine chromium compound complex having structure

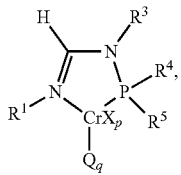

an $N^2$-phosphinyl amidine chromium compound complex having structure or

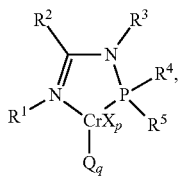

or an $N^2$-phosphinyl guanidine chromium compound complex having the structure

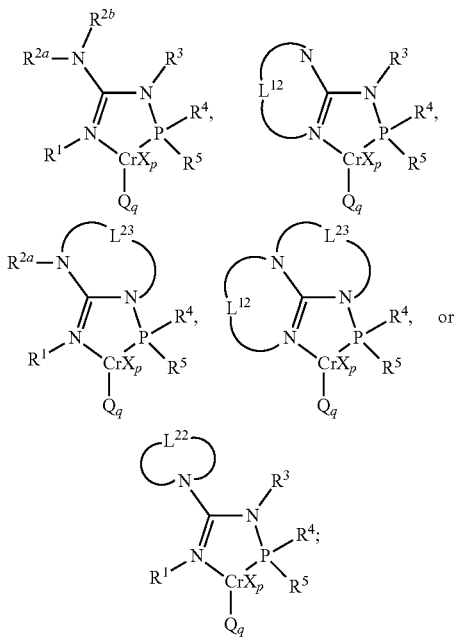

and wherein $R^1$ is a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group, $R^2$ is a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group, $R^{2a}$ and $R^{2b}$ independently are $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group, $L^{12}$ and $L^{23}$ independently are a $C_2$ to $C_{20}$ organylene group consisting of inert functional groups, $L^{22}$ is a $C_3$ to $C_{20}$ organylene group consisting of inert functional groups, $R^3$ is hydrogen, a $C_1$ to $C_{20}$ alkyl group, a phenyl group, or a $C_6$ to $C_{20}$ substituted phenyl group, $R^4$ and $R^5$ are each independently a $C_1$ to $C_{20}$ alkyl group, a $C_1$ to $C_{20}$ substituted alkyl group, a $C_4$ to $C_{20}$ cycloalkyl group, a $C_4$ to $C_{20}$ substituted cycloalkyl group, a $C_6$ to $C_{20}$ aryl group, a $C_6$ to $C_{20}$ substituted aryl group, a $C_7$ to $C_{20}$ aralkyl group, or a $C_7$ to $C_{20}$ substituted aralkyl group, $CrX_p$ represents the chromium salt where X is a $C_1$ to $C_{20}$ carboxylate, a $C_1$ to $C_{20}$ β-diketonate, or a halide, and p ranges from 2 to 3, Q is a neutral ligand and each neutral ligand independently is a $C_2$ to $C_{20}$ nitrile or a $C_2$ to $C_{40}$ ether, a ranges from 0 to 6, and wherein each substituent independently can be a halide, a hydrocarbyl group, or a hydrocarboxy group, and ii) an aluminoxane comprising methylaluminoxane, modified methylaluminoxane, ethylaluminoxane, n-propylaluminoxane, iso-propyl aluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof.

18. The system of claim 17, wherein $R^1$ is a phenyl group or a $C_6$ to $C_{10}$ substituted phenyl group, $R^2$ is a $C_6$ to $C_{10}$ aryl group, a $C_6$ to $C_{10}$ substituted aryl group, a $C_7$ to $C_{10}$ aralkyl group, or a $C_7$ to $C_{10}$ substituted aralkyl group, $R^{2a}$ and $R^{2b}$ independently are a $C_1$ to $C_5$ alkyl group, a $C_4$ to $C_{10}$ cycloalkyl group, a phenyl group, or a $C_4$ to $C_{10}$ substituted phenyl group, $L^{12}$ and $L^{23}$ independently are $C_2$ to $C_{10}$ hydrocarbylene group, $L^{22}$ is a $C_4$ to $C_{10}$ hydrocarbylene group, $R^3$ is hydrogen, and $R^4$ and $R^5$ are each independently a $C_1$ to $C_{10}$ alkyl group, a $C_4$ to $C_{10}$ cycloalkyl group, a phenyl group, or a $C_6$ to $C_{20}$ substituted phenyl group.

19. The system of claim 16, wherein the catalyst system comprises 1) i) a chromium component comprising a chromium compound having the formula $CrX_p$, ii) a heteroatomic ligand having the formula $R^{1s}S(L^{1s})SR^{2s}$, $(R^{1s})_2P(L^{1s})P(R^{2s})_2$, or $(R^{1s})_2N(L^{1s})N(R^{2s})_2$, and iii) an aluminoxane; or 2) i) a chromium component comprising a heteroatomic ligand chromium compound complex having the formula

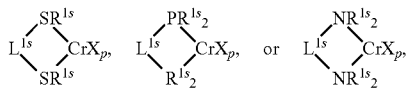

and ii) an aluminoxane;

wherein $L^{1s}$ has the $-(L^{3s})NR^{5s}(L^{4s})-$, $-(L^{3s})PR^{5s}(L^{4s})-$, $-N(R^{5s})-$, or $-P(R^{5s})-$ where $L^{3s}$ and $L^{4s}$ independently are a $C_1$ to $C_{20}$ organylene group consisting of inert functional groups and $R^{5s}$ is a $C_1$ to $C_{20}$ alkyl group, a substituted $C_1$ to $C_{20}$ alkyl group, a $C_4$ to $C_{20}$ cycloalkyl group, a substituted $C_4$ to $C_{20}$ cycloalkyl group, a $C_6$ to $C_{20}$ aryl group, a substituted $C_6$ to $C_{20}$ aryl group, a $C_7$ to $C_{20}$ aralkyl group, or a $C_7$ to $C_{20}$ substituted aralkyl group, wherein each $R^{1s}$ and each $R^{2s}$ independently are a $C_1$ to $C_{20}$ alkyl group, a substituted $C_1$ to $C_{20}$ alkyl group, a $C_4$ to $C_{20}$ cycloalkyl group, a substituted $C_4$ to $C_{20}$ cycloalkyl group, a $C_6$ to $C_{20}$ aryl group, a substituted $C_6$ to $C_{20}$ aryl group, a $C_7$ to $C_{20}$ aralkyl group, or a $C_7$ to $C_{20}$ substituted aralkyl group, wherein each substituent is a halogen, hydrocarbyl group, or a hydrocarboxyl group, wherein X is a halide, a $C_4$ to $C_{20}$ carboxylate, a $C_1$ to $C_{20}$ β-diketonate, or a halide, and p ranges from 2 to 3, and wherein the aluminoxane comprises methylaluminoxane, modified methylaluminoxane, ethylaluminoxane, n-propylaluminoxane, iso-propylaluminoxane, n-butylaluminoxane, sec-butylaluminoxane, iso-butylaluminoxane, t-butyl aluminoxane, 1-pentylaluminoxane, 2-pentylaluminoxane, 3-pentylaluminoxane, iso-pentylaluminoxane, neopentylaluminoxane, and mixtures thereof.

20. The system of claim 19, wherein
$L^{3s}$ and $L^{4s}$ independently are a $C_1$ to $C_{10}$ hydrocarbylene group;
$R^{5s}$ is a $C_1$ to $C_{10}$ alkyl group, a $C_5$ to $C_{10}$ cycloalkyl group, a substituted $C_5$ to $C_{10}$ cycloalkyl group, a phenyl group or a $C_6$ to $C_{10}$ substituted phenyl group, or a $C_7$ to $C_{10}$ aralkyl group, where each substituent independently is an alkyl group; and
wherein each $R^{1s}$ and each $R^{2s}$ are independently $C_1$ to $C_{10}$ alkyl group, a $C_4$ to $C_{10}$ cycloalkyl group, a $C_6$ to $C_{10}$ aryl group, or a $C_7$ to $C_{10}$ aralkyl group where each substituent independently is an alkyl group.

21. The system of claim 13, wherein the end of the oligomerization reactor inlet extends outside of the inlet sleeve, the end of the oligomerization reactor inlet is contained within the inlet sleeve, or the end of the oligomerization reactor inlet and the end of the inlet sleeve terminate in a common plane in the interior of the reactor.

22. The system of claim 13, wherein the annular space is formed both inside and outside of the oligomerization reactor.

* * * * *